(12) United States Patent
Chang et al.

(10) Patent No.: US 8,777,926 B2
(45) Date of Patent: Jul. 15, 2014

(54) APPARATUS AND METHODS FOR DILATING AND MODIFYING OSTIA OF PARANASAL SINUSES AND OTHER INTRANASEL OR PARANASAL STRUCTURES

(71) Applicant: Acclarent, Inc., Menlo Park, CA (US)

(72) Inventors: John Y Chang, Mountain View, CA (US); Joshua Makower, Los Altos, CA (US); Julia D Vrany, Sunnyvale, CA (US); Amrish Jayprakash Walke, Mountain View, CA (US)

(73) Assignee: Acclarent, Inc., Menlo Park, CA (US)

( * ) Notice: Subject to any disclaimer, the term of this patent is extended or adjusted under 35 U.S.C. 154(b) by 0 days.

(21) Appl. No.: 13/840,430

(22) Filed: Mar. 15, 2013

(65) Prior Publication Data

US 2013/0325052 A1 Dec. 5, 2013

Related U.S. Application Data

(63) Continuation of application No. 12/768,963, filed on Apr. 28, 2010, which is a continuation of application No. 10/944,270, filed on Sep. 17, 2004, now abandoned, which is a continuation-in-part of application No. 10/829,917, filed on Apr. 21, 2004, now Pat. No. 7,654,997.

(51) Int. Cl.
*A61M 31/00* (2006.01)

(52) U.S. Cl.
USPC ......... 604/509; 604/510; 604/96.01; 606/192

(58) Field of Classification Search
USPC ........ 264/285, 339, DIG. 30, DIG. 66; 425/2; 604/516, 528, 509, 510, 96.01; 600/114; 606/192
See application file for complete search history.

(56) References Cited

U.S. PATENT DOCUMENTS

| 446,173 A | 2/1891 | Hancock |
|---|---|---|
| 504,424 A | 9/1893 | De Pezzer |

(Continued)

FOREIGN PATENT DOCUMENTS

| CA | 2013323 | 9/1990 |
|---|---|---|
| CH | 668188 | 12/1988 |

(Continued)

OTHER PUBLICATIONS

Argon Medical. Maxxim Medical. Ad for Sniper EliteTM Hydrophilic Ni—Ti Alloy Guidewire (2001).

(Continued)

*Primary Examiner* — Kevin C Sirmons
*Assistant Examiner* — Deanna K Hall
(74) *Attorney, Agent, or Firm* — Frost Brown Todd LLC

(57) ABSTRACT

Sinusitis and other disorders of the ear, nose and throat are diagnosed and/or treated using minimally invasive approaches with flexible or rigid instruments. Various methods and devices are used for remodeling or changing the shape, size or configuration of a sinus ostium or duct or other anatomical structure in the ear, nose or throat; implanting a device, cells or tissues; removing matter from the ear, nose or throat; delivering diagnostic or therapeutic substances or performing other diagnostic or therapeutic procedures. Introducing devices (e.g., guide catheters, tubes, guidewires, elongate probes, other elongate members) may be used to facilitate insertion of working devices (e.g. catheters e.g. balloon catheters, guidewires, tissue cutting or remodeling devices, devices for implanting elements like stents, electrosurgical devices, energy emitting devices, devices for delivering diagnostic or therapeutic agents, substance delivery implants, scopes etc.) into the paranasal sinuses or other structures in the ear, nose or throat.

18 Claims, 35 Drawing Sheets

(56) References Cited

U.S. PATENT DOCUMENTS

| | | | |
|---|---|---|---|
| 513,667 A | 1/1894 | Buckingham |
| 705,346 A | 7/1902 | Hamilton |
| 798,775 A | 9/1905 | Forsyte |
| 816,792 A | 4/1906 | Green |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,493,326 A | 1/1950 | Trinder |
| 2,525,183 A | 10/1950 | Robison |
| 2,847,997 A | 8/1958 | Tibone |
| 2,899,227 A | 8/1959 | Jeanrenaud |
| 2,906,179 A | 9/1959 | Bower |
| 2,995,832 A | 8/1961 | Alderson |
| 3,009,265 A | 11/1961 | Bexark |
| 3,037,286 A | 6/1962 | Bower |
| 3,173,418 A | 3/1965 | Baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,447,061 A | 5/1969 | Russell et al. |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow |
| 3,731,963 A | 5/1973 | Pond |
| 3,766,924 A | 10/1973 | Pidgeon |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita |
| 3,834,394 A | 9/1974 | Hunter et al. |
| 3,847,145 A | 11/1974 | Grossan |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,312,353 A | 1/1982 | Shahbabian |
| 4,338,941 A | 7/1982 | Payton |
| D269,204 S | 5/1983 | Trepp |
| 4,388,941 A | 6/1983 | Reidhammer |
| RE31,351 E | 8/1983 | Falconer |
| 4,435,716 A | 3/1984 | Zandbergen |
| 4,437,856 A | 3/1984 | Valli |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A * | 4/1986 | Sahota ............... 604/101.01 |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,691,948 A | 9/1987 | Austin, Jr. et al. |
| 4,705,801 A | 11/1987 | Martin et al. |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |
| 4,771,776 A | 9/1988 | Powell et al. |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |
| 4,847,258 A | 7/1989 | Sturm et al. |
| 4,851,228 A | 7/1989 | Zentner et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,961,433 A | 10/1990 | Christian |
| 4,966,163 A | 10/1990 | Kraus et al. |
| 4,984,581 A | 1/1991 | Stice |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,009,655 A | 4/1991 | Daignault, Jr. et al. |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |

(56) References Cited

U.S. PATENT DOCUMENTS

| | | |
|---|---|---|
| 5,024,658 A | 6/1991 | Kozlov et al. |
| 5,026,384 A | 6/1991 | Farr et al. |
| 5,030,227 A | 7/1991 | Rosenbluth et al. |
| 5,041,089 A | 8/1991 | Mueller et al. |
| 5,044,678 A | 9/1991 | Detweiler |
| 5,053,007 A | 10/1991 | Euteneuer |
| 5,055,051 A | 10/1991 | Duncan |
| 5,060,660 A | 10/1991 | Gamble et al. |
| 5,067,489 A | 11/1991 | Lind |
| 5,069,226 A | 12/1991 | Tamauchi et al. |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,102,402 A | 4/1992 | Dror et al. |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Oliver |
| 5,156,595 A | 10/1992 | Adams |
| 5,163,989 A | 11/1992 | Campbell et al. |
| 5,167,220 A | 12/1992 | Brown |
| 5,168,864 A | 12/1992 | Skockey |
| 5,169,043 A | 12/1992 | Catania |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,197,457 A | 3/1993 | Adair |
| 5,207,695 A | 5/1993 | Trout, III |
| 5,211,952 A | 5/1993 | Spicer et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,238,004 A | 8/1993 | Sahatjian et al. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deneiga |
| 5,269,752 A | 12/1993 | Bennett |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,295,694 A | 3/1994 | Levin |
| 5,300,085 A | 4/1994 | Yock |
| 5,304,123 A | 4/1994 | Atala et al. |
| 5,308,326 A | 5/1994 | Zimmon |
| 5,312,430 A | 5/1994 | Rosenbluth et al. |
| 5,313,967 A | 5/1994 | Lieber et al. |
| 5,314,408 A | 5/1994 | Salmon et al. |
| 5,314,417 A | 5/1994 | Stephens et al. |
| 5,315,618 A | 5/1994 | Yoshida |
| 5,318,528 A | 6/1994 | Heaven et al. |
| 5,324,306 A | 6/1994 | Makower et al. |
| 5,333,620 A | 8/1994 | Moutafis et al. |
| 5,334,167 A | 8/1994 | Cocanower |
| 5,334,187 A | 8/1994 | Fischell et al. |
| 5,335,671 A | 8/1994 | Clement |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |
| 5,372,138 A | 12/1994 | Crowley et al. |
| 5,372,584 A | 12/1994 | Zink et al. |
| D355,031 S | 1/1995 | Yoshikawa |
| 5,386,817 A | 2/1995 | Jones |
| 5,391,147 A | 2/1995 | Imran et al. |
| 5,391,179 A | 2/1995 | Mezzoli |
| 5,402,799 A | 4/1995 | Colon et al. |
| 5,409,444 A | 4/1995 | Kensey |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,445,646 A | 8/1995 | Euteneuer et al. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,459,700 A | 10/1995 | Jacobs |
| 5,465,717 A | 11/1995 | Imran et al. |
| 5,465,733 A | 11/1995 | Hinohara et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,507,795 A | 4/1996 | Chiang et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wong |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,578,007 A | 11/1996 | Imran |
| 5,578,048 A | 11/1996 | Pasqualucci et al. |
| 5,582,575 A | 12/1996 | Heckele et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |

(56) References Cited

U.S. PATENT DOCUMENTS

| | | |
|---|---|---|
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,376 A | 1/1998 | Kavteladze et al. |
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,824,044 A | 10/1998 | Quiachon et al. |
| 5,824,048 A | 10/1998 | Tuch |
| 5,824,173 A | 10/1998 | Fontirroche et al. |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Shatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,879,324 A | 3/1999 | Von Hoffmann |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,997,562 A | 12/1999 | Zadno-Azizi et al. |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,063,079 A | 5/2000 | Hovda et al. |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,109,268 A | 8/2000 | Thapliyal et al. |
| 6,113,567 A | 9/2000 | Becker |
| 6,117,105 A | 9/2000 | Bresnaham et al. |
| 6,122,541 A | 9/2000 | Cosman et al. |
| 6,123,697 A | 9/2000 | Shippert |
| 6,135,991 A | 10/2000 | Muni et al. |
| 6,136,006 A | 10/2000 | Johnson et al. |
| 6,139,510 A | 10/2000 | Palermo |
| 6,142,957 A | 11/2000 | Diamond et al. |
| 6,146,415 A | 11/2000 | Fitz |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,788 B1 | 1/2001 | Sullivan |
| 6,179,811 B1 | 1/2001 | Fugoso et al. |
| 6,183,433 B1 | 2/2001 | Bays |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,206,900 B1 | 3/2001 | Tabatabaei et al. |
| 6,213,975 B1 | 4/2001 | Laksin |
| 6,221,042 B1 | 4/2001 | Adams |
| 6,231,543 B1 | 5/2001 | Hedge et al. |
| 6,234,958 B1 | 5/2001 | Snoke et al. |
| 6,238,364 B1 | 5/2001 | Becker |
| 6,238,391 B1 | 5/2001 | Olsen et al. |

(56) References Cited

U.S. PATENT DOCUMENTS

| | | |
|---|---|---|
| 6,241,519 B1 | 6/2001 | Sedleemayer |
| 6,249,180 B1 | 6/2001 | Maalej et al. |
| 6,254,550 B1 | 7/2001 | McNamara et al. |
| 6,268,574 B1 | 7/2001 | Edens |
| 6,270,477 B1 | 8/2001 | Bagaoisan et al. |
| 6,290,689 B1 | 9/2001 | Delaney et al. |
| 6,293,957 B1 | 9/2001 | Peters et al. |
| 6,295,990 B1 | 10/2001 | Lewis et al. |
| 6,302,875 B1 | 10/2001 | Makower et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,332,089 B1 | 12/2001 | Acker et al. |
| 6,332,891 B1 | 12/2001 | Himes |
| 6,340,360 B1 | 1/2002 | Lyles et al. |
| 6,344,028 B1 | 2/2002 | Barry |
| 6,348,041 B1 | 2/2002 | Klint |
| 6,352,503 B1 | 3/2002 | Matsui et al. |
| 6,364,856 B1 | 4/2002 | Ding et al. |
| 6,375,615 B1 | 4/2002 | Flaherty et al. |
| 6,375,629 B1 | 4/2002 | Muni et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,419,653 B2 | 7/2002 | Edwards et al. |
| 6,423,012 B1 | 7/2002 | Kato et al. |
| 6,425,877 B1 | 7/2002 | Edwards |
| 6,432,986 B2 | 8/2002 | Levin |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,488,653 B1 | 12/2002 | Lombardo |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,503,263 B2 | 1/2003 | Adams |
| 6,511,418 B2 | 1/2003 | Shahidi et al. |
| 6,514,249 B1 | 2/2003 | Maguire et al. |
| 6,517,478 B2 | 2/2003 | Khadem |
| 6,524,129 B2 | 2/2003 | Cote et al. |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,223 B1 | 4/2003 | Kokish |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,718 B2 | 7/2003 | Hayzelden et al. |
| 6,585,794 B2 | 7/2003 | Shimoda et al. |
| 6,589,164 B1 | 7/2003 | Flaherty |
| 6,589,237 B2 | 7/2003 | Woloszko et al. |
| 6,591,130 B2 | 7/2003 | Shahidi |
| 6,596,009 B1 | 7/2003 | Jelic |
| 6,607,546 B1 | 8/2003 | Murken |
| 6,610,059 B1 | 8/2003 | West, Jr. |
| 6,612,999 B2 | 9/2003 | Brennan et al. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,652,472 B2 | 11/2003 | Jafari et al. |
| 6,652,480 B1 | 11/2003 | Imran et al. |
| 6,656,166 B2 | 12/2003 | Lurie et al. |
| 6,659,106 B1 | 12/2003 | Hovda et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,871 B2 | 1/2004 | Hahnen |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,719,763 B2 | 4/2004 | Chung et al. |
| 6,726,701 B2 | 4/2004 | Gilson et al. |
| 6,738,656 B1 | 5/2004 | Ferre et al. |
| 6,755,812 B2 | 6/2004 | Peterson et al. |
| 6,776,772 B1 | 8/2004 | de Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,811,544 B2 | 11/2004 | Schaer |
| 6,817,364 B2 | 11/2004 | Garibaldi et al. |
| 6,817,976 B2 | 11/2004 | Rovengo |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,851,290 B2 | 2/2005 | Meier et al. |
| 6,855,136 B2 | 2/2005 | Dorros et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,984,203 B2 | 1/2006 | Tartaglia et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,004,176 B2 | 2/2006 | Lau |

(56) References Cited

U.S. PATENT DOCUMENTS

| | | |
|---|---|---|
| 7,008,412 B2 | 3/2006 | Maginot |
| 7,011,654 B2 | 3/2006 | Dubrul et al. |
| 7,022,105 B1 | 4/2006 | Edwards |
| 7,043,961 B2 | 5/2006 | Pandey |
| 7,044,964 B2 | 5/2006 | Jang et al. |
| 7,052,474 B2 | 5/2006 | Castell et al. |
| 7,056,284 B2 | 6/2006 | Martone et al. |
| 7,056,303 B2 | 6/2006 | Dennis et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,207,981 B2 | 4/2007 | Quinn et al. |
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |
| 7,292,885 B2 | 11/2007 | Scott et al. |
| 7,294,345 B2 | 11/2007 | Haapakumpu et al. |
| 7,294,365 B2 | 11/2007 | Hayakawa et al. |
| 7,303,533 B2 | 12/2007 | Johansen et al. |
| 7,313,430 B2 | 12/2007 | Urquhart et al. |
| 7,316,168 B2 | 1/2008 | van der Knokke et al. |
| 7,316,656 B2 | 1/2008 | Shireman et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,347,868 B2 | 3/2008 | Burnett et al. |
| 7,359,755 B2 | 4/2008 | Jones et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,481,218 B2 | 1/2009 | Djupesland |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,559,925 B2 | 7/2009 | Goldfarb et al. |
| 7,610,104 B2 | 10/2009 | Kaplan et al. |
| 7,615,005 B2 | 11/2009 | Stefanchik et al. |
| 7,618,450 B2 | 11/2009 | Zarowski et al. |
| 7,625,335 B2 | 12/2009 | Deichmann et al. |
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,691,120 B2 | 4/2010 | Shluzas et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,736,301 B1 | 6/2010 | Webler et al. |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,775,968 B2 | 8/2010 | Mathis |
| 7,785,315 B1 | 8/2010 | Muni et al. |
| 7,799,048 B2 | 9/2010 | Hudson et al. |
| 7,799,337 B2 | 9/2010 | Levin |
| 7,803,150 B2 | 9/2010 | Chang et al. |
| 7,833,282 B2 | 11/2010 | Mandpe |
| 7,837,672 B2 | 11/2010 | Intoccia |
| 7,840,254 B2 | 11/2010 | Glossop |
| 7,854,744 B2 | 12/2010 | Becker |
| D630,321 S | 1/2011 | Hamilton, Jr. |
| 7,875,050 B2 | 1/2011 | Samson et al. |
| D632,791 S | 2/2011 | Murner |
| 7,881,769 B2 | 2/2011 | Sobe |
| 7,883,717 B2 | 2/2011 | Varner et al. |
| 7,896,891 B2 | 3/2011 | Catanese, III et al. |
| 7,951,132 B2 | 5/2011 | Eaton et al. |
| 7,988,705 B2 | 8/2011 | Galdonik et al. |
| 7,993,353 B2 | 8/2011 | Roβner et al. |
| 8,002,740 B2 | 8/2011 | Willink et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,100,933 B2 | 1/2012 | Becker |
| 8,104,483 B2 | 1/2012 | Taylor |
| 8,114,062 B2 | 2/2012 | Muni et al. |
| 8,114,113 B2 | 2/2012 | Becker |
| 8,123,722 B2 | 2/2012 | Chang et al. |
| 8,142,422 B2 | 3/2012 | Makower et al. |
| 8,146,400 B2 | 4/2012 | Goldfarb et al. |
| 8,147,545 B2 | 4/2012 | Avior |
| 8,167,821 B2 | 5/2012 | Sharrow |
| 8,172,828 B2 | 5/2012 | Chang et al. |
| 8,190,389 B2 | 5/2012 | Kim et al. |
| 8,197,433 B2 | 6/2012 | Cohen |
| 8,197,552 B2 | 6/2012 | Mandpe |
| 8,249,700 B2 | 8/2012 | Clifford et al. |
| 8,277,386 B2 | 10/2012 | Ahmed et al. |
| 8,317,816 B2 | 11/2012 | Becker |
| 8,337,454 B2 | 12/2012 | Eaton et al. |
| 8,388,642 B2 | 3/2013 | Muni et al. |
| 8,403,954 B2 | 3/2013 | Santin et al. |
| 8,414,473 B2 | 4/2013 | Jenkins et al. |
| 8,425,457 B2 | 4/2013 | John et al. |
| 8,439,687 B1 | 5/2013 | Morriss et al. |
| 8,535,707 B2 | 9/2013 | Arensdorf et al. |
| 2001/0004644 A1 | 6/2001 | Levin |
| 2001/0005785 A1 | 6/2001 | Sachse |
| 2001/0034530 A1 | 10/2001 | Malackowski et al. |
| 2002/0006961 A1 | 1/2002 | Katz et al. |
| 2002/0055746 A1 | 5/2002 | Burke et al. |
| 2002/0077593 A1 | 6/2002 | Perkins et al. |
| 2002/0090388 A1 | 7/2002 | Humes et al. |
| 2003/0013985 A1 | 1/2003 | Saadat |
| 2003/0017111 A1 | 1/2003 | Rabito |
| 2003/0018291 A1 | 1/2003 | Hill et al. |
| 2003/0040697 A1 | 2/2003 | Pass et al. |
| 2003/0073900 A1 | 4/2003 | Senarith et al. |

(56) References Cited

U.S. PATENT DOCUMENTS

| | | |
|---|---|---|
| 2003/0083608 A1 | 5/2003 | Evans et al. |
| 2003/0114732 A1 | 6/2003 | Webler et al. |
| 2003/0163154 A1 | 8/2003 | Miyata et al. |
| 2003/0220551 A1 | 11/2003 | Kimball et al. |
| 2004/0015150 A1 | 1/2004 | Zadno-Azizi |
| 2004/0018980 A1 | 1/2004 | Gurney et al. |
| 2004/0020492 A1 | 2/2004 | Dubrul et al. |
| 2004/0034311 A1 | 2/2004 | Mihakcik |
| 2004/0043052 A1 | 3/2004 | Hunter et al. |
| 2004/0058992 A1 | 3/2004 | Marinello et al. |
| 2004/0064105 A1 | 4/2004 | Capes et al. |
| 2004/0064150 A1* | 4/2004 | Becker .................. 606/196 |
| 2004/0116958 A1 | 6/2004 | Gopferich et al. |
| 2004/0127820 A1 | 7/2004 | Clayman et al. |
| 2004/0158229 A1 | 8/2004 | Quinn |
| 2004/0181175 A1 | 9/2004 | Clayman et al. |
| 2004/0193073 A1 | 9/2004 | DeMello et al. |
| 2004/0220516 A1 | 11/2004 | Solomon et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0267347 A1 | 12/2004 | Cervantes |
| 2005/0027249 A1 | 2/2005 | Reifart et al. |
| 2005/0055077 A1 | 3/2005 | Marco |
| 2005/0059930 A1 | 3/2005 | Garrison et al. |
| 2005/0059931 A1 | 3/2005 | Garrison et al. |
| 2005/0089670 A1 | 4/2005 | Large |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0234507 A1 | 10/2005 | Geske et al. |
| 2005/0244472 A1 | 11/2005 | Hughes et al. |
| 2005/0283221 A1 | 12/2005 | Mann et al. |
| 2006/0004323 A1 | 1/2006 | Chang et al. |
| 2006/0047261 A1 | 3/2006 | Joshi |
| 2006/0063973 A1 | 3/2006 | Makower et al. |
| 2006/0173382 A1 | 8/2006 | Schreiner |
| 2006/0189844 A1 | 8/2006 | Tien |
| 2006/0190022 A1 | 8/2006 | Beyar et al. |
| 2006/0211752 A1 | 9/2006 | Kohn et al. |
| 2006/0271024 A1 | 11/2006 | Gertner et al. |
| 2006/0284428 A1 | 12/2006 | Beadle et al. |
| 2007/0020196 A1 | 1/2007 | Pipkin et al. |
| 2007/0112358 A1 | 5/2007 | Abbott |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0269385 A1 | 11/2007 | Yun et al. |
| 2007/0282305 A1 | 12/2007 | Goldfarb et al. |
| 2007/0293727 A1 | 12/2007 | Goldfarb et al. |
| 2007/0293946 A1 | 12/2007 | Gonzales et al. |
| 2008/0015544 A1 | 1/2008 | Keith et al. |
| 2008/0033519 A1 | 2/2008 | Burwell et al. |
| 2008/0051804 A1 | 2/2008 | Cottler et al. |
| 2008/0097516 A1 | 4/2008 | Chang et al. |
| 2008/0103521 A1 | 5/2008 | Makower et al. |
| 2008/0119693 A1 | 5/2008 | Makower et al. |
| 2008/0125626 A1 | 5/2008 | Chang et al. |
| 2008/0132938 A1 | 6/2008 | Chang et al. |
| 2008/0172033 A1 | 7/2008 | Keith et al. |
| 2008/0183128 A1 | 7/2008 | Morriss et al. |
| 2008/0188803 A1 | 8/2008 | Jang |
| 2008/0188870 A1 | 8/2008 | Andre et al. |
| 2008/0195041 A1 | 8/2008 | Goldfarb et al. |
| 2008/0228085 A1 | 9/2008 | Jenkins et al. |
| 2008/0262508 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0030274 A1 | 1/2009 | Goldfarb et al. |
| 2009/0088728 A1 | 4/2009 | Dollar et al. |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0198216 A1 | 8/2009 | Muni et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0030031 A1 | 2/2010 | Goldfarb et al. |
| 2010/0042046 A1 | 2/2010 | Chang et al. |
| 2010/0087811 A1 | 4/2010 | Herrin et al. |
| 2010/0114066 A1 | 5/2010 | Makower et al. |
| 2010/0174138 A1 | 7/2010 | Chang et al. |
| 2010/0174308 A1 | 7/2010 | Chang et al. |
| 2010/0198191 A1 | 8/2010 | Clifford et al. |
| 2010/0198247 A1 | 8/2010 | Chang et al. |
| 2010/0198302 A1 | 8/2010 | Shalev |
| 2010/0210901 A1 | 8/2010 | Makower et al. |
| 2010/0268245 A1 | 10/2010 | Chang et al. |
| 2010/0274188 A1 | 10/2010 | Chang et al. |
| 2010/0290244 A1 | 11/2010 | Nath |
| 2010/0298862 A1 | 11/2010 | Chang et al. |
| 2011/0004057 A1 | 1/2011 | Goldfarb et al. |
| 2011/0015482 A1 | 1/2011 | Carrillo, Jr. |
| 2011/0060214 A1 | 3/2011 | Makower |
| 2011/0112512 A1 | 5/2011 | Muni et al. |
| 2011/0166190 A1 | 7/2011 | Anderson et al. |
| 2012/0071710 A1 | 3/2012 | Gazdzinski |
| 2012/0071824 A1 | 3/2012 | Chang et al. |
| 2012/0136207 A1 | 5/2012 | Goldfarb et al. |
| 2012/0184983 A1 | 7/2012 | Chang et al. |
| 2012/0245419 A1 | 9/2012 | Makower et al. |
| 2012/0265094 A1 | 10/2012 | Goldfarb et al. |
| 2013/0231529 A1 | 9/2013 | John et al. |
| 2013/0245608 A1 | 9/2013 | Muni et al. |
| 2013/0261388 A1 | 10/2013 | Jenkins et al. |

FOREIGN PATENT DOCUMENTS

| | | |
|---|---|---|
| CN | 2151720 | 1/1994 |
| CN | 2352818 | 12/1999 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 0200430 | 11/1986 |
| EP | 257605 | 3/1988 |
| EP | 355996 | 2/1990 |
| EP | 418391 | 3/1991 |
| EP | 427852 | 5/1991 |
| EP | 0515201 | 11/1992 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 0920882 | 6/1999 |
| EP | 0974936 | 1/2000 |
| EP | 1042998 | 10/2000 |
| EP | 1086664 | 3/2001 |
| EP | 1166710 | 1/2002 |
| EP | 1413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| JP | 53-67935 | 6/1978 |
| JP | 10-24098 | 1/1989 |
| JP | 3-503011 | 7/1991 |

(56) References Cited

FOREIGN PATENT DOCUMENTS

| | | |
|---|---|---|
| JP | 3-504935 | 10/1991 |
| JP | 4-221313 | 8/1992 |
| JP | 4-224766 | 8/1992 |
| JP | 5-503650 | 6/1993 |
| JP | 5-211985 | 8/1993 |
| JP | 6-277296 | 10/1994 |
| JP | 7-327916 | 12/1995 |
| JP | 8-317989 | 12/1996 |
| JP | 11-507251 | 6/1999 |
| JP | 2000-501634 | 2/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-507140 | 2/2003 |
| JP | 2003-062080 | 3/2003 |
| JP | 2003-521327 | 7/2003 |
| JP | 2004-357728 | 12/2004 |
| JP | 2005-532869 | 11/2005 |
| RU | 2213530 | 10/2003 |
| SU | 1662571 | 7/1991 |
| WO | WO 90/11053 | 10/1990 |
| WO | WO 90/14865 | 12/1990 |
| WO | WO 91/17787 | 11/1991 |
| WO | WO 92/15286 | 9/1992 |
| WO | WO 92/22350 | 12/1992 |
| WO | WO 94/12095 | 6/1994 |
| WO | WO 94/21320 | 9/1994 |
| WO | WO 95/02430 | 1/1995 |
| WO | WO 96/29071 | 9/1996 |
| WO | WO 97/21461 | 6/1997 |
| WO | WO 98/55174 | 12/1998 |
| WO | WO 99/00064 | 1/1999 |
| WO | WO 99/24106 | 5/1999 |
| WO | WO 99/26692 | 6/1999 |
| WO | WO 99/30655 | 6/1999 |
| WO | WO 99/32041 | 7/1999 |
| WO | WO 99/59649 | 11/1999 |
| WO | WO 00/09190 | 2/2000 |
| WO | WO 00/09192 | 2/2000 |
| WO | WO 00/23009 | 4/2000 |
| WO | WO 00/51672 | 9/2000 |
| WO | WO 00/53252 | 9/2000 |
| WO | WO 01/05462 | 1/2001 |
| WO | WO 01/45572 | 6/2001 |
| WO | WO 01/54558 | 8/2001 |
| WO | WO 01/56481 | 8/2001 |
| WO | WO 01/70325 | 9/2001 |
| WO | WO 01/74266 | 10/2001 |
| WO | WO 01/97895 | 12/2001 |
| WO | WO 02/062269 | 8/2002 |
| WO | WO 02/089899 | 11/2002 |
| WO | WO 03/049603 | 6/2003 |
| WO | WO 03/063703 | 8/2003 |
| WO | WO 03/105657 | 12/2003 |
| WO | WO 2004/006788 | 1/2004 |
| WO | WO 2004/018980 | 3/2004 |
| WO | WO 2004/026391 | 4/2004 |
| WO | WO 2004/082525 A2 | 9/2004 |
| WO | WO 2004/082525 A3 | 9/2004 |
| WO | WO 2005/018730 | 3/2005 |
| WO | WO 2005/077450 | 8/2005 |
| WO | WO 2005/089670 | 9/2005 |
| WO | WO 2005/117755 | 12/2005 |
| WO | WO 2006/034008 | 3/2006 |
| WO | WO 2006/078884 | 7/2006 |
| WO | WO 2006/107957 | 10/2006 |
| WO | WO 2006/116597 | 11/2006 |
| WO | WO 2006/118737 | 11/2006 |
| WO | WO 2006/135853 | 12/2006 |
| WO | WO 2007/035204 | 3/2007 |
| WO | WO 2007/111636 | 10/2007 |
| WO | WO 2007/124260 | 11/2007 |
| WO | WO 2008/036149 | 3/2008 |
| WO | WO 2008/045242 | 4/2008 |
| WO | WO 2008/051918 | 5/2008 |
| WO | WO 2008/134382 | 11/2008 |

OTHER PUBLICATIONS

Aust, R., et al. 'The Functional Size of the Human Maxillary Ostium in Vivo' Acta. Otolaryn. (9178) vol. 78 pp. 432-435.

Baim, D.S., MD 'Grossman's Cardiac Catheterization, Angiography, and Intervention' (2000) Lippincott Williams & Wilkins pp. 76, 84 & 214.

Barrett, S. 'Be Wary of Neurocranial Restructuring (NCR)' Chirobase; Jul. 2003; www.chirobase.org/06DD/ncr.html.

Bartal, N. 'An Improved stent for Use in the Surgical Management of Congenital Posterior Choanal Atresia' J. Laryngol. Otol (1988) vol. 102 pp. 146-147.

Becker, A.E. 'Restenosis After Angioplasty' The Lancet (1988) vol. 331, No. 8584 p. 532.

Bellis, M. History of the Catheter-Balloon Catheter—Thomas Fogarty. www.inventors.about.com/library/inventors/blcatheter.htm?p=1.

Benninger et al.; Adult Chronic Rhinosinusitis: Defintions, Diagnosis, Epidemiology, and Pathophysilogy Arch Otolaryngol Head and Neck Surg. vol. 129 (Sep. 2003) pp. A1-S32.

Bent et al. 'The Frontal Cell as a Cause of Frontal Sinus Obstruction' American Journal of Rhinology, vol. 8, No. 4 (1994) pp. 185-191.

Binner et al. 'Fibre-Optic Transillunination of the Sinuses: A Comparison of the Value of Radiography and Transillumination in Antral Disease' Clinical Otolaryngology. vol. 3 (1978) pp. 1-11.

Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.

Casiano et al. 'Endoscopic Lothrop Procedure: the University of Miami Experience' American Journal of Rhinology, vol. 12, No. 5 (1998) pp. 335-339.

Casserly, I.P. et al., Chapter 7. 'Guides and Wires in Percutaneous Coronary Intervention' Strategic Approaches in Coronary Intervention (2006) Lippincott Williams & Wilkins pp. 91-99.

Chien, Y.W. et al. 'Nasal Systemic Drug Delivery' Drugs and Pharmaceutical Sciences, vol. 39, pp. 60-63.

Cohen et al. 'Endoscopic Sinus Surgery: Where we are and where we're going' Current Opinion in Otolaryngology & Head and Neck Surgery, vol. 13 (2005) pp. 32-38.

Colla, A. et al., 'Trihaloacetylated Enol Ethers—General Synthetic Procedure and Heterocyclic Ring Closure Reactions with Hydroxylamine' Synthesis, (Jun. 1991) pp. 483-486.

Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue1, pp. 41-46.

Cussler, E.L. 'Diffusion: Mass transfer in Fluid Systems' Cambridge University Press (1996).

Davis, G.E. et al. 'A Complication from Neurocranial Restructuring' Arch Otolaryngol Head Neck Surg. vol. 129 (Apr. 2003) pp. 472-474.

Deutschmann, R. et al. 'A Contribution to the Topical Treatment of [Maxillary] Sinusitis Preliminary Communication' Stomat DDR 26, (1976) pp. 585-592.

Domb, A. et al. 'Handbook of Biodegradable Polymers' Harwood Academic Publishers (1997).

Doyle Nasal Splints, Jan. 25, 2007; www.doylemedical.com/nasalsplints.htm.

Draf, W. 'Endonasal Micro-Endoscopic Frontal Sinus Surgery: the Fulda Concept' Op Tech Otolaryngol Head Neck Surg. vol. 2 (1991) pp. 234-240.

Edmond, C. et al. 'ENT Surgical Stimulator' Nov. 1989.

ENT Checklist; Physical Examination Performance Checklist [date of publication unknown].

Eremychev, V.A. 'Needles for Puncture and Drainage of the Maxillary Sinus' Meditsinskaya Tekhnika, No. 5 (1974) pp. 54.55.

(56) References Cited

OTHER PUBLICATIONS

Feldman, R.L. et al., 'New Steerable, Ultra-Low-Profile, Fixed Wire Angioplasty Catheter: Initial Experience With the Cordis OrionTM Steerable PTCA Balloon Catheter' Cathet. Cardiovasc. Diagn. (1990) vol. 19, No. 2 pp. 142-145.
Ford, C.N. 'A Multipurpose Laryngeal Injector Device' Otolaryngol. Head Neck Surg. (1990) vol. 103, No. 1 pp. 135-137.
Friedman, M., M.D., et al. 'Frontal Sinus Surgery: Endoscopic Technique' Operative Techniques in Otolarynology—Head and Neck Surgery. vol. 12, No. 2 (Jun. 2001) pp. 60-65.
Friedman, et al. 'Intraoperative and Postoperative Assessment of Frontal Sinus Patency by Transillumination' Laryngoscope. vol. 110 (Apr. 2000) pp. 683-684.
Friedman, et al 'Middle Turbinate Medialization and Preservation in Endoscopic Surgery' Otolaryngology—Head and Neck Surgery. (2000) vol. 123, No. 1, part 1, pp. 76-80.
Fung, M.K.T. 'Template for Frontal Osteoplastic Flap' Laryngoscope. vol. 96 (1986) pp. 578-579.
Gatot, A. et al. 'Early treatment of Orbital Floor Fractures with Catheter Balloon in Children' Int J. Pediatric Otorhinolaryngol (1991) vol. 21 pp. 97-101.
Gerus, I.I. et al. 'β-Ethoxyvinyl Polyfluroroalkyl Ketones—Versatile Synthones in Fluoroorganic Chemistry' Journal of Fluorine Chemistry. vol. 69 (1994) pp. 195-198. Elesvier Science S.A.
Good, R.H. 'An Intranasal Method for Opening the Frontal Sinus Establishing the Largest Possible Drainage' Laryngoscope. vol. 18 (1908) pp. 266-274.
Gopferich 'Polymer Degradation and Erosion: Mechanisms and Application' Eur. J. Parm. Biophar. vol. 42 (1996) pp. 1-11.
Gorlov, D.V. et al 'Acylation of 2-Methoxypropene with Anhydrides and Halides of Perflurocarboxylic Acids in the Presence of Teriary Amines' Russian Chemical Bulletin. vol. 48 No. 9 (Sep. 1999) pp. 1791-1792. Kluwer Academic/Plenum Publishers.
Gottmann, et al. 'Balloon Dilatation in the Nasal Cavity and Paranasal Sinuses' CIRSE. (Sep. 25, 2004) pp. 1-27.
Gottmann, et al. 'Balloon Dilatation of Recurrent Ostial Occlusion of the Frontal Sinus' CIRSE Abstract (Mar. 2001) B-04353.
Gottman, et al., Balloon Dilatation of Recurrent Ostial Occlusion of the Front Sinus OASIS—Online Abstract Submission and Invitation System, 1996-2006, Coe Truman Technologies, Inc.
Gottmann, et al. 'Successful Treatment of Recurrent Post-Operative Frontal Sinus Stenoses by Balloon Dilatation' CIRSE. (Oct. 5, 2002).
Gottmann, D. 'Treatment of Stenoses of Upper Air Routes by Balloon Dilation' Proceeding of the 83rd Annual Convention of Association of West German ENT Physicians (1999).
Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.
Hashim, et al. 'Balloon Compression of the Intermaxillary Sinus for Intractable Post Traumatic Bleeding from the Maxillary Artery' Scandinavian Journal of Plastic and reconstruction Sergery and Hand Surgery (1999) vol. 33 pp. 321-324.
Hojo, M. et al, 'Electrophilic Substiutions of Olefinic Hydrogens II. Acylation of Vinyle Ethers and N Vinyl Amides Chemistry Letters' (1976) pp. 499-502. Chemical Society of Japan.
Hopf, J.U.G. et al. 'Minature Endoscopes in Otorhinolaryngologic Applications' Min Invas Ther & Allied Technol. (1998) vol. 7, No. 3 pp. 209-218.
Hosemann, W. et al. A Dissection Course on Endoscopic Endonasal Sinus Surgery (2005) Endo-Press, Tuttlingen pp. 4-37.
Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.
Hosemann, M.E. et al. 'Experimentelle Untersuchungen sur Wundheilung in den Nasennebenholhlen. II. Spontaner Wundschluss und medikamentose Effekte im standardisierten Wundmodell.' HNO 39 (1991) pp. 48-54. 'Experimental investigations on wound healing of the paranasal sinuses. II. Spontaneous wound closure and pharmacological effects in a standardized animal model.' HNO 39 (1991) pp. 48-54.
Hosemann, W.G. et al. 'Minimally Invasive Endonasal Sinus Surgery' Thieme, Stuttgart, New York (2000).
Hosemann, M.E. et al. 'Normal Wound Healing of the Paranasal Sinuses—Clinical and Experimental Investigations' Eur Arch Otorhinolarygol. vol. 248, (1991) pp. 390-394.
Hosemann, W. et al. 'Behandlung nach Nasennebenhohleneingriffen, part 2: Theapeutische Maβnahem' HNO akutell 7 (1999) pp. 291-302.
Hospital Corpsman Sickcall Screener's Handbook. Naval Hospital Great Lakes (Apr. 1999) www.brooksidepress.org/Products/Operationa.Medicine/DATA. 2001 pp. 1-6.
Hybels, R.L. 'Transillumination Durning Osteoplastic Frontal Sinusotomy' The Laryngoscope. vol. 91 (Sep. 1981) pp. 1560.
Ijaduola, T.G.A. 'Use of a Foley Catheter for Short-Tenn Drainage in Frontal Sinus Surgery' Ther Journal of Laryngology and Otology. (1989) vol. 103. pp. 375.378.
Ingals, E.F. 'New Operation and Instruments for Draining the Frontal Sinus' Ann. Otol. Rhinol. Layyngol. vol. 14 (1905) pp. 644-649.
Iro, H. et al., 'A New Device for Frontal Sinus Endoscopy: First Clinical Report' Otolaryngol. Head Neck Surg. (2001) vol. 125 No. 6 pp. 613-616.
Jacobs, J.B. '100 Years of Frontal Sinus Surgery' Laryngoscope. vol. 107 (1997) pp. 1-36.
K-Splint Internal Nasal Splints; Jan. 25, 2007; www.invotec.net/rhinology/ksplint.html.
Kaiser, H. et al 'Cortizontherapie, Corticoide in Klinik und Praxis' Thieme, Stuggart (1992) pp. 390-401.
Kennedy, D.W., M.D. et al. 'Diseases of the Sinuses: Diagnosis and Management' (Copyright 2001) by B.C. Decker Inc.
Khomutov, S.M. et al. 'Dissolution of a Mixture of Steroids in Cyclodextrin Solutions: a Model Description' Pharmaceutical Chemistry Journal. vol. 35, No. 11 (Nov. 2001) pp. 627-629.
Kingdom, T.T. et al. 'Image-Guided Surgery of the Sinuses: Current Technology and Applications' Otolaryngol. Clin. North Am. vol. 37, No. 2 (Apr. 2004) pp. 381-400.
Klossek, J.M. et al. 'Local Safety of Intranasal Trimcinolone Acentonide: Clinical and Histological Aspects of Nasal Mucosa in the Long-Term Treatment of Perennial Allergic Rhinitis' Rhinology. vol. 39, No. 1 (2001) pp. 17-22.
Kozlov et al. 'Diagnosis and Treatment of Sinusitis by YAMIK Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology—Head and Neck Surgery. vol. 2, No. 4 (1991) pp. 226-231.
Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. (1995) vol. 6, No. 5 pp. 711-713.
Lanza, D.C. 'Postoperative Care and Avoiding Frontal Recess Stenosis' Internatinal Advanced Sinus Symposium Jul. 21-24, 1993.
Large, G.C. 'Crystalline Tetracycline Hydrochloride in the Treatment of Acute and Chronic Maxillary Sinusitis' Canad. M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-192.
Medtronic, xomed.com—MicroFrance Catalog Browser. www.xomcatcom/xomfrance/index.php?zone=both&cat=18&sub=58&prodline=1272 (Dec. 31, 2003) pp. 1-2.
Mehan, V.K. et al., 'Coronary Angioplasty through 4 French Diagnostic Catheters' Cathet. Cardiovasc. Diagn. (1993) vol. 30, No. 1 pp. 22-26.

(56) References Cited

OTHER PUBLICATIONS

Mellor, J.M. et al 'Synthesis of Trifluromethylnaphthalenes' Tetrahedron. vol. 56 (2000) pp. 10067-10074. Elsevier Science Ltd.
Metson, R., et al., 'Endoscopic Treatment of Sphenoid Sinusitis' Otolaryngol. Head Neck Surg. (1996) vol. 114, No. 6 pp. 736-744.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Miller, et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523.3528. American Chemical Society.
Nasal Surgery and Accessories, Jan. 25, 2007; www.technologyforlife.com.au/ent/nasal.html.
Park, K. et al. 'Biodegradable Hydrogels for Durg Delivery' (1993) Technomic Publishing Inc. Lancaster.
Piccirillo, J.F. et al. 'Physchometric and Clinimetric Validity of the 20-Item Sino-Nasal Outcome test (SNOT-20)' Copyright 1996 Washington University, St. Louis, MO.
Piers, et al. 'A Flexible Distal Tip with Two Degrees of Freedom for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' Texas State Journal of Medicine (May 1952) pp. 281-288.
St. Croix et al. 'Genes Expressed in Human Tumor Endothelium' Science, vol. 289 (May 15, 2000) pp. 1197-1202.
Sama, A., et al., 'Current Opinions on the Surgical Management of Frontal Sinus Disease' ENT News. www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluropscopic Guidance' Catheter Cardiovasc. Interv. (2001) vol. 52 No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Schneider. Pfizer Ad for Softip [date of publication unknown].
Shah, N.J. et al., 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at bhj.org/journal/1999_4104_oct99/sp_659.htm.
Single-Pole and Multi-Pole Lightguides for UV Spot Light Curing Systems.
Sinusitis, Maxillary, Acute Surgical Treatment. Http://www.emedicine.com/ent/topic340.htm. Aug. 29, 2006. pp. 1-11.
Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.
Stammberger, H. 'Komplikationen entzundlicher Nasennebenhohlenerkrankungen eischließ iatrogen bedingter Komplikationen' Eur Arch Oti-Rhino-Laryngol Supple. (Jan. 1993) pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.
Strohm, et al. Die Behandlung von Stenosen der oberen Luftwege mittels rontgenologisch gesteuerter Ballondilation (Sep. 25, 1999) pp. 1-4.
Strohm, et al 'Le Traitement Des Stenoses Voies Aeriennes Superieures Par Dilation Ay Balloon' Sep. 25, 1999.
Strohm, et al. 'Treatment of Stenoses of the Upper Airways by Balloon Dilation' Sudwestdeutscher Abstract 45 (Sep. 25, 1999) pp. 1-3.
SurgTrainer Product Information 2003, Surg Trainer, Ltd. Ibaraki, Japan.
SurgTrainer Product Information 'Incisive Human Nasal Model for ESS Training' Surg Trainer, Ltd. Ibaraki, Japan (2004) www1.accsnet.ne.jp/~juliy/st/en/partslist.html.
Tabor, M.H. et al., 'Symptomatic Bilateral Duct Cysts in a Newborn-Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
Terumo. Medi-Tech. Boston Scientific. (1993) Ad of Glidewire.
The Operating Theatre Journal (www.otjonline.com) 'Disposable Medical Device for Wound Disclosure/The Tristel Purple Promotion—A Collaboration between Tristel PLC and Karl Storz Ednoscopy (UK) Ltd.' p. 4.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steriod Distribution' Rhinology. vol. 37 (1999) pp. 69-73.
Weiner, R.I., D.O., et al., 'Development and Application of Transseptal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow. [date of publication unknown].
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying poster presentation.
Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low Profile monorail Balloon Catheter' Cathet. Cardiovasc. Diagn. (1994) vol. 33, No. 1, pp. 76-79.
Australian Office Action, Examiners First Report dated Apr. 8, 2010 for Application No. AU 2005274794.
Australian Office Action, Examiners First Report dated Dec. 9, 2011 for Application No. AU 2006292818.

(56) References Cited

OTHER PUBLICATIONS

Chinese Office Action, First Office Action dated Nov. 5, 2012 for CN 200980137396.1.
Chinese Search Report dated Oct. 29, 2012 for Application No. CN 200980137396.1.
Chinese Search Report dated Jan. 11, 2013 for Application No. CN 200980152995.0.
Chinese Office Action, First Office Action dated Jan. 29, 2013 for CN 200980152995.1.
European Communication dated Sep. 4, 2008 for Application No. EP 05773189.
European Communication dated Jun. 19, 2009 for Application No. EP 05773189.
European Communication dated Aug. 1, 2012 for Application No. EP 06784759.0.
European Communication dated Aug. 24, 2012 for Application No. EP 05798331.4.
European Communication dated Nov. 9, 2012 for Application No. EP 07750248.2.
European Communication dated Apr. 19, 2012 for Application No. EP 08746715.5.
European Communication dated Jan. 7, 2013 for Application No. EP 08746715.5.
European Communication dated Apr. 11, 2013 for Application No. EP 05778834.1.
European Communication dated May 10, 2013 for Application No. EP 06751637.7.
European Exam Report dated Feb. 22, 2006 for Application No. EP 02716734.5.
European Exam Report dated Feb. 8, 2007 for Application No. EP 02716734.5.
European Search Report and Written Opinion dated Sep. 11, 2009 for Application No. EP 06815174.
European Search Report dated Mar. 16, 2010 re Application No. EP 06718986.
European Search Report dated Sep. 27, 2011 for Application No. EP 10182961.
European Search Report dated Sep. 29, 2011 for Application No. EP 10182893.
European Search Report dated Jul. 23, 2012 for Application No. EP 12162709.
European Search Report dated Jul. 24, 2012 for Application No. EP 12162712.
European Search Report dated Aug. 31, 2012 for Application No. EP 12173295.
European Search Report dated Oct. 10, 2012 for Application No. EP 12175607.
European Search Report dated Nov. 22, 2012 for Application No. EP 12182993.
European Search Report dated Dec. 5, 2012 for Application No. EP 12182998.
European Search Report dated Jan. 9, 2013 for Application No. EP 12183000.
European Search Report dated Jan. 11, 2013 for Application No. EP 12183002.
European Search Report dated Aug. 13, 2013 for Application No. EP 13172140.
European Search Report dated Sep. 9, 2013 for Application No. EP 13179223.
Partial European Search Report dated Sep. 20, 2007 for Application No. EP 07252018.
Partial European Search Report dated Mar. 25, 2008 for Application No. EP 07252018.
Supplemental Partial European Search Report dated Jun. 2, 2008 for Application No. EP 05773189.
Supplemental Partial European Search Report dated Jul. 1, 2009 for Application No. EP 06815285.
Supplemental Partial European Search Report dated Nov. 19, 2010 for Application No. EP 06751637.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.
Supplemental European Search Report dated Mar. 16, 2010 for Application No. EP 06718986.
Supplemental European Search Report dated Jun. 22, 2010 for Application No. EP 06784759.
Supplemental European Search Report dated Sep. 23, 2010 for Application No. EP 08746715.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 29, 2011 for Application No. EP 07750248.
PCT Search Report dated Nov. 30, 2009 for Application No. UPCT/US2009/057203.
International Preliminary Report on Patentability dated Aug. 7, 2006 for Application No. PCT/US05/25371.
International Preliminary Report on Patentability and Written Opinion dated Sep. 25, 2007 for Application No. PCT/US06/002004.
International Preliminary Report on Patentability dated Feb. 15, 2008 for Application No. PCT/US05/13617.
International Preliminary Report on Patentability and Written Opinion dated Nov. 18, 2008 for Application No. PCT/US07/11449.
International Preliminary Report on Patentability and Written Opinion dated Apr. 7, 2009 for Application No. PCT/US07/021170.
International Preliminary Report on Patentability and Written Opinion dated May 5, 2009 for Application No. PCT/US06/036960.
International Preliminary Report on Patentability and Written Opinion dated Oct. 13, 2009 for Application No. PCT/US08/059786.
International Preliminary Report on Patentability and Written Opinion dated Oct. 27, 2009 for Application No. PCT/US08/061343.
International Preliminary Report on Patentability dated Jun. 29, 2011 for Application No. PCT/US2009/069143.
International Search Report dated Jun. 3, 2002 for Application No. PCT/EP02/01228.
International Search Report and Written Opinion dated Apr. 10, 2006 for Application No. PCT/US05/25371.
International Search Report dated May 8, 2007 for Application No. PCT/US2006/16026.
International Search Report dated Aug. 17, 2007 for Application No. PCT/US05/013617.
International Search Report dated Aug. 29, 2007 for Application No. PCT/US06/002004.
International Search Report dated Sep. 25, 2007 for Application No. PCT/US06/037167.
International Search Report dated Oct. 19, 2007 for Application No. PCT/US07/003394.
International Search Report dated May 29, 2008 for Application No. PCT/US07/021170.
International Search Report dated May 29, 2008 for Application No. PCT/US07/021922.
International Search Report dated Jul. 1, 2008 for Application No. PCT/US06/022745.
International Search Report dated Jul. 3, 2008 for Application No. PCT/US2006/029695.
International Search Report dated Jul. 7, 2008 for Application No. PCT/US07/016213.
International Search Report dated Jul. 8, 2008 for Application No. PCT/US07/011474.
International Search Report dated Jul. 17, 2008 for Application No. PCT/US06/036960.
International Search Report and Written Opinion dated Jul. 21, 2008 for Application No. PCT/US05/033090.

(56) References Cited

OTHER PUBLICATIONS

International Search Report dated Aug. 25, 2008 for Application No. PCT/US2008/000911.
International Search Report dated Sep. 10, 2008 for Application No. PCT/US07/016212.
International Search Report and Written Opinion dated Sep. 12, 2008 for Application No. PCT/US07/16214.
International Search Report and Written Opinion dated Sep. 17, 2008 for Application No. PCT/US08/059786.
International Search Report and Written Opinion dated Sep. 17, 2008 for Application No. PCT/US08/061343.
International Search Report and Written Opinion dated Oct. 1, 2008 for Application No. PCT/US07/011449.
International Search Report dated Oct. 15, 2008 for Application No. PCT/US2008/061048.
International Search Report dated Nov. 30, 2009 for Application No. PCT/US2009/057203.
International Search Report dated Dec. 10, 2009 for Application No. PCT/US2009/052236.
International Search Report dated Dec. 16, 2009 for Application No. PCT/US2009/050800.
International Search Report dated Mar. 31, 2010 for Application No. PCT/US2009/069143.
International Search Report dated Jul. 8, 2010 for Application No. PCT/US2010/027837.
International Search Report and Written Opinion dated Oct. 6, 2010 for Application No. PCT/US2010/040548.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
International Search Report dated Mar. 31, 2011 for Application No. PCT/US2009/069143.
International Search Report dated Aug. 9, 2011 for Application No. PCT/US2011/038751.
International Search Report dated May 18, 2012 for Application No. PCT/US2011/052321.
Partial International Search Report dated Feb. 7, 2012 for Application No. PCT/US2011/052321.
Japanese Office Action, Examiner's Decision of Refusal dated Oct. 18, 2011 for Application No. JP 2007-509632.
Japanese Office Action, Notification of Reasons for Refusal dated Apr. 26, 2011 for Application No. JP 2007-532485.
Japanese Office Action, Notification of Reasons for Refusal dated Jan. 24, 2012 for Application No. JP 2007-532485.
Japanese Office Action, Notification of Reasons for Refusal dated Aug. 16, 2011 for Application No. JP 2008-516013.
Japanese Office Action, Notification of Reasons for Refusal dated Nov. 8, 2011 for Application No. JP 2008-524250.
Japanese Office Action, Notification of Reasons for Refusal dated Jun. 25, 2013 for Application No. JP 2012-131840.
Russian Office Action dated Sep. 28, 2012 for Application No. RU 2011130530.
Russian Office Action dated Mar. 19, 2013 for Application No. RU 2011130530.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.
USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
USPTO Office Action dated Dec. 29, 2008 for U.S. Appl. No. 11/193,020.
USPTO Office Action dated May 13, 2009 for U.S. Appl. No. 11/193,020.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
U.S. Appl. No. 11/648,158, filed Dec. 29, 2006.
U.S. Appl. No. 11/789,705, filed Apr. 24, 2007.
U.S. Appl. No. 11/804,308, filed May 16, 2007.

(56) References Cited

OTHER PUBLICATIONS

U.S. Appl. No. 11/804,309, filed May 16, 2007.

U.S. Appl. No. 13/840,430, filed Mar. 15, 2013.
English Machine Translation for JP 5-503650.

\* cited by examiner

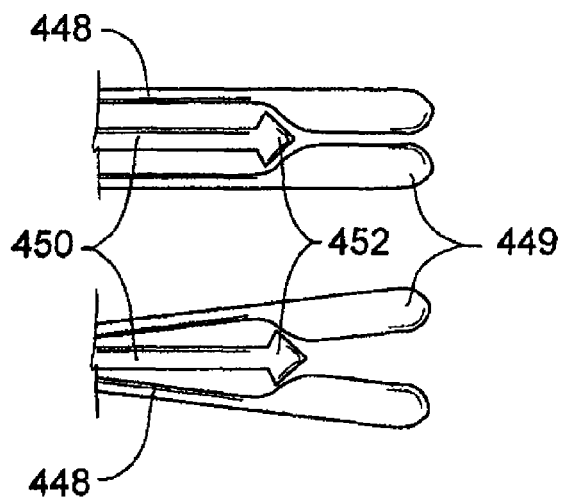
Fig. 4L
Fig. 4M
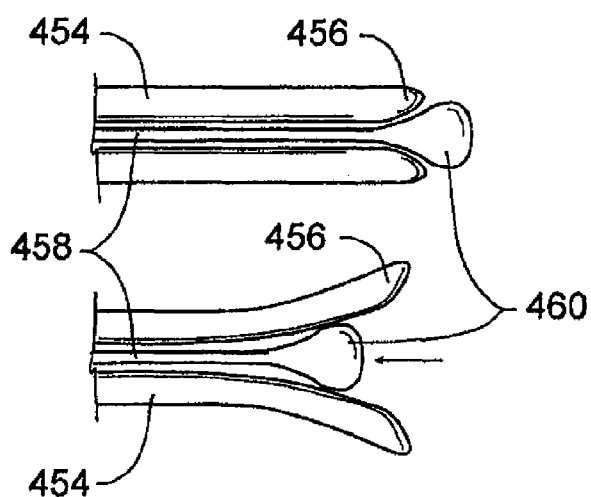
Fig. 4N
Fig. 4O
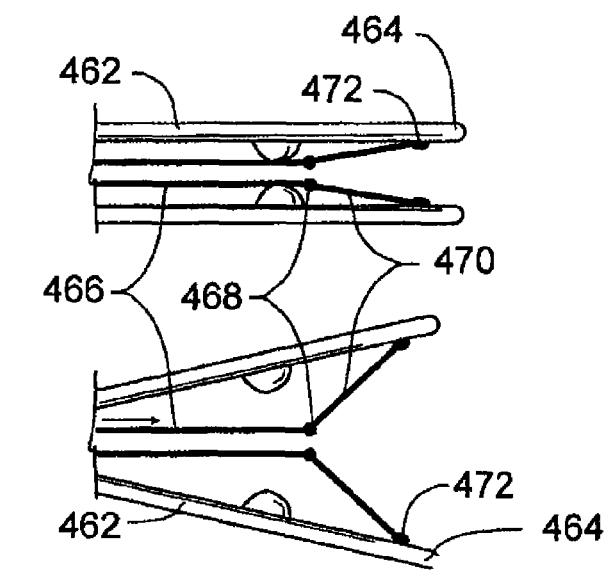
Fig. 4P
Fig. 4Q

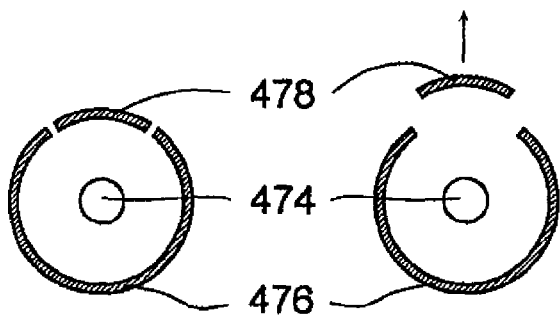 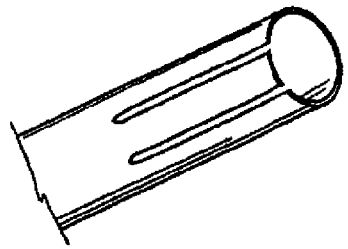
*Fig. 4R*  *Fig. 4S*  *Fig. 4S'*
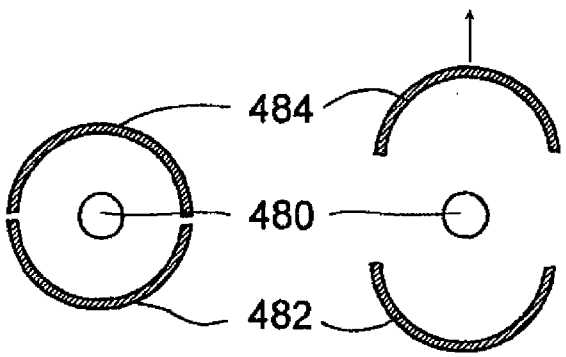 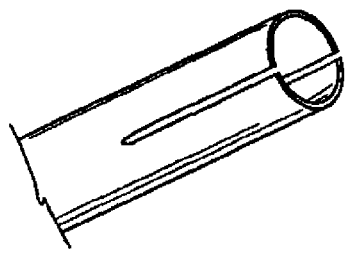
*Fig. 4T*  *Fig. 4U*  *Fig. 4U'*
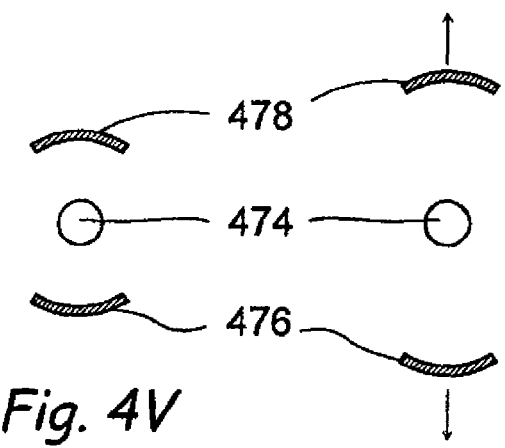 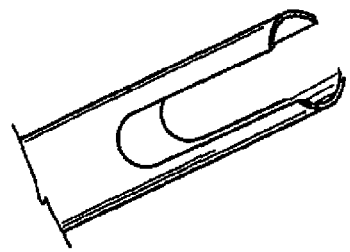
*Fig. 4V*  *Fig. 4W*  *Fig. 4W'*

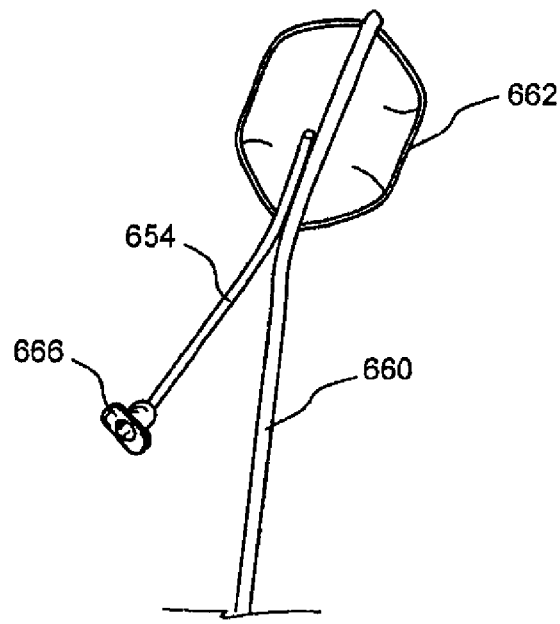
*Fig. 6 N*
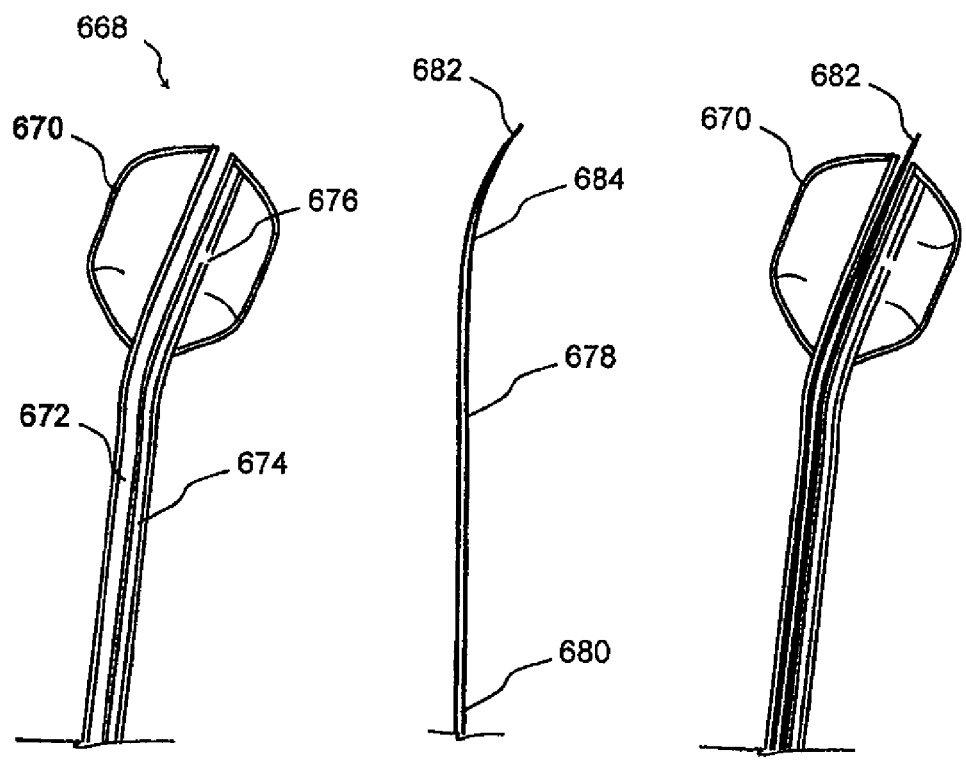
*Fig. 6 O*   *Fig. 6 P*   *Fig. 6 Q*

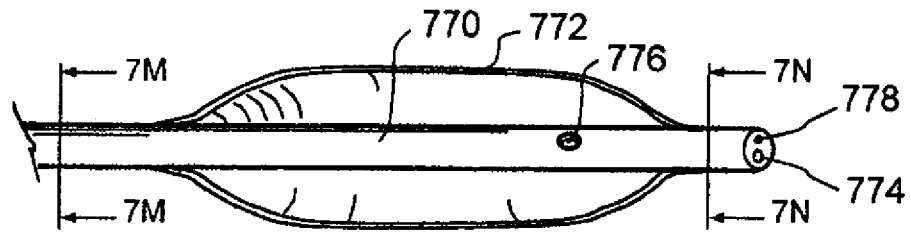
*Fig. 7L*
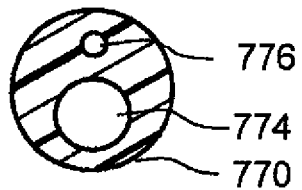
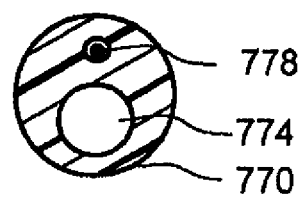
*Fig. 7M*  *Fig. 7N*
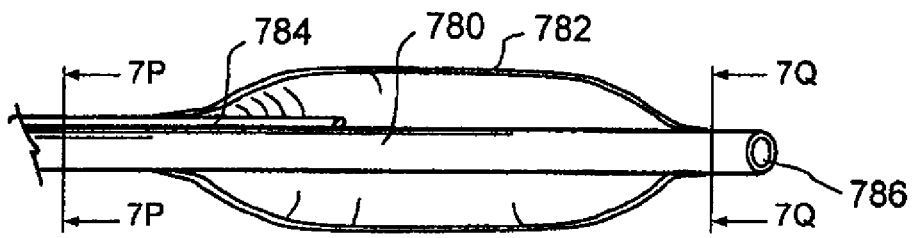
*Fig. 7O*
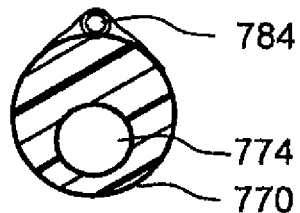
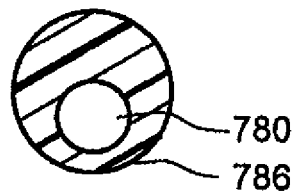
*Fig. 7P*  *Fig. 7Q*

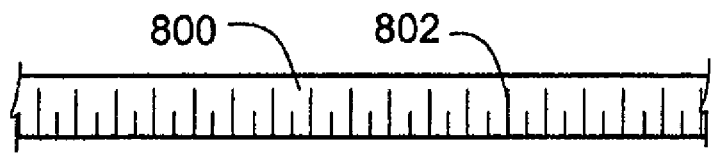
*Fig. 8A*
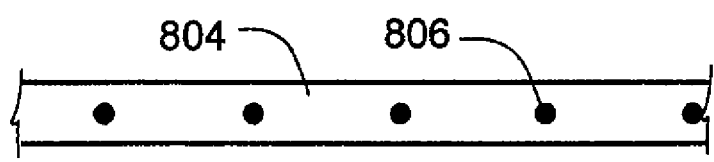
*Fig. 8B*
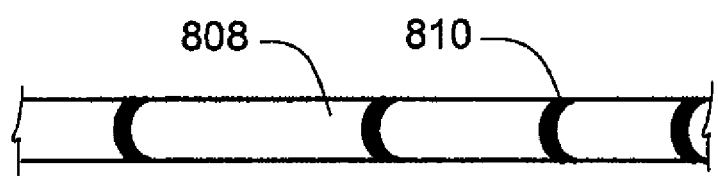
*Fig. 8C*
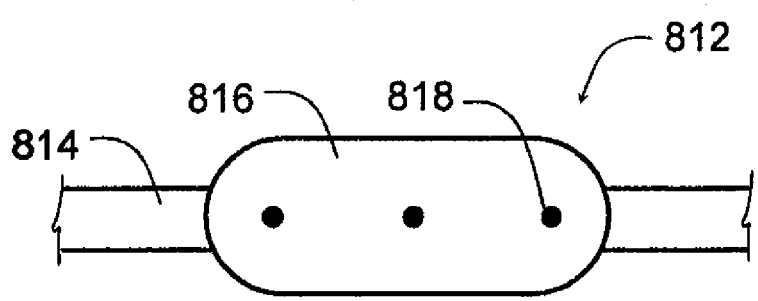
*Fig. 8D*
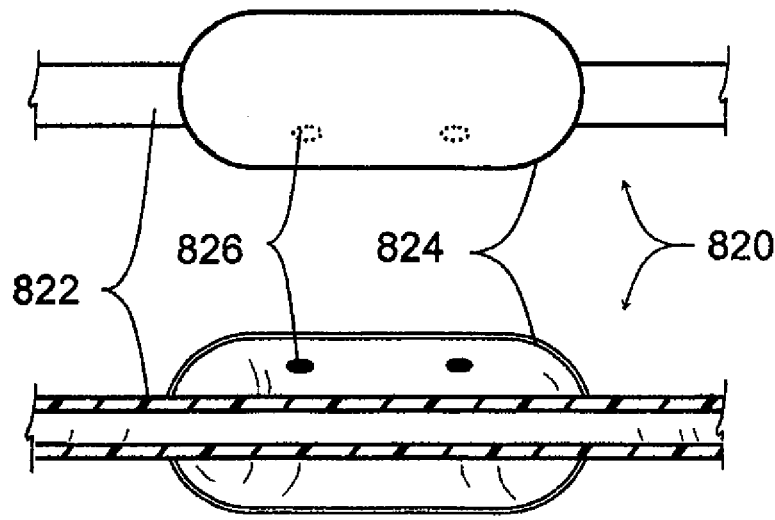
*Fig. 8E*
*Fig. 8E'*

APPARATUS AND METHODS FOR DILATING AND MODIFYING OSTIA OF PARANASAL SINUSES AND OTHER INTRANASEL OR PARANASAL STRUCTURES

RELATED APPLICATION

This patent application is a continuation of U.S. patent application Ser. No. 12/768,963 entitled Apparatus and Methods for Dilating and Modifying Ostia of Paranasal Sinuses and Other Intranasal or Paranasal Structures filed Apr. 28, 2010, which is a continuation of U.S. patent application Ser. No. 11/928,346, entitled Apparatus and Methods for Dilating and Modifying Ostia of Paranasal Sinuses and Other Intranasal or Paranasal Structures filed on Oct. 30, 2007, and now issued as U.S. Pat. No. 8,172,828, which is a continuation of U.S. patent application Ser. No. 10/944,270 entitled Apparatus and Methods for Dilating and Modifying Ostia of Paranasal Sinuses and Other Intranasal or Paranasal Structures filed on Sep. 17, 2004, and now abandoned, which is a continuation-in-part of U.S. patent application Ser. No. 10/829,917 entitled Devices, Systems and Methods for Diagnosing and Treating Sinusitis and Other Disorders of the Ears, Nose and/or Throat filed Apr. 21, 2004 and now issued as U.S. Pat. No. 7,654,997, the entire disclosure of each such patent and patent application being expressly incorporated herein by reference.

FIELD OF THE INVENTION

The present invention relates generally to medical devices and methods and more particularly to minimally invasive, devices, systems and methods for treating sinusitis and other ear, nose & throat disorders.

BACKGROUND

The nose is responsible for warming, humidifying and filtering inspired air and for conserving heat and moisture from expired air. The nose is formed mainly of cartilage, bone, mucous membranes and skin.

The bones in the nose contain a series of cavities known as paranasal sinuses that are connected by passageways. The paranasal sinuses include frontal sinuses, ethmoid sinuses, sphenoid sinuses and maxillary sinuses. The paranasal sinuses are lined with mucous-producing epithelial tissue and ultimately opening into the nasal cavity. Normally, mucous produced by the epithelial tissue slowly drains out of each sinus through an opening known as an ostium. If the epithelial tissue of one of these passageways becomes inflamed for any reason, the cavities which drain through that passageway can become blocked. This blockage can be periodic (resulting in episodes of pain) or chronic. This interference with drainage of mucous (e.g., occlusion of a sinus ostium) can result in mucosal congestion within the paranasal sinuses. Chronic mucosal congestion of the sinuses can cause damage to the epithelium that lines the sinus with subsequent decreased oxygen tension and microbial growth (e.g., a sinus infection).

Sinusitis:

The term "sinusitis" refers generally to any inflammation or infection of the paranasal sinuses caused by bacteria, viruses, fungi (molds), allergies or combinations thereof. It has been estimated that chronic sinusitis (e.g., lasting more than 3 months or so) results in 18 million to 22 million physician office visits per year in the United States. Patients who suffer from sinusitis typically experience at least some of the following symptoms:

- headaches or facial pain
- nasal congestion or post-nasal drainage
- difficulty breathing through one or both nostrils
- bad breath
- pain in the upper teeth Thus, one of the ways to treat sinusitis is by restoring the lost mucous flow. The initial therapy is drug therapy using anti-inflammatory agents to reduce the inflammation and antibiotics to treat the infection. A large number of patients do not respond to drug therapy. Currently, the gold standard for patients with chronic sinusitis that do not respond to drug therapy is a corrective surgery called Functional Endoscopic Sinus Surgery.

Current and Proposed Procedures for Sinus Treatment

Functional Endoscopic Sinus Surgery

In FESS, an endoscope is inserted into the nose and, under visualization through the endoscope, the surgeon may remove diseased or hypertrophic tissue or bone and may enlarge the ostia of the sinuses to restore normal drainage of the sinuses. FESS procedures are typically performed with the patient under general anesthesia.

Although FESS continues to be the gold standard therapy for surgical treatment of severe sinus disease, FESS does have several shortcomings. For example, FESS can cause significant post-operative pain. Also, some FESS procedures are associated with significant postoperative bleeding and, as a result, nasal packing is frequently placed in the patient's nose for some period of time following the surgery. Such nasal packing can be uncomfortable and can interfere with normal breathing, eating, drinking etc. Also, some patients remain symptomatic even after multiple FESS surgeries. Additionally, some FESS procedures are associated with risks of iatrogenic orbital, intracranial and sinonasal injury. Many otolaryngologists consider FESS an option only for patients who suffer from severe sinus disease (e.g., those showing significant abnormalities under CT scan). Thus, patients with less severe disease may not be considered candidates for FESS and may be left with no option but drug therapy. One of the reasons why FESS procedures can be bloody and painful relates to the fact that instruments having straight, rigid shafts are used. In order to target deep areas of the anatomy with such straight rigid instrumentation, the physician needs to resect and remove or otherwise manipulate any anatomical structures that may lie in the direct path of the instruments, regardless of whether those anatomical structures are part of the pathology.

Balloon Dilation Based Sinus Treatment

Methods and devices for sinus intervention using dilating balloons have been disclosed in U.S. Pat. No. 2,525,183 (Robison) and United States Patent Publication No. 2004/0064150 A1 (Becker). For example, U.S. Pat. No. 2,525,183 (Robison) discloses an inflatable pressure device which can be inserted following sinus surgery and inflated within the sinus. The patent does not disclose device designs and methods for flexibly navigating through the complex nasal anatomy to access the natural ostia of the sinuses. The discussion of balloon materials is also fairly limited to thin flexible materials like rubber which are most likely to be inadequate for dilating the bony ostia of the sinus.

United States patent publication number 2004/0064150 A1 (Becker) discloses balloon catheters formed of a stiff hypotube to be pushed into a sinus. The balloon catheters have a stiff hypotube with a fixed pre-set angle that enables them to be pushed into the sinus. In at least some procedures wherein it is desired to position the balloon catheter in the ostium of a paranasal sinus, it is necessary to advance the balloon catheter through complicated or tortuous anatomy in order to properly position the balloon catheter within the desired sinus ostium. Also, there is a degree of individual variation in the intranasal and paranasal anatomy of human beings, thus making it difficult to design a stiff-shaft balloon catheter that is optimally shaped for use in all individuals. Indeed, rigid catheters formed of hypotubes that have pre-set angles cannot be easily adjusted by the physician to different shapes to account for individual variations in the anatomy. In view of this, the Becker patent application describes the necessity of having available a set of balloon catheters, each having a particular fixed angle so that the physician can select the appropriate catheter for the patient's anatomy. The requirement to test multiple disposable catheters for fit is likely to be very expensive and impractical. Moreover, if such catheter are disposable items (e.g., not sterilizable and reusable) the need to test and discard a number of catheters before finding one that has the ideal bend angle could be rather expensive.

Thus, although the prior art discloses the use of dilating balloons for sinus treatments, it does not disclose the various means for navigation through the complex anatomy without significant manipulation of non-pathogenic anatomical regions that obstruct direct access to the sinus openings. Further, the prior art only discloses balloons of relatively simple shapes or materials for dilating sinus openings. Further, this art does not sufficiently elaborate beyond endoscopy on other means for imaging or tracking the position of such devices within the sinus anatomy.

Thus, there is a need for new devices and methods for easily navigating the complex anatomy of the nasal cavities and paranasal sinuses and for treating disorders of the paranasal sinuses with minimal complications due to individual variations in anatomy and causing minimal trauma to or disruption of anatomical structures that are not pathogenic.

SUMMARY OF THE INVENTION

In general, the present invention provides methods, devices and systems for diagnosing and/or treating sinusitis or other conditions of the ear, nose or throat.

In accordance with the present invention, there are provided methods wherein one or more flexible or rigid elongate devices as described herein are inserted in to the nose, nasopharynx, paranasal sinus, middle ear or associated anatomical passageways to perform an interventional or surgical procedure. Examples of procedures that may be performed using these flexible catheters or other flexible elongate devices include but are not limited to: remodeling or changing the shape, size or configuration of a sinus ostium or other anatomical structure that affects drainage from one or more paranasal sinuses; cutting, ablating, debulking, cauterizing, heating, freezing, lasing, forming an osteotomy or trephination in or otherwise modifying bony or cartilaginous tissue within paranasal sinus or elsewhere within the nose; removing puss or aberrant matter from the paranasal sinus or elsewhere within the nose; scraping or otherwise removing cells that line the interior of a paranasal sinus; delivering contrast medium; delivering a therapeutically effective amount of a therapeutic substance; implanting a stent, tissue remodeling device, substance delivery implant or other therapeutic apparatus; cutting, ablating, debulking, cauterizing, heating, freezing, lasing, dilating or otherwise modifying tissue such as nasal polyps, abberant or enlarged tissue, abnormal tissue, etc.; grafting or implanting cells or tissue; reducing, setting, screwing, applying adhesive to, affixing, decompressing or otherwise treating a fracture; delivering a gene or gene therapy preparation; removing all or a portion of a tumor; removing a polyp; delivering histamine, an allergen or another substance that causes secretion of mucous by tissues within a paranasal sinus to permit assessment of drainage from the sinus; implanting a cochlear implant or indwelling hearing aid or amplification device, etc.

Still further in accordance with the invention, there are provided devices and systems for performing some or all of the procedures described herein. Introducing devices may be used to facilitate insertion of working devices (e.g. catheters e.g. balloon catheters, tissue cutting or remodeling devices, guidewires, devices for implanting elements like stents, electrosurgical devices, energy emitting devices, devices for delivering diagnostic or therapeutic agents, substance delivery implants, scopes etc) into the paranasal sinuses and other structures in the ear, nose or throat.

Still further in accordance with the invention, there are provided apparatus and methods for navigation and imaging of the interventional devices within the sinuses using endoscopic including stereo endoscopic, fluoroscopic, ultrasonic, radiofrequency localization, electromagnetic, magnetic and other radiative energy based modalities. These imaging and navigation technologies may also be referenced by computer directly or indirectly to pre-existing or simultaneously created 3-D or 2-D data sets which help the doctor place the devices within the appropriate region of the anatomy.

Further aspects, details and embodiments of the present invention will be understood by those of skill in the art upon reading the following detailed description of the invention and the accompanying drawings.

BRIEF DESCRIPTION OF THE DRAWINGS

FIGS. 2Y through 2AC are partial coronal sectional views through a human head showing various steps of a method for treating a mucocele in a frontal sinus.

FIGS. 4L and 4M show sectional views of a mechanical dilator that comprises a pushable member.

FIGS. 4N and 4O show sectional views of a mechanical dilator that comprises a pullable member.

FIGS. 4P and 4Q show sectional views of a mechanical dilator that comprises a hinged member.

FIGS. 4R through 4W' are schematic diagrams of alternative configurations for the distal portions of mechanical dilators of the types shown in FIGS. 4H through 4Q.

FIG. 5O shows a partial perspective view of a balloon catheter device comprising a balloon for delivering diagnostic or therapeutic substances.

FIG. 5P shows a partial perspective view of a balloon/cutter catheter device comprising a balloon with one or more cutter blades.

FIG. 5Q shows a perspective view of a balloon catheter device comprising a balloon with a reinforcing braid attached on the external surface of the balloon.

FIG. 5R shows a partial sectional view of a balloon catheter wherein inflation ports are located near the distal end of the balloon.

FIG. 5S shows a partial sectional view of an embodiment of a balloon catheter comprising multiple balloons inflated by a single lumen.

FIG. 5T shows a partial sectional view of a balloon catheter comprising multiple balloons inflated by multiple lumens.

FIGS. 5U through 5AB show perspective and sectional views of various embodiments of balloon catheters having sensors mounted thereon or therein.

FIG. 6F' is an enlarged side view of the braid of the device of FIG. 6F.

FIG. 8A shows a partial perspective view of a catheter shaft comprising distance markers.

FIG. 8B shows a partial perspective view of a catheter shaft comprising one type of radiopaque markers.

FIG. 8C shows a partial perspective view of a catheter shaft comprising another type of radiopaque markers.

FIG. 8D shows a partial perspective view of a balloon catheter comprising an array of radiopaque markers arranged on the outer surface of the balloon.

FIG. 8E shows a partial perspective view of a balloon catheter comprising an array of radiopaque markers arranged on an inner surface of the balloon.

FIG. 8E' is a longitudinal sectional view of FIG. 8E.

DETAILED DESCRIPTION

The following detailed description, the accompanying drawings and the above-set-forth Brief Description of the Drawings are intended to describe some, but not necessarily all, examples or embodiments of the invention. The contents of this detailed description do not limit the scope of the invention in any way.

A number of the drawings in this patent application show anatomical structures of the ear, nose and throat. In general, these anatomical structures are labeled with the following reference letters:

| | |
|---|---|
| Nasal Cavity | NC |
| Nasopharynx | NP |
| Frontal Sinus | FS |
| Ethmoid Sinus | ES |
| Ethmoid Air Cells | EAC |
| Sphenoid Sinus | SS |
| Sphenoid Sinus Ostium | SSO |
| Maxillary Sinus | MS |
| Mucocele | MC |

Figure 1:
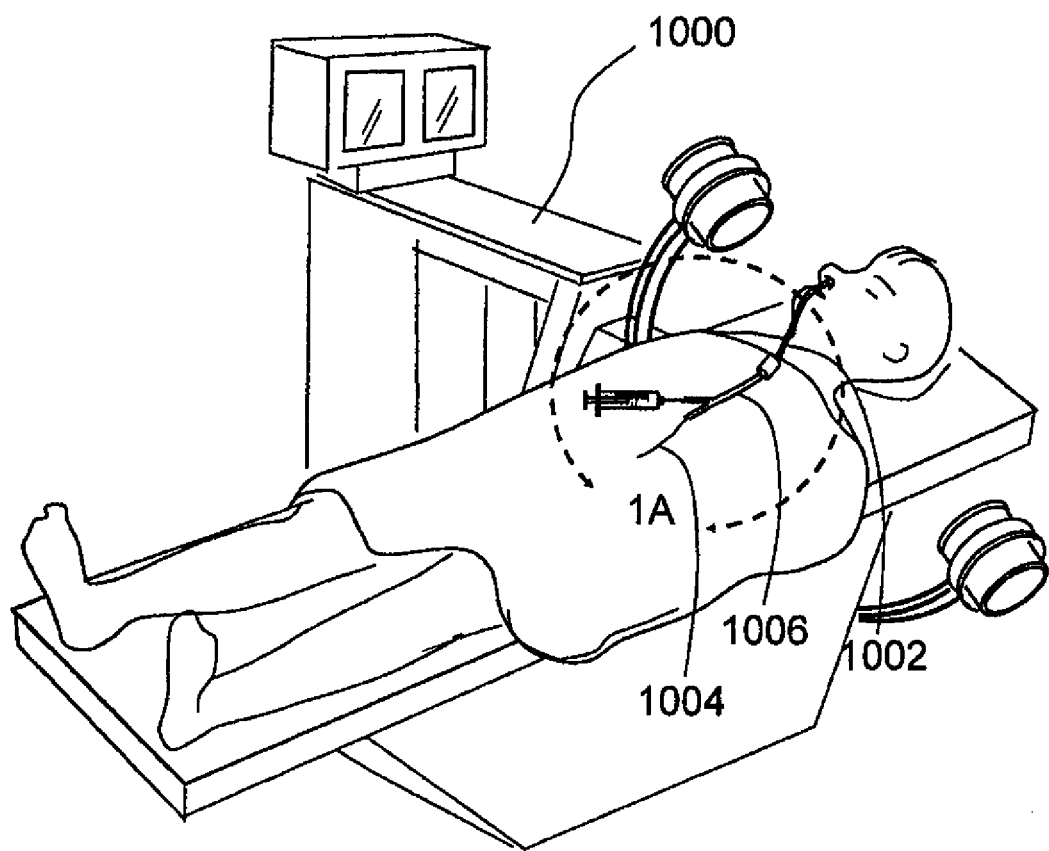
FIG. 1 shows a schematic diagram of a system for catheter-based minimally invasive sinus surgery of the present invention being used to perform a sinus surgery procedure on a human patient.
Figure 1A:
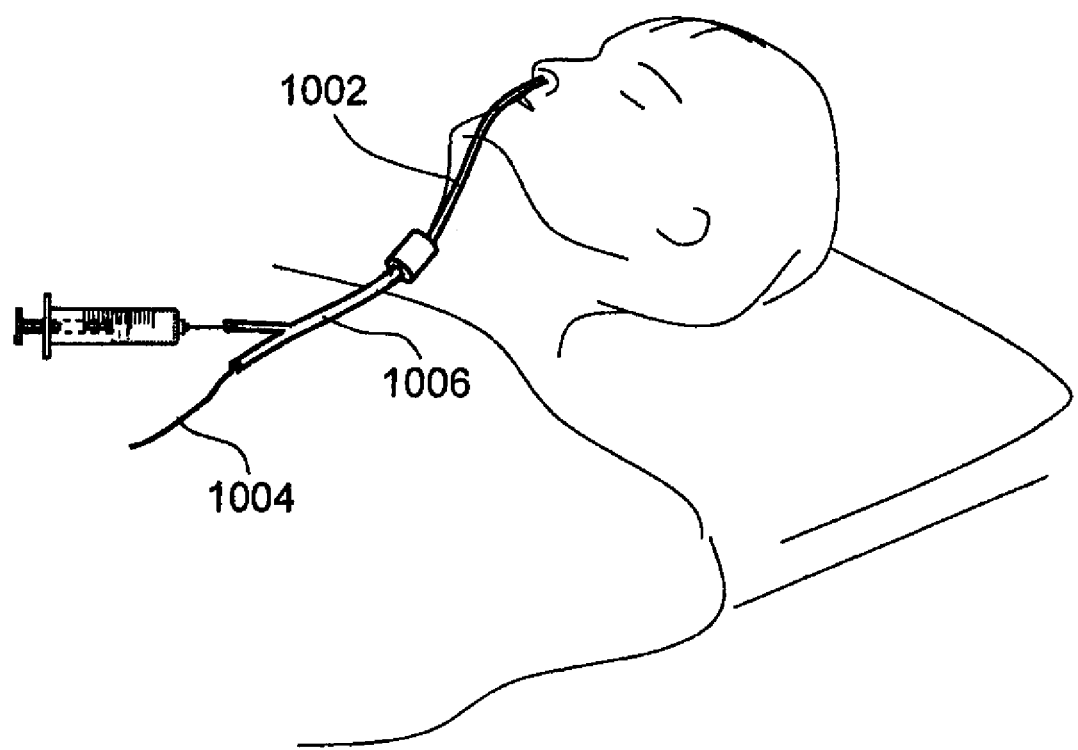
FIG. 1A is an enlarged view of portion "1A" of FIG. 1.

FIGS. 1 and 1A provide a general showing of a minimally invasive surgery system of the present invention comprising a C-arm fluoroscope 1000 that is useable to visualize a first introducing device 1002 (e.g., a guide catheter or guide tube), a second introducing device 1004 (e.g., a guidewire or elongate probe) and a working device 1006 (e.g., a balloon catheter, other dilation catheter, debrider, cutter, etc.). FIGS. 2A-8E' show certain non-limiting examples of the introducing devices 1002 (e.g., a guide catheter or guide tube), 1004 (guides, guidewires, elongate probes, etc.) and working devices 1006 (e.g., a balloon catheters, other dilation catheters, debrider, cutters, etc.) that may be useable in accordance with this invention. The devices 1002, 1004, 1006 may be radiopaque and/or may incorporate radiopaque markers such that C-arm fluoroscope 1000 may be used to image and monitor the positioning of the devices 1002, 1004, 1006 during the procedure. In addition to or, as an alternative to the use of radiographic imaging, the devices 1002, 1004, 1006 may incorporate and/or may be used in conjunction with one or more endoscopic devices, such as the typical rigid or flexible endoscopes or stereo endocscopes used by otolaryngologists during FESS procedures. Also, in addition to or as an alternative to radiographic imaging and/or endoscopic visualizations, some embodiments of the devices 1002, 1004, 1006 may incorporate sensors which enable the devices 1002, 1004, 1006 to be used in conjunction with image guided surgery systems or other electro-anatomical mapping/guidance systems including but not limited to: VectorVision (BrainLAB AG); HipNav (CASurgica); CBYON Suite (CBYON); InstaTrak, FluoroTrak, ENTrak (GE Medical); StealthStation Treon, iOn (Medtronic); Medivision; Navitrack (Orthosoft); OTS (Radionics); VISLAN (Siemens); Stryker Navigation System (Stryker Leibinger); Voyager, Z-Box (Z-Kat Inc.) and NOGA and CARTO systems (Johnson & Johnson). Commercially available interventional navigation systems can also be used in conjunction with the devices and methods. Further non-fluoroscopic interventional imaging technologies including but not limited to: OrthoPilot (B. Braun Aesculap); PoleStar (Odin Medical Technologies; marketed by Medtronic); SonoDoppler, SonoWand (MISON); CT Guide, US Guide (UltraGuide) etc. may also be used in conjunction with the devices and methods. Guidance under magnetic resonance is also feasible if the catheter is modified to interact with the system appropriately.

It is to be appreciated that the devices and methods of the present invention relate to the accessing and dilation or modification of sinus ostia or other passageways within the ear nose and throat. These devices and methods may be used alone or may be used in conjunction with other surgical or non-surgical treatments, including but not limited to the delivery or implantation of devices and drugs or other substances as described in copending U.S. patent application Ser. No. 10/912,578 entitled Implantable Devices and Methods for Delivering Drugs and Other Substances to Treat Sinusitis and Other Disorders filed on Aug. 4, 2004, the entire disclosure of which is expressly incorporated herein by reference.

Figure 2A:
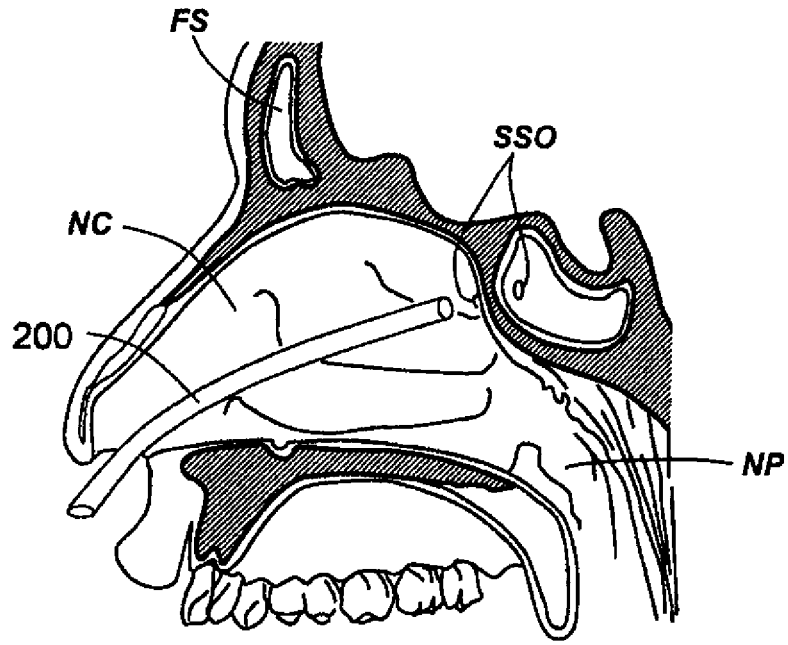
FIGS. 2A through 2D are partial sagittal sectional views through a human head showing various steps of a method for gaining access to a paranasal sinus using a guide and thereafter dilating or remodeling the ostial opening into the paranasal sinus.
Figure 2B:
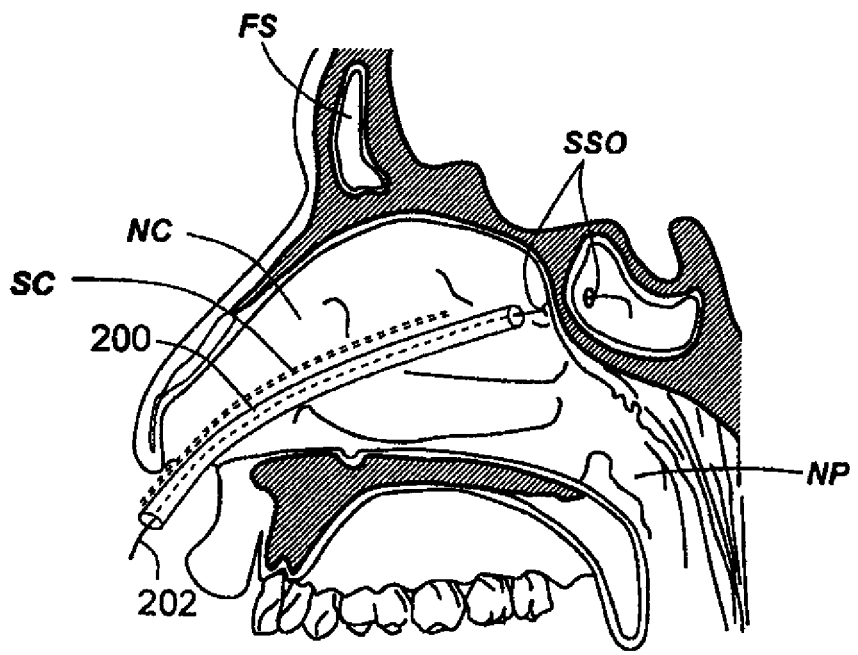
Figure 2C:
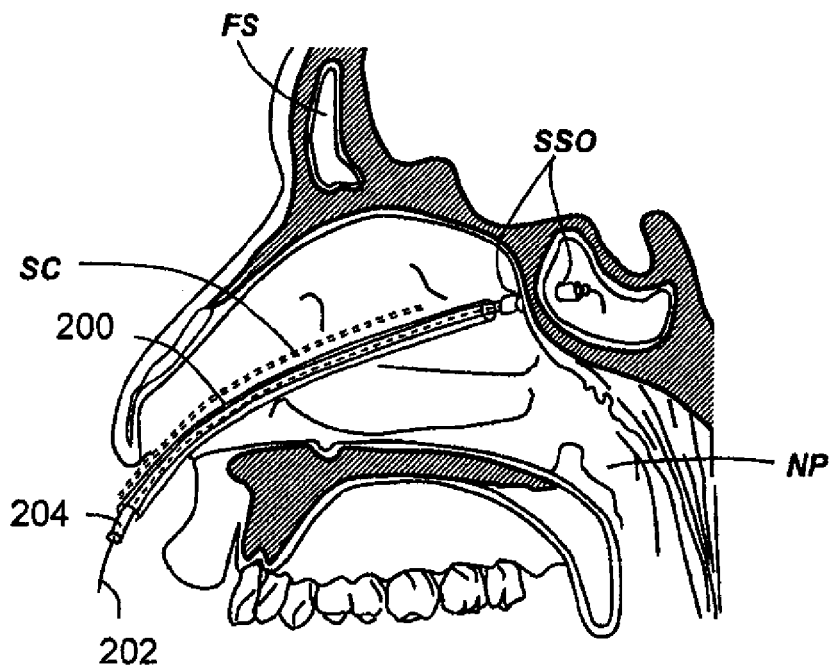
Figure 2D:
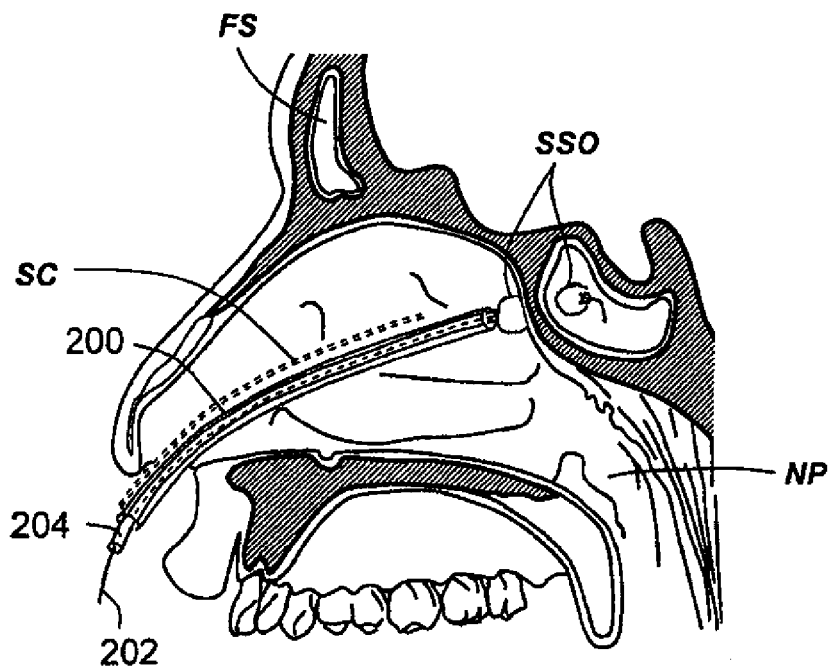

FIGS. 2A through 2D are partial sagittal sectional views through a human head showing various steps of a method of gaining access to a paranasal sinus using a guide catheter. In FIG. 2A, a first introducing device in the form of a guide catheter 200 is introduced through a nostril and through a nasal cavity NC to a location close to an ostium SSO of a sphenoid sinus SS. The guide catheter 200 may be flexible. Flexible devices are defined as devices with a flexural stiffness less than about 200 pound-force per inch over a device length of one inch. The guide catheter 200 may be straight or it may incorporate one or more preformed curves or bends. In embodiments where the guide catheter 200 is curved or bent, the deflection angle of the curve or bend may be in the range of up to 135°. Examples of specific deflection angles formed by the curved or bent regions of the guide catheter 200 are 0°, 30°, 45°, 60°, 70°, 90°, 120° and 135°. Guide catheter 200 can be constructed from suitable elements like Pebax, Polyimide, Braided Polyimide, Polyurethane, Nylon, PVC, Hytrel, HDPE, PEEK, metals like stainless steel and fluoropolymers like PTFE, PFA, FEP and EPTFE. Guide catheter 200 can have a variety of surface coatings e.g. hydrophilic lubricious coatings, hydrophobic lubricious coatings, abrasion resisting coatings, puncture resisting coatings, electrically or thermal conductive coatings, radiopaque coatings, echogenic coatings, thrombogenicity reducing coatings and coatings that release drugs. In FIG. 2B, a second introduction device comprising a guidewire 202 is introduced through the first introduction device (i.e., the guide catheter 200) so that the guidewire 202 enters the sphenoid sinus SS through the ostium SSO. Guidewire 202 may be constructed and coated as is common in the art of cardiology. In FIG. 2C, a working device 204 for example a balloon catheter is introduced over guidewire 202 into the sphenoid sinus SS. Thereafter, in FIG. 2D, the working device 204 is used to perform a diagnostic or therapeutic procedure. In this particular example, the procedure is dilation of the sphenoid sinus ostium SSO, as is evident from FIG. 2D. However, it will be appreciated that the present invention may also be used to dilate or modify any sinus ostium or other man-made or naturally occurring anatomical opening or passageway within the nose, paranasal sinuses, nasopharynx or adjacent areas. After the completion of the procedure, guide catheter 200, guidewire 202 and working device 204 are withdrawn and removed. As will be appreciated by those of skill in the art, in this or any of the procedures described in this patent application, the operator may additionally advance other types of catheters or of the present invention, a guidewire 202 may be steerable (e.g. torquable, actively deformable) or shapeable or malleable. Guidewire 202 may comprise an embedded endoscope or other navigation or imaging modalities including but not limited to fluoroscopic, X-ray radiographic, ultrasonic, radiofrequency localization, electromagnetic, magnetic, robotic and other radiative energy based modalities. In this regard, some of the figures show optional scopes SC is dotted lines. It is to be appreciated that such optional scopes SC may comprise any suitable types of rigid or flexible endoscopes and such optional scopes SC may be separate from or incorporated into the working devices and/or introduction devices of the present invention.

Figure 2E:
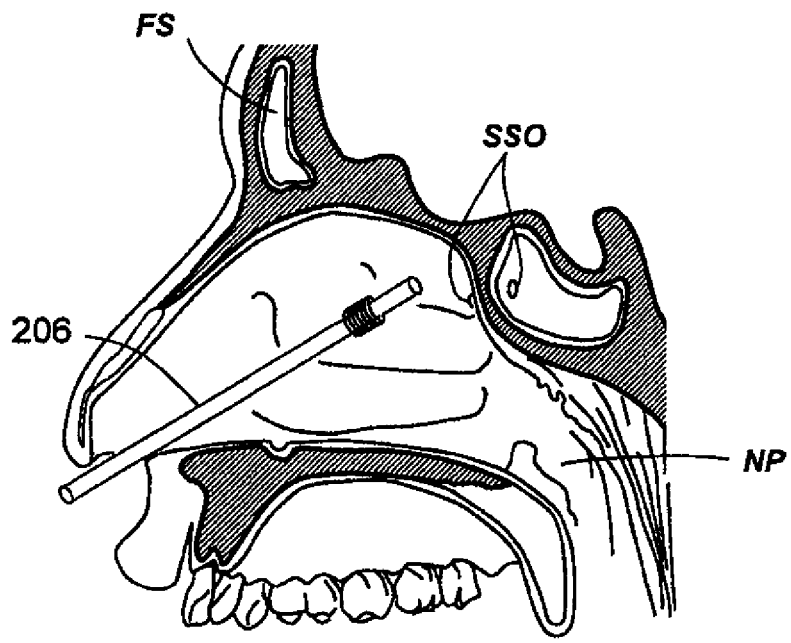
FIGS. 2E through 2H are partial sagittal sectional views through a human head showing various steps of a method for gaining access to a paranasal sinus using a steerable guide and thereafter.
Figure 2F:
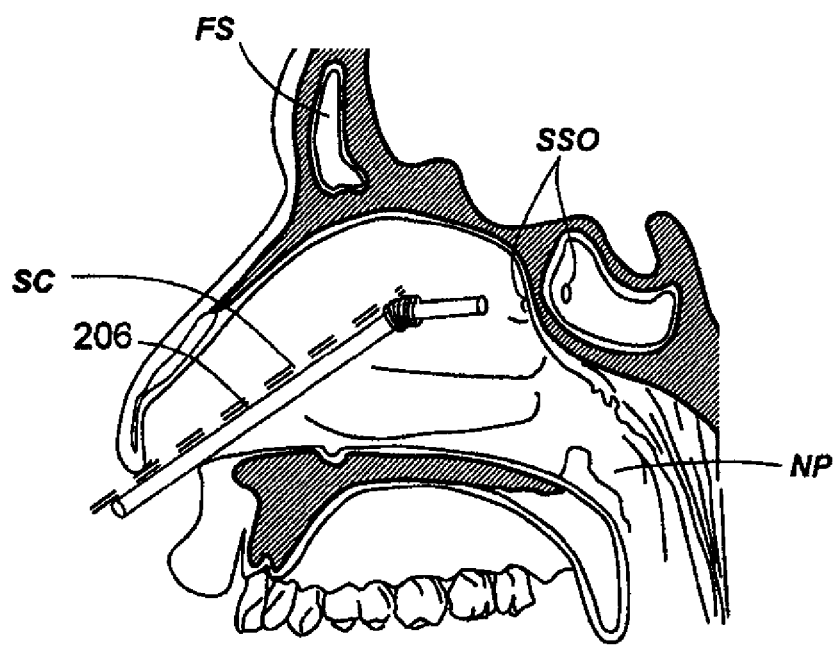
Figure 2G:
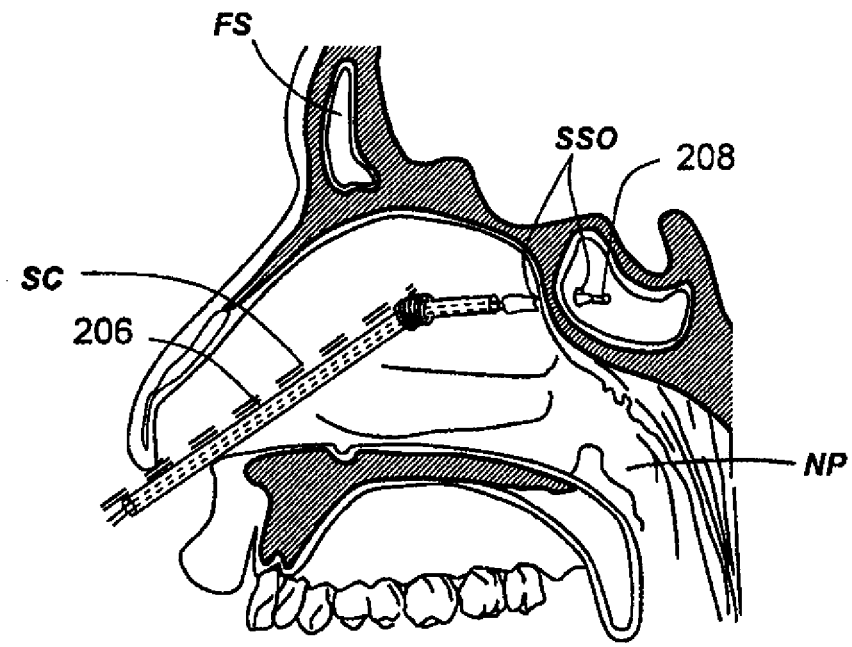
Figure 2H:
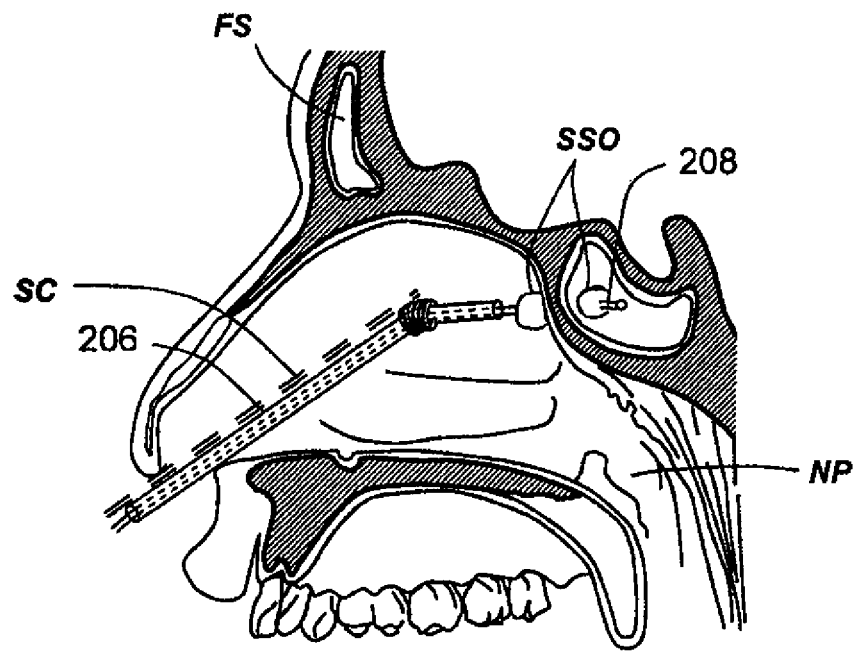

FIGS. 2E through 2H are partial sagittal sectional views through a human head showing various steps of a method of gaining access to a paranasal sinus using a steerable catheter. In FIG. 2E, an introducing device in the form of a steerable catheter 206 is introduced through a nostril. Although commercially available devices are neither designed, nor easily usable for this technique in the sinuses, examples of a device which has a steerable tip with functionality similar to that described here include but are not limited to the Naviport™ manufactured by Cardima, Inc. in Fremont, Calif.; Attain Prevail and Attain Deflectable catheters manufactured by Medtronic; Livewire Steerable Catheters manufactured by St. Jude Medical Inc.; Inquiry™ Steerable Diagnostic Catheters manufactured by Boston Scientific; TargetCath™ manufactured by EBI; Safe-Steer Catheter manufactured by Intraluminal Therapeutics, Inc.; Cynosar manufactured by Catheter Research, Inc.; Torque Control Balloon Catheter manufactured by Cordis Corp. and DynamicDeca Steerable Catheter and Dynamic XT Steerable Catheter manufactured by A.M.I. Technologies Ltd, Israel. Steerable catheter 206 comprises a proximal portion, a distal portion and a controllably deformable region between the proximal portion and the distal portion. In FIG. 2F, the steerable catheter 206 is steered through the nasal anatomy so that the distal portion of steerable catheter 206 is near an ostium SSO of a sphenoid sinus SS. In FIG. 2G, a working device in the form of a balloon catheter 208 is introduced through steerable catheter 206 so that it enters sphenoid sinus SS through the ostium SSO. Thereafter, balloon catheter 208 is adjusted so that the balloon of the balloon catheter is located in the ostium SSO. In FIG. 2H, balloon catheter 208 is used to dilate the ostium SSO. After completion of the procedure, steerable catheter 206 and balloon catheter 208 are withdrawn from the nasal anatomy. In this example, only a first introduction device in the form of a steerable catheter 206 is used to effect insertion and operative positioning of the working device (which in this example is balloon catheter 208). It will be appreciated, however, in some procedures, a second introduction device (e.g., an elongate guide member, guidewire, elongate probe, etc.) could be advanced through the lumen of the steerable catheter 206 and the working device 208 could then be advanced over such second introduction device to the desired operative location.

Figure 2I:
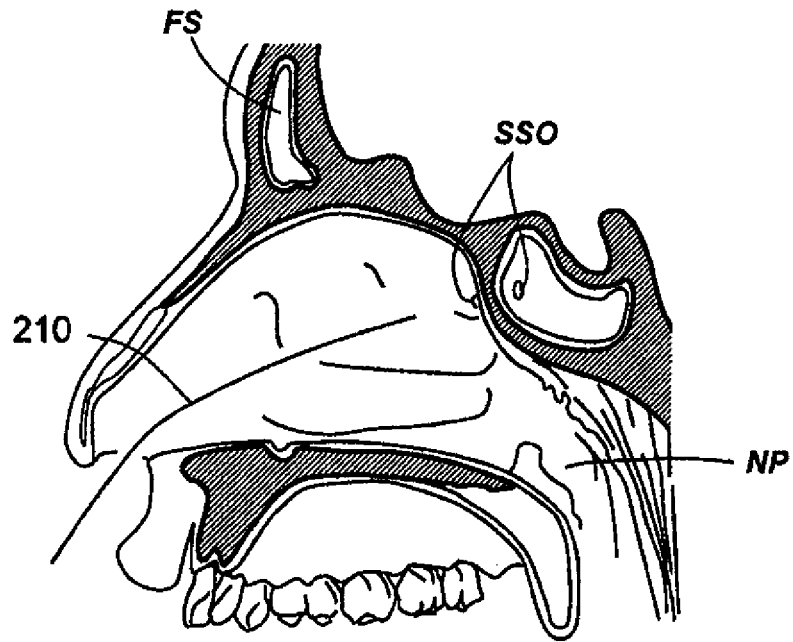
FIGS. 2I through 2L are partial sagittal sectional views through a human head showing various steps of a method for gaining access to a paranasal sinus using an introducing device in the form of a guidewire with a preset shape.
Figure 2J:
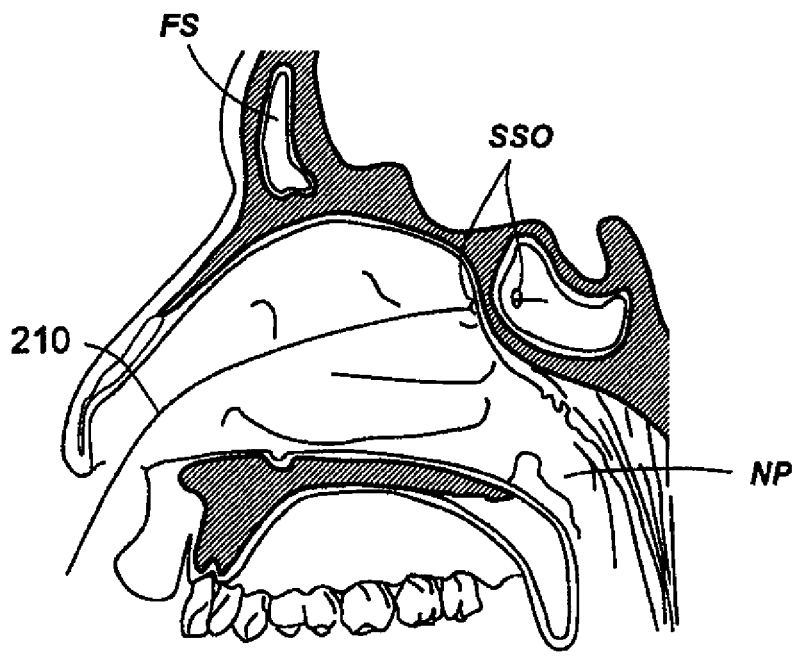
Figure 2K:
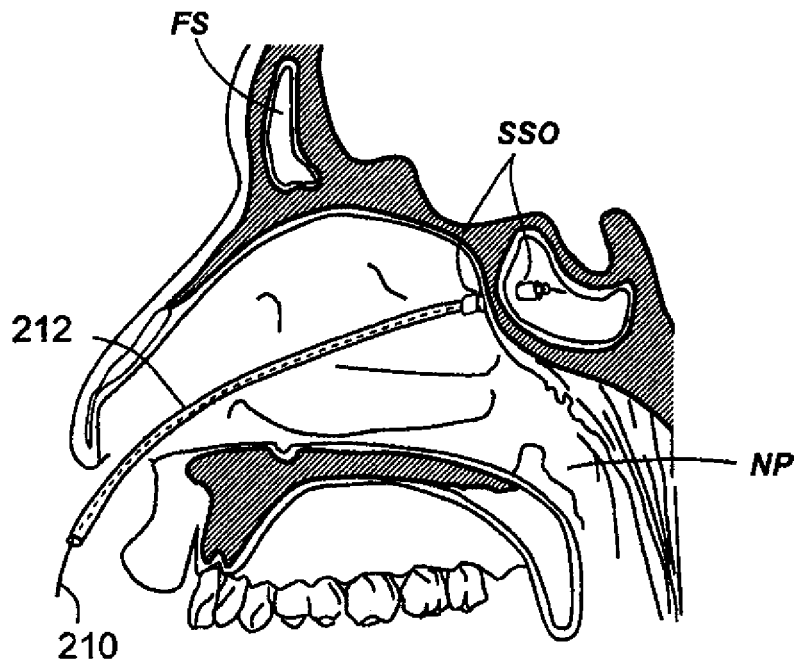
Figure 2L:
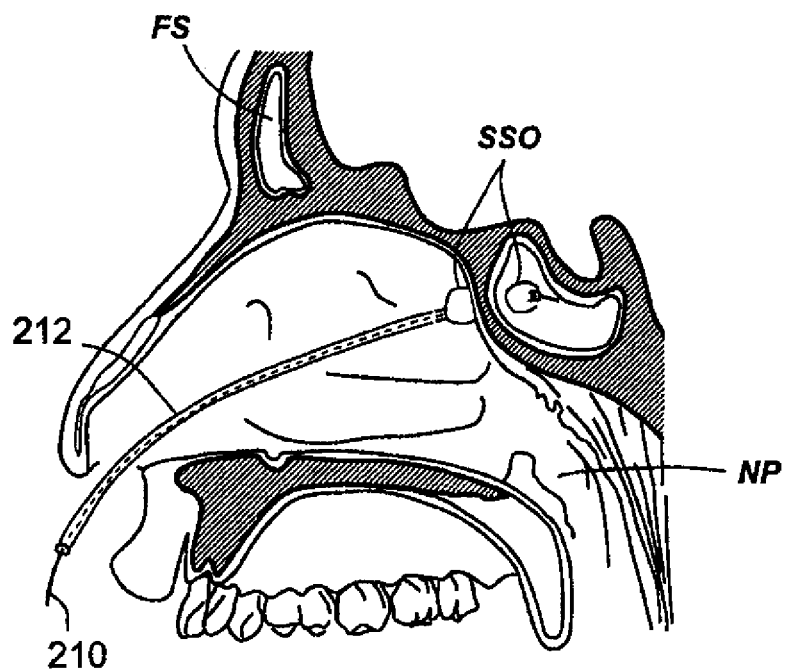

FIGS. 2I through 2L are partial sagittal sectional views through a human head showing various steps of a method for gaining access to a paranasal sinus using an introducing device in the form of a guidewire with a preset shape. In FIG. 2I, an introducing device in the form of a guidewire 210 with a preset shape is introduced in a nasal cavity. Guidewire 210 comprises a proximal portion and a distal portion and is shaped such that it can easily navigate through the nasal anatomy. In one embodiment, guidewire 210 is substantially straight. In another embodiment, guidewire 210 comprises an angled, curved or bent region between the proximal portion and the distal portion. Examples of the deflection angle of the angled, curved or bent regions are 0°, 30°, 45°, 60°, 70°, 90°, 120° and 135°. In FIG. 2J, guidewire 210 is advanced through the nasal anatomy so that the distal tip of guidewire enters a sphenoid sinus SS through an ostium SSO. In FIG. 2K, a working device in the form of a balloon catheter 212 is advanced along guidewire 210 into the sphenoid sinus SS. Typically, as described more fully herebelow, the working device will have a guidewire lumen extending through or formed in or on at least a portion of the working device 212 to facilitate advancement of the working device 212 over the guidewire 212 in the manner well understood in the art of interventional medicine. Thereafter, the position of balloon catheter 212 is adjusted so that the balloon of the balloon catheter is located in the ostium SSO. As described elsewhere in this application, the balloon catheter 212 may be radiopaque and/or may incorporate one or more visible or imageable markers or sensors. In FIG. 2L, balloon catheter 212 is used to dilate the ostium SSO. After completion of the procedure, guidewire 210 and balloon catheter 212 are withdrawn from the nasal anatomy. In one embodiment, balloon catheter 212 is shapeable or malleable.

Figure 2M:
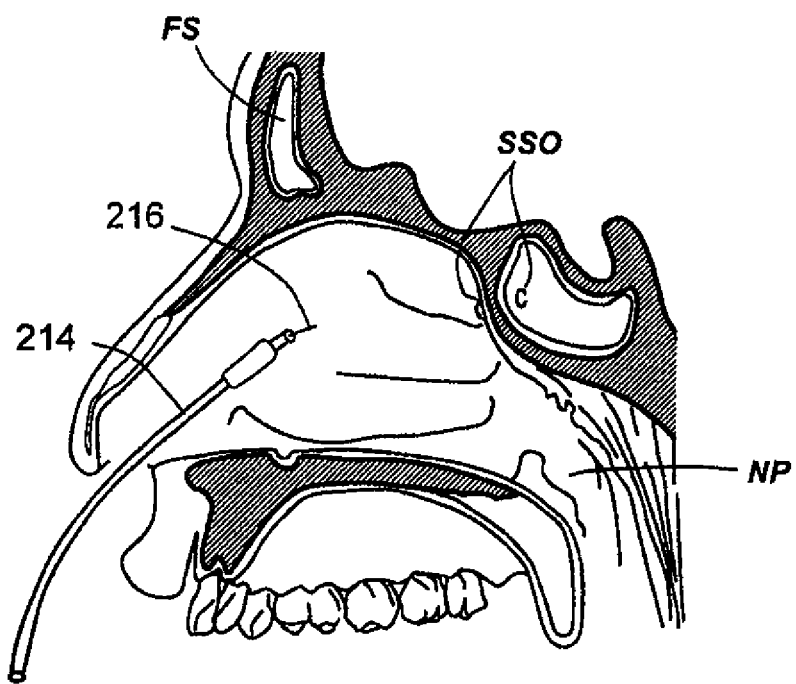
FIGS. 2M through 2O are partial sagittal sectional views through a human head showing various steps of a method for gaining access to a paranasal sinus using a balloon catheter that has a guide protruding from its distal end.
Figure 2N:
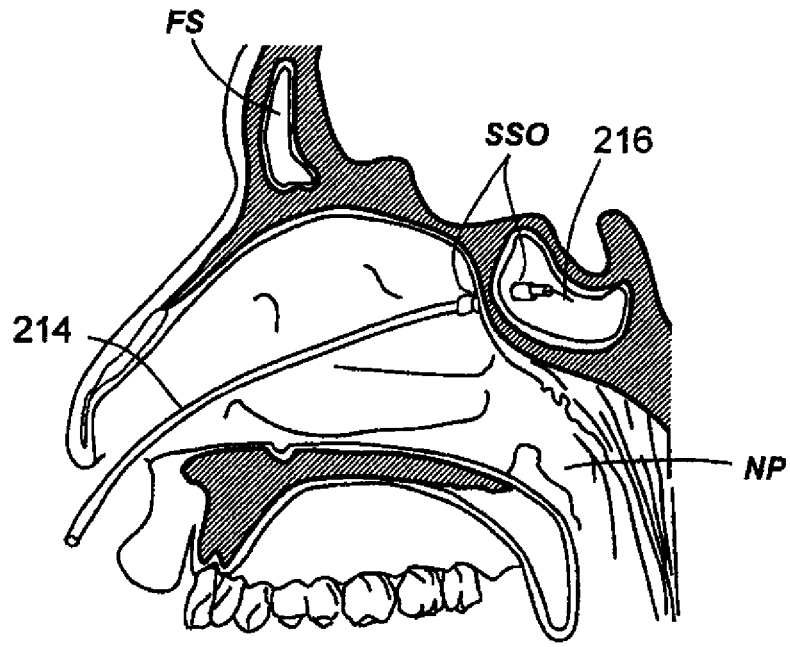
Figure 2O:
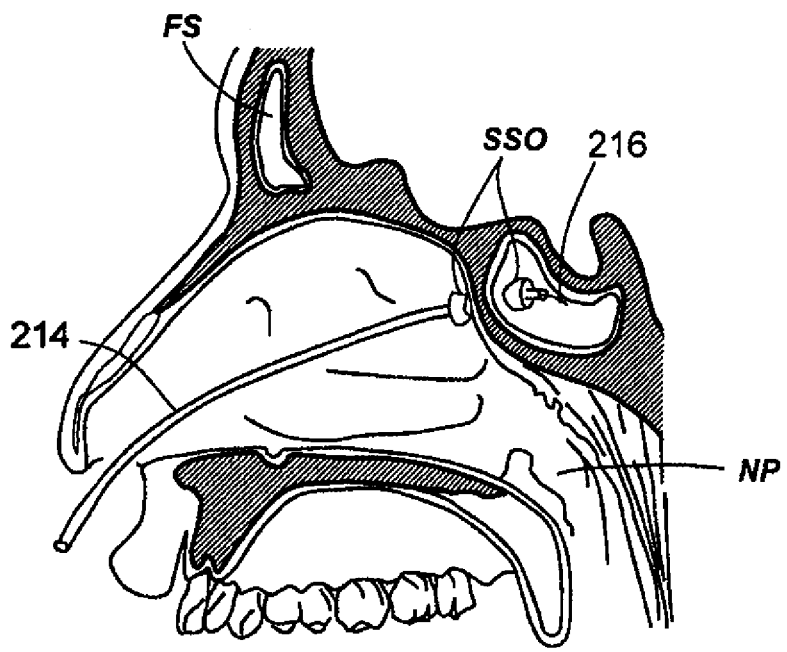

FIGS. 2M through 2O are partial sagittal sectional views through a human head showing various steps of a method of gaining access to a paranasal sinus using a balloon catheter comprising a steering wire at its distal end. In FIG. 2M, a working device comprising a balloon catheter 214 comprising a proximal portion and distal portion is introduced in a nasal cavity. Balloon catheter 214 comprises a steering wire 216 at its distal end. In FIG. 2N, balloon catheter 214 is advanced through the nasal anatomy into a sphenoid sinus SS through a sphenoid sinus ostium SSO. Thereafter, the position of balloon catheter 214 is adjusted so that the balloon of the balloon catheter is located in the ostium SSO. In FIG. 2O, balloon catheter 214 is used to dilate the ostium SSO. After completion of the procedure, balloon catheter 214 is withdrawn from the nasal anatomy. In one embodiment, steering wire 216 can be retracted into or advanced from balloon catheter 214. The retraction or advancement of steering wire can be controlled by several means like a thumb wheel, a slide, a button hooked up to electronic motor and a trigger. In another embodiment, steering wire 216 may be hollow or may incorporate one or more lumen(s) to enable it to introduce or remove devices or diagnostic or therapeutic agents, examples of which are described in copending U.S. patent application Ser. No. 10/912,578 entitled Implantable Devices and Methods for Delivering Drugs and Other Substances to Treat Sinusitis and Other Disorders filed on Aug. 4, 2004, the entire disclosure of which is expressly incorporated herein by reference.

Figure 2P:
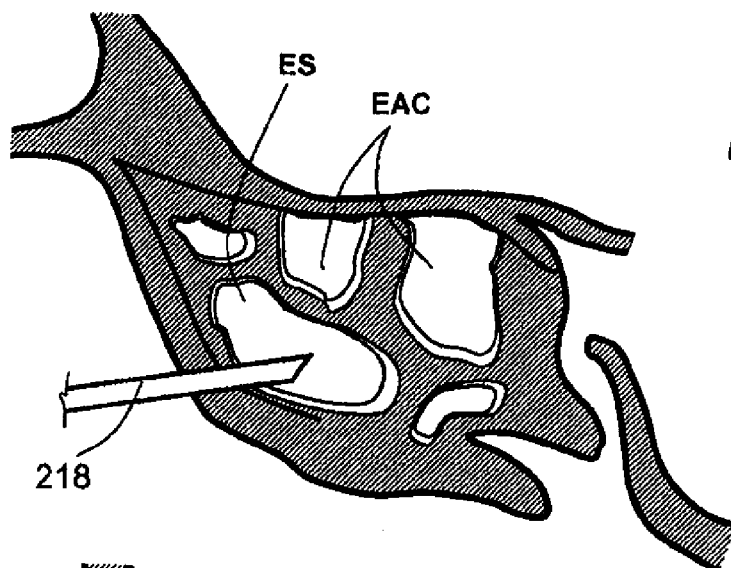
FIGS. 2P through 2X are partial sagittal sectional views through a human head showing various steps of a method of accessing an ethmoid sinus through a natural or artificially created opening of the ethmoid sinus.
Figure 2Q:
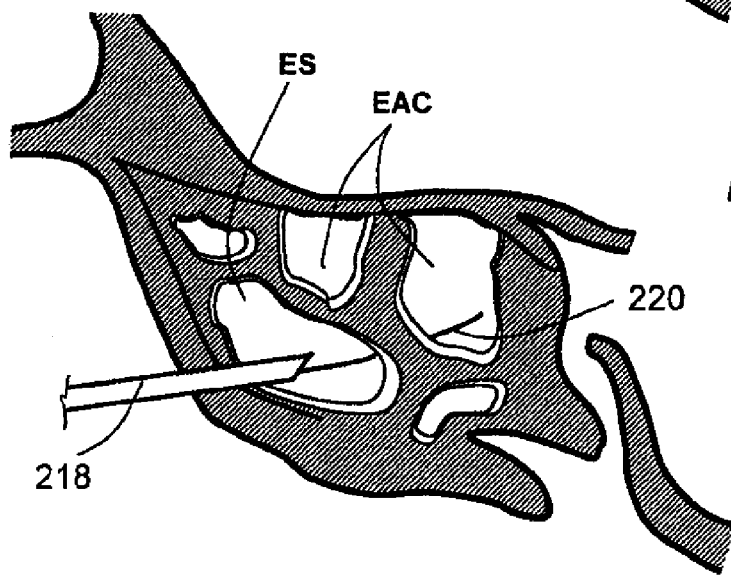
Figure 2R:
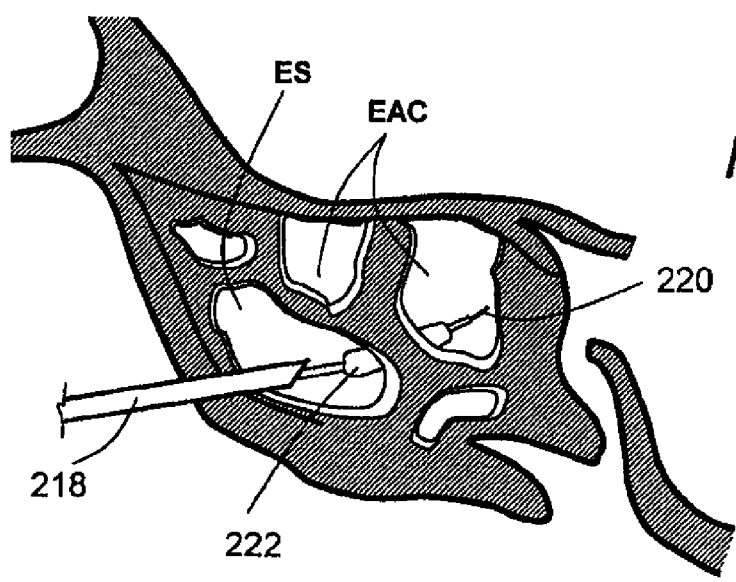
Figure 2S:
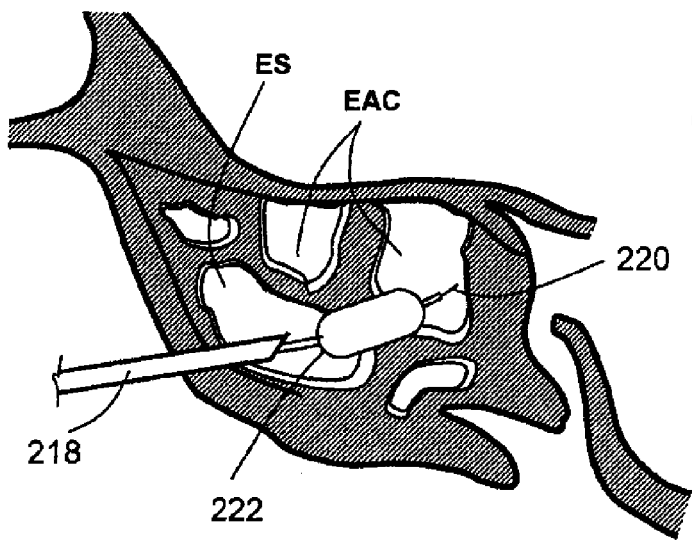
Figure 2T:
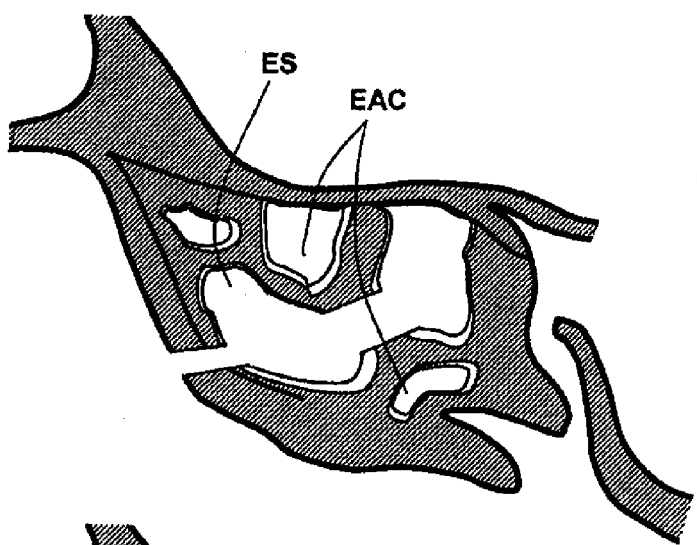
Figure 2U:
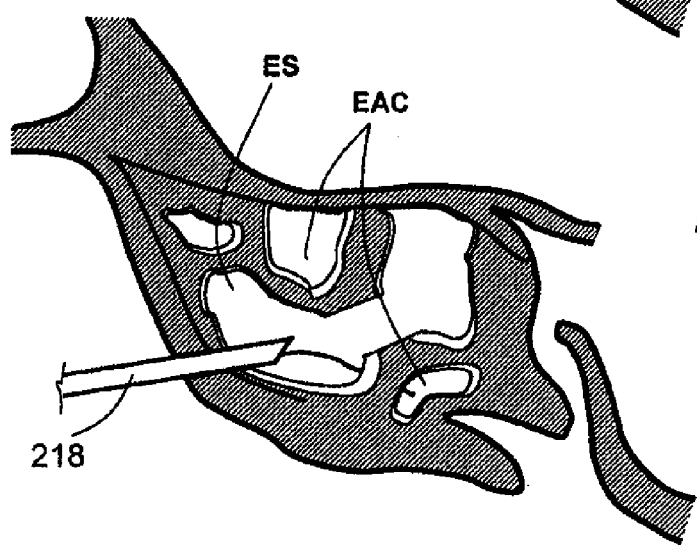
Figure 2V:
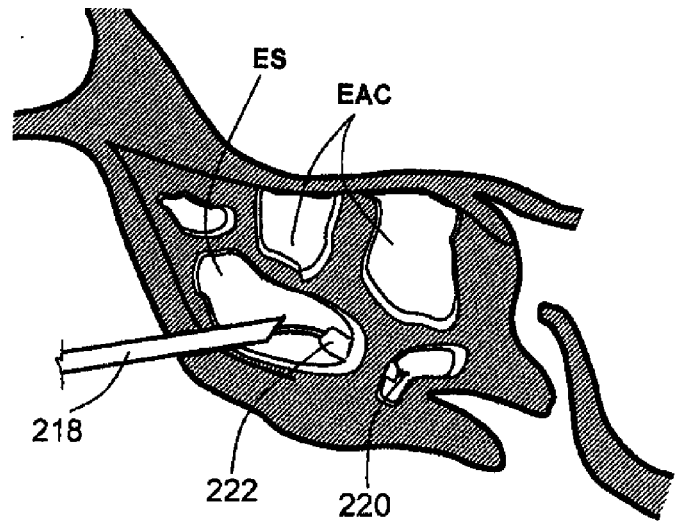
Figure 2W:
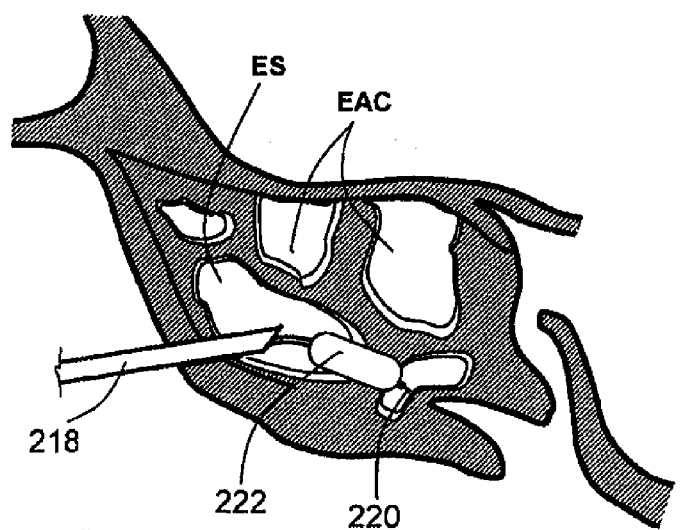
Figure 2X:
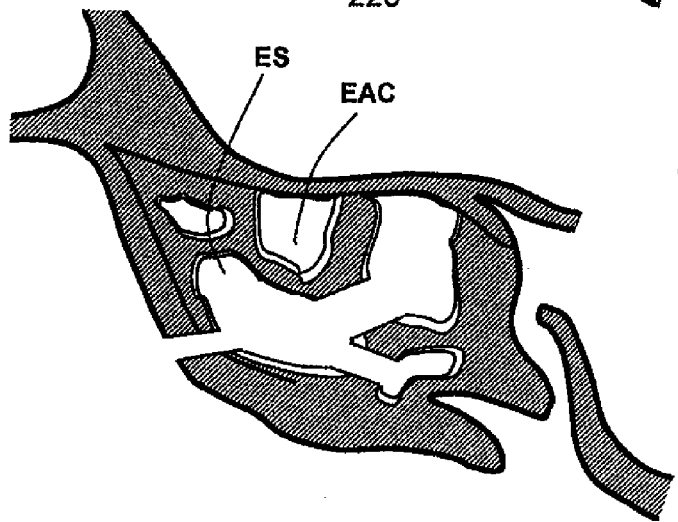

FIGS. 2P through 2X are partial sagittal sectional views through a human head showing various steps of a method for accessing an ethmoid sinus through a natural or artificially created opening of the ethmoid sinus. In FIG. 2P, an introducing device in the form of a guide catheter 218 is introduced in an ethmoid sinus ES. Ethmoid sinus ES comprises multiple ethmoid air cells EAC. In FIG. 2Q, a guidewire 220 is introduced through guide catheter into a first EAC. Thereafter, in FIG. 2R, a balloon catheter 222 is introduced over guidewire 220 into the first EAC. In FIG. 2S, balloon catheter 222 is inflated to dilate the structures of ES. In FIG. 2T, guide catheter 218, guidewire 220 and balloon catheter 222 are withdrawn leaving a first new passage in the ES. The newly created passage in the ES facilitates drainage of the mucous through the ES. Alternatively, in FIG. 2U, only balloon catheter 222 is withdrawn. The position of guide catheter 218 is adjusted and guidewire 220 is introduced into a second EAC. In FIG. 2V, balloon catheter 222 is introduced over guidewire 220 into the second EAC. In FIG. 2W, balloon catheter 222 is inflated to dilate the structures of ES. In FIG. 2X, guide catheter 218, guidewire 220 and balloon catheter 222 are withdrawn leaving a second new passage in the ES. The second new passage in the ES further facilitates drainage of the mucous through the ES. This method of dilating the structures of ES can be repeated to create multiple new passages in the ES.

Figure 2Y:
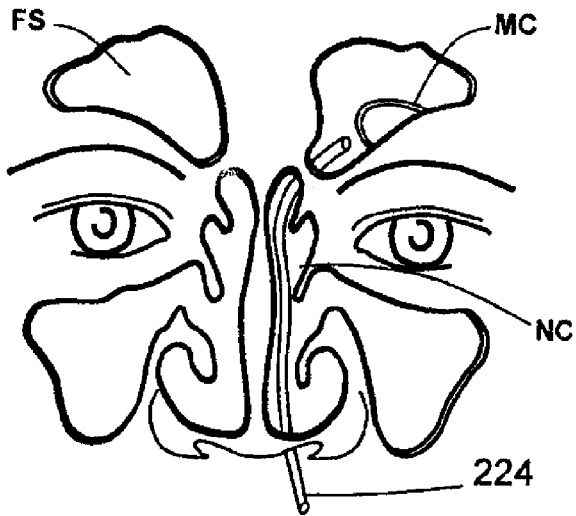
Figure 2Z:
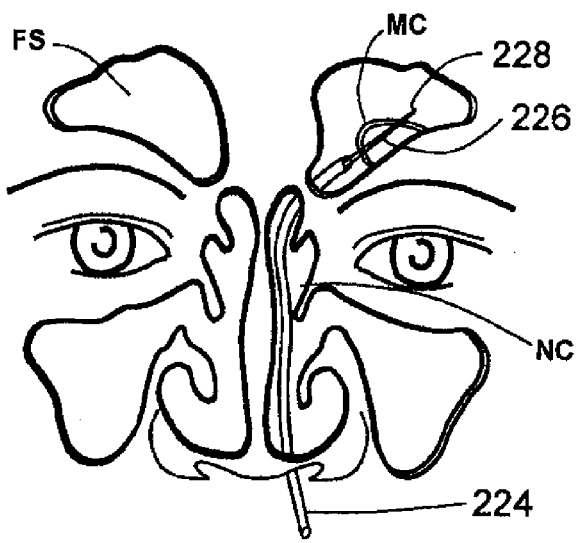
Figure 2A:
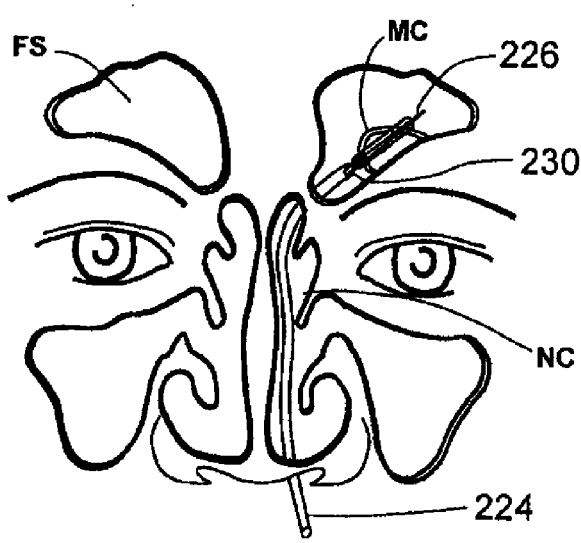
Figure 2A:
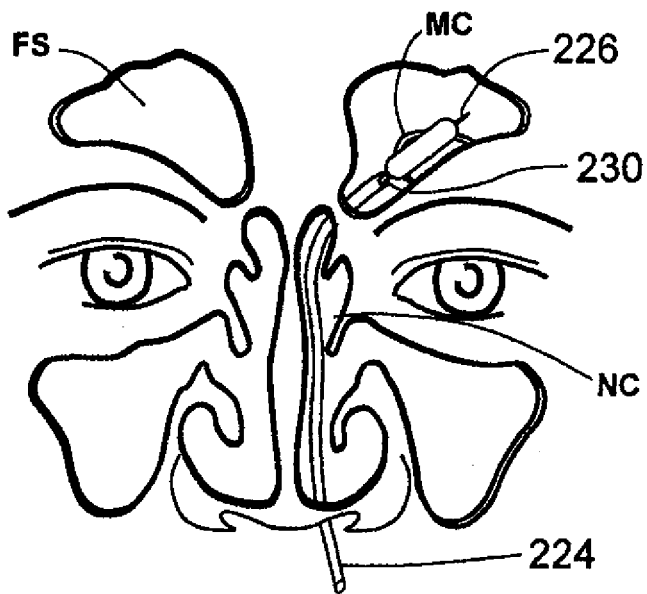
Figure 2A:
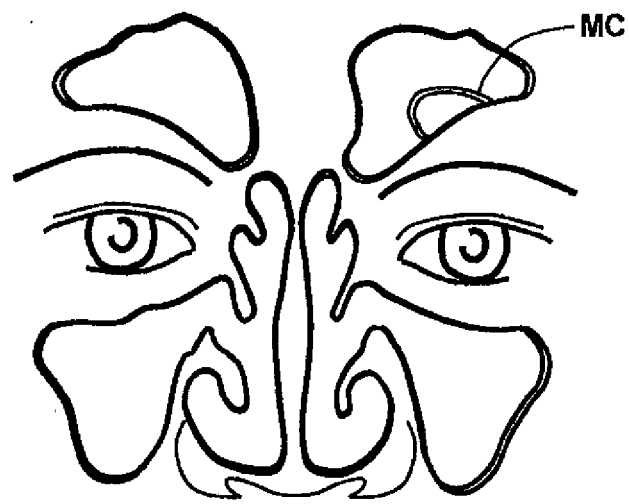

FIGS. 2Y through 2AC are partial coronal sectional views through a human head showing various steps of a method for treating a mucocele in a frontal sinus. In FIG. 2Y, an introducing device in the form of a guide catheter 224 is introduced in a frontal sinus FS through the nasal cavity NC. Frontal sinus FS has a mucocele MC to be treated. In FIG. 2Z, a penetrating device 226 comprising a sharp tip 228 is introduced through guide catheter 224 such that penetrating device 226 punctures the MC at least partially. In FIG. 2AA, a balloon catheter 230 is introduced over penetrating device 226 into the MC. Thereafter, in FIG. 2AB, balloon catheter 230 is inflated to rupture the MC and allow the drainage of contents of the MC. In FIG. 2AC, penetrating device 226 and balloon catheter 230 are withdrawn.

The methods disclosed herein may also comprise the step of cleaning or lavaging anatomy within the nose, paranasal sinus, nasopharynx or nearby structures including but not limited to irrigating and suctioning. The step of cleaning the target anatomy can be performed before or after a diagnostic or therapeutic procedure.

The methods of the present invention may also include one or more preparatory steps for preparing the nose, paranasal sinus, nasopharynx or nearby structures for the procedure, such as spraying or lavaging with a vasoconstricting agent (e.g., 0.025-0.5% phenylephyrine or Oxymetazoline hydrochloride (Neosynephrine or Afrin) to cause shrinkage of the nasal tissues, an antibacterial agent (e.g., provodine iodine (Betadine), etc. to cleanse the tissues, etc.

Figure 3A:
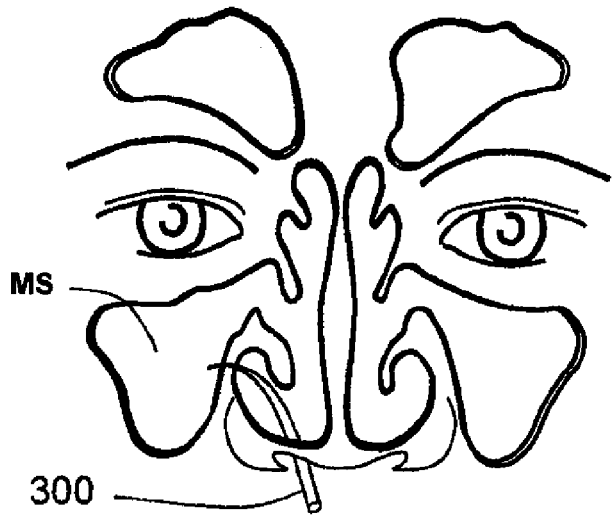
FIGS. 3A through 3C are partial coronal sectional views through a human head showing various steps of a method of accessing a paranasal sinus through an artificially created opening of the paranasal sinus.
Figure 3B:
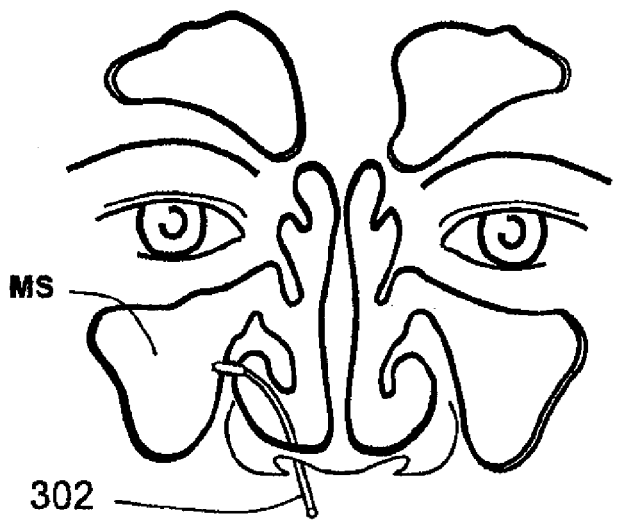
Figure 3C:
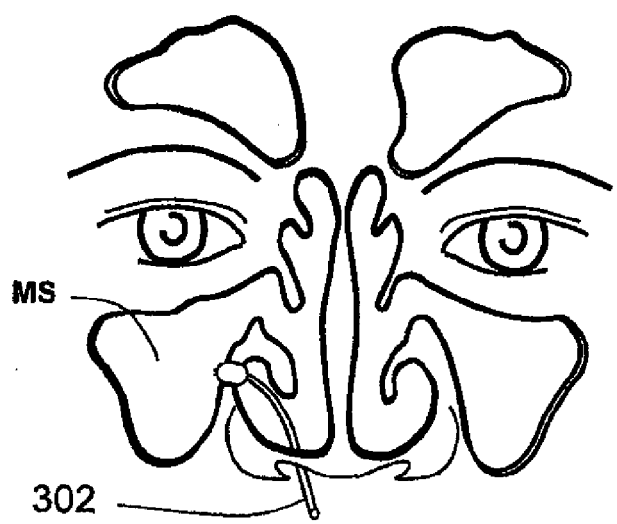

FIGS. 3A through 3C are partial coronal sectional views through a human head showing various steps of a method of accessing a paranasal sinus through an artificially created opening of the paranasal sinus. In FIG. 3A, a puncturing device 300 is inserted through a nostril and used to create an artificial opening in a maxillary sinus. There are several puncturing devices well known in the art like needles including needles, needles with bent shafts, dissectors, punches, drills, corers, scalpels, burs, scissors, forceps and cutters. In FIG. 3B, puncturing device 300 is withdrawn and a working device for example a balloon catheter 302 is introduced through the artificial opening into the maxillary sinus. In FIG. 3C, balloon catheter 302 is used to dilate the artificially created opening in the maxillary sinus. After this step, the balloon catheter 302 is withdrawn. It will be appreciated that, in some embodiments, the puncturing device 300 may have a lumen through which an introduction device (e.g., a guidewire or other elongate probe or member), may be inserted into the maxillary sinus and the puncturing device 300 may then be removed leaving such introduction device (e.g., a guidewire or other elongate probe or member) in place. In such cases, the working device (e.g., balloon catheter 302) may incorporate a lumen or other structure that allows the working device (e.g., balloon catheter 300) to be advanced over the previously inserted introduction device (e.g., a guidewire or other elongate probe or member).

Figure 4A:
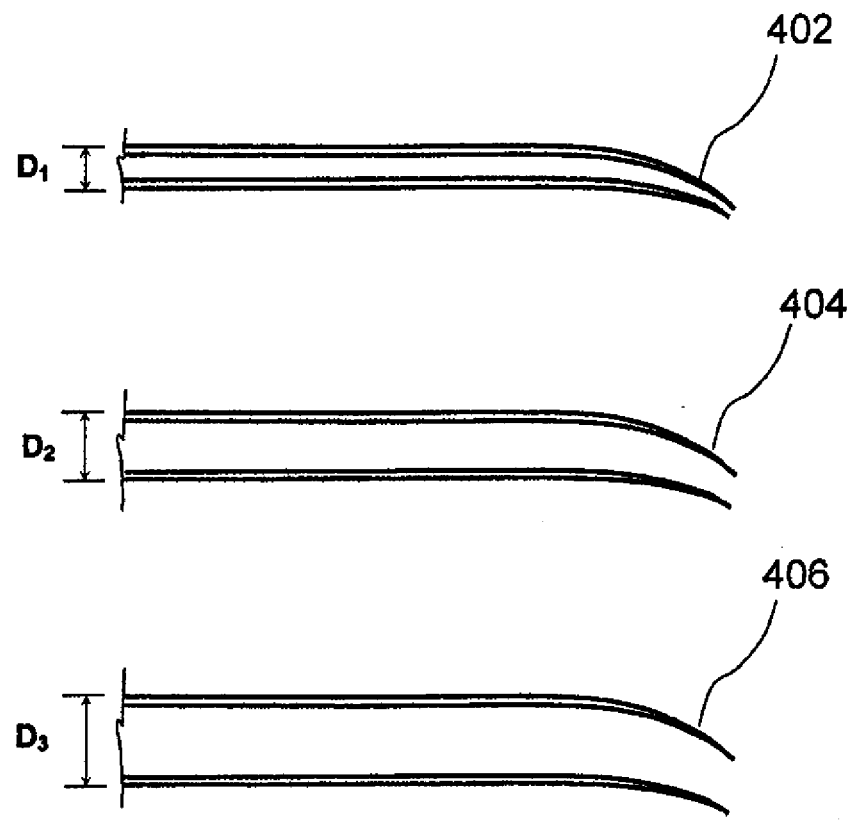
FIG. 4A shows a partial longitudinal sectional view of a system for dilating a sinus ostium or other intranasal anatomical structure, such system comprising three progressively larger dilators useable in sequence.

In the methods illustrated so far, balloon catheters were used only as an example for the several alternate working devices that could be used with this invention. FIG. 4A shows a sectional view of an example of a working device comprising a set of three sequential dilators: a first sequential dilator 402, a second sequential dilator 404 and a third sequential dilator 406. The $D_3$ of third sequential dilator 406 is greater than the diameter $D_2$ of second sequential dilator 404 which in turn is greater than the diameter $D_1$ of first sequential dilator 402. The sequential dilators may comprise one or more bent or angled regions. The sequential dilators can be constructed from a variety of biocompatible materials like stainless steel 316. A variety of other metals, polymers and materials can also be used to construct the sequential dilators.

Figure 4B:
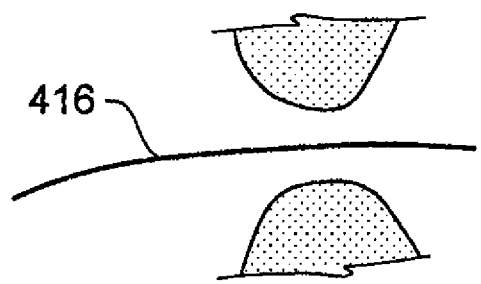
FIGS. 4B through 4E show various steps of a method of dilating a nasal cavity using a working device comprising a balloon catheter with a pressure-expandable stent.
Figure 4C:
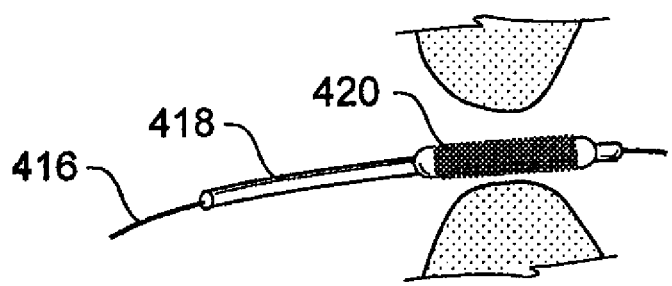
Figure 4D:
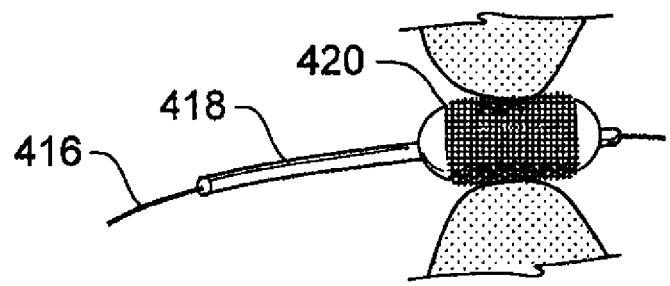
Figure 4E:
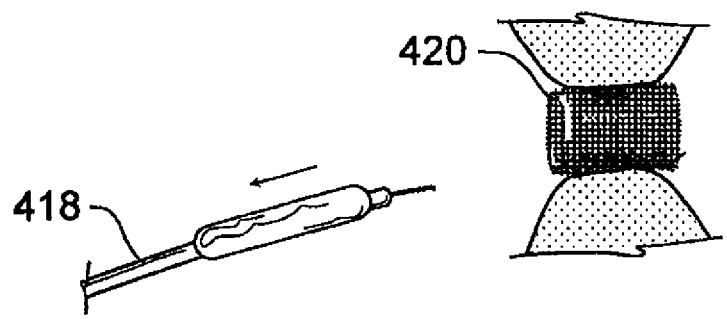

FIGS. 4B through 4E show various steps of a method of dilating a nasal cavity using a working device comprising a balloon catheter with a pressure-expandable stent. In FIG. 4B, an introducing device e.g. a guidewire 416 is introduced into a nasal cavity e.g. an ostium of a sinus. In FIG. 4C, a balloon catheter 418 is introduced over guidewire 416 into the nasal cavity. Balloon catheter 418 comprises a pressure-expandable stent 420. The position of balloon catheter 418 is adjusted so that pressure-expandable stent 420 is located substantially within the target anatomy where the stent is to be deployed. In FIG. 4D, the balloon of balloon catheter 418 is expanded to deploy pressure-expandable stent 420. In FIG. 4E, balloon catheter 418 is withdrawn leaving pressure-expandable stent 420 in the nasal cavity. Several types of stent designs can be used to construct stent 420 like metallic tube designs, polymeric tube designs, chain-linked designs, spiral designs, rolled sheet designs, single wire designs etc. These designs may have an open celled or closed celled structure. A variety of fabrication methods can be used for fabricating stent 420 including but not limited to laser cutting a metal or polymer element, welding metal elements etc. A variety of materials can be used for fabricating stent 420 including but not limited to metals, polymers, foam type materials, plastically deformable materials, super elastic materials etc. Some non-limiting examples of materials that can be used to construct the stent are silicones e.g. silastic, polyurethane, gel-film and polyethylene. A variety of features can be added to stent 420 including but not limited to radiopaque coatings, drug elution mechanisms etc.

Figure 4F:
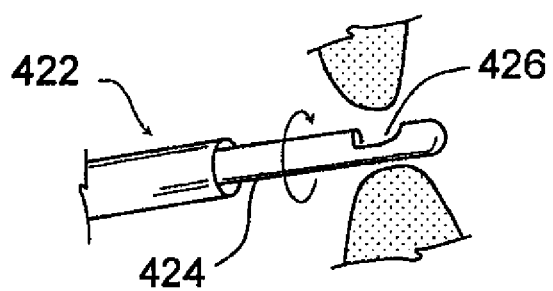
FIG. 4F shows a partial perspective view of a working device that comprises a side suction and/or side cutter.

FIG. 4F shows a partial perspective view of an embodiment of a working device comprising a side suction and/or cutting device 422 comprising a device body 424 having a side opening 426. Cutting device 422 is advanced into a passageway such as a nostril, nasal cavity, meatus, ostium, interior of a sinus, etc. and positioned so that side opening 426 is adjacent to matter (e.g., a polyp, lesion, piece of debris, tissue, blood clot, etc.) that is to be removed. Cutting device 422 is rotated to cut tissue that has been positioned in the side opening 426. Cutting device 422 may incorporate a deflectable tip or a curved distal end which may force side opening 426 against the tissue of interest. Further, this cutting device 422 may have an optional stabilizing balloon incorporated on one side of cutting device 422 to press it against the tissue of interest and may also contain one or more on-board imaging modalities such as ultrasound, fiber or digital optics, OCT, RF or electro-magnetic sensors or emitters, etc.

Figure 4G:
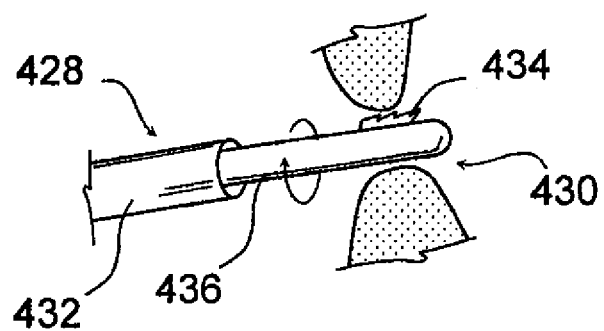
FIG. 4G shows a partial perspective view of a working device that comprises a rotating cutter to cut away tissue.

FIG. 4G shows a partial perspective view of an embodiment of a working device comprising a rotating cutter device to cut away tissue. Rotating cutter device 428 comprises a rotating member 430 enclosed in an introducing device 432. Rotating member 430 comprises a rotating blade 434 located near the distal region of rotating member 430. Rotating blade 434 may be retractable into rotating member 430. Rotating cutter device 428 is inserted in a passageway 436 such as a nostril, nasal cavity, meatus, ostium, interior of a sinus, etc. and positioned so that rotating blade 434 is adjacent to matter (e.g., a polyp, lesion, piece of debris, tissue, blood clot, etc.) that is to be removed. Thereafter, rotating member 430 is rotated to cause rotating blade 434 to remove tissue. In one embodiment, rotating member 430 can be retracted into introducing device 432. In another embodiment, rotating cutter device 428 may comprise a mechanism for suction or irrigation near the distal end of rotating cutter device 428.

Figure 4H:
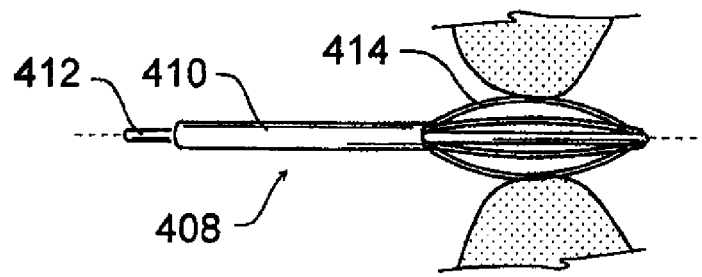
FIGS. 4H and 4I show various steps of a method of dilating the ostium of a paranasal sinus or other nasal passageway using a mechanical dilator.
Figure 4I:
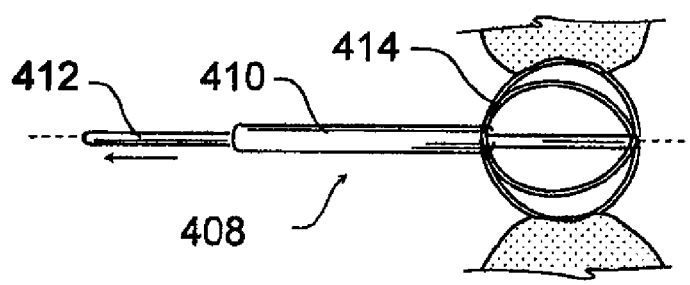

FIGS. 4H and 4I show various steps of a method of dilating a nasal cavity using a working device comprising a mechanical dilator 408. Mechanical dilator 408 comprises an outer member 410, an inner member 412 and one or more elongate bendable members 414. Inner member 412 can slide within outer member 410. The proximal ends of bendable members 414 are attached to distal end of outer member 410 and the distal ends of bendable members 414 are attached to distal end of inner member 412. In FIG. 4H, mechanical dilator 408 is inserted into an opening in the nasal anatomy e.g. an ostium of a sinus. Mechanical dilator 408 is positioned in the opening such that bendable members 414 are within the opening in the nasal anatomy. In FIG. 4I, relative motion of outer member 410 and inner member 412 causes the distal end of outer member 410 to come closer to the distal end of inner member 412. This causes bendable members 414 to bend such that the diameter of the distal region of mechanical dilator 408 increases. This causes bendable members 414 to come into contact with the opening in the nasal anatomy and exert an outward pressure to dilate the opening. Various components of mechanical dilator 408 like outer member 410, inner member 412 and bendable members 414 can be constructed from suitable biocompatible materials like stainless steel 316. A variety of other metals, polymers and materials can also be used to construct the various components of mechanical dilator 408. In one embodiment, outer member 410 is substantially rigid and inner member 412 is flexible. Outer member 410 can be substantially straight or may comprise one or more bent or angled regions. Inner member 412 may comprise one or more lumens.

Figure 4J:
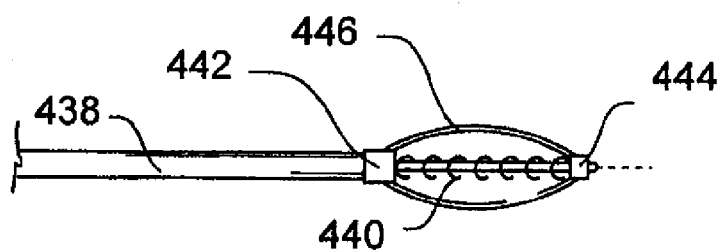
FIGS. 4J and 4K show perspective views of a mechanical dilator comprising a screw mechanism.
Figure 4K:
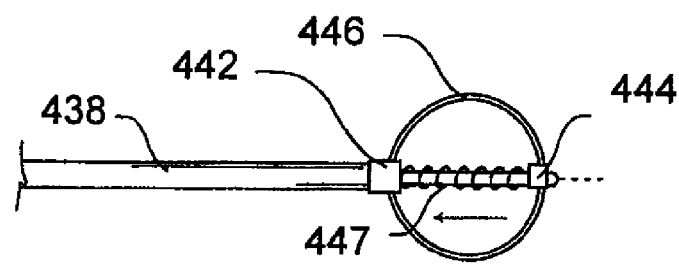

FIGS. 4J and 4K illustrate a perspective view of a design of a mechanical dilator comprising a screw mechanism. FIG. 4J shows the mechanical dilator comprising an outer member 438 and an inner screw member 440. Inner screw member 440 is connected to outer member 438 through a first pivot 442 located on the distal end of outer member 438. The distal end of inner screw member 440 is connected to a second pivot 444. The mechanical dilator further comprises one or more bendable members 446. The distal end of bendable members 446 is attached to second pivot 444 and the proximal end of bendable members 446 is attached to first pivot 442. In FIG. 4K, inner screw member 440 is rotated in one direction. This causes second pivot 444 to come closer to first pivot 442. This causes bendable members 446 to bend in the radial direction exerting an outward radial force. This force can be used to dilate or displace portions of the anatomy. Outer member 438 can be substantially straight or may comprise one or more bent or angled regions. Inner screw member 440 may comprise one or more lumens.

FIGS. 4L and 4M illustrate sectional views of a design of a mechanical dilator comprising a pushable member. FIG. 4L shows the mechanical dilator comprising an outer member 448 comprising one or more bendable regions 449 on the distal end of outer member 448. Mechanical dilator further comprises an inner pushable member 450 comprising an enlarged region 452 on the distal end of inner pushable member 450. In FIG. 4M, inner pushable member 450 is pushed in the distal direction. This exerts an outward force on bendable regions 449 causing bendable regions 449 to bend in a radial direction exerting an outward force. This force can be used to dilate or displace portions of the anatomy. Outer member 448 can be substantially straight or may comprise one or more bent or angled regions. Inner pushable member 450 may comprise one or more lumens.

FIGS. 4N and 4O illustrate sectional views of a design of a mechanical dilator comprising a pullable member. FIG. 4N shows the mechanical dilator comprising an outer member 454 comprising one or more bendable regions 456 on the distal end of outer member 454. Mechanical dilator further comprises an inner pullable member 458 comprising an enlarged region 460 on the distal end of inner pullable member 458. In FIG. 4O, inner pullable member 458 is pulled in the proximal direction. This exerts an outward force on bendable regions 456 causing bendable regions 456 to bend in a radial direction exerting an outward force. This force can be used to dilate or displace portions of the anatomy. Outer member 454 can be substantially straight or may comprise one or more bent or angled regions. Inner pullable member 458 may comprise one or more lumens.

FIGS. 4P and 4Q illustrate sectional views of a design of a mechanical dilator comprising a hinged member. FIG. 4P shows the mechanical dilator comprising an outer member 462 comprising one or more bendable regions 464 located on the distal end of outer member 462. The mechanical dilator also comprises an inner member 466 located within outer member 462. In one embodiment, inner member 466 is tubular. The distal end of inner member 466 comprises one or more first hinges 468. First hinges 468 are hinged to the proximal ends of one or more moving elements 470. Distal ends of moving elements 470 are hinged to one or more second hinges 472 located on the inner surface of outer member 462. In FIG. 4Q, inner member 466 is pushed in the distal direction. This causes moving elements 470 to exert an outward radial force on bendable regions 464 causing bendable regions 464 to bend in an outward radial direction with an outward force. This outward force can be used to dilate or displace portions of the anatomy. Outer member 462 can be substantially straight or may comprise one or more bent or angled regions. Inner member 466 may comprise one or more lumens.

FIGS. 4R through 4W illustrate examples of configurations of mechanical dilators in FIGS. 4H through 4Q. FIG. 4R shows a sectional view of a mechanical dilator comprising an inner member 474, an outer stationary member 476 and an outer bendable member 478. In FIG. 4S, movement of inner member 474 displaces outer bendable member 478 in the radial direction with a force. This force can be used to dilate or displace portions of the anatomy. This configuration is useful to exert force in a particular radial direction. FIG. 4S' shows a partial perspective view of the outer stationary member 476 of FIG. 4R. FIG. 4T shows a sectional view of a mechanical dilator comprising an inner member 480, a first outer hemi-tubular member 482 and a second outer hemi-tubular member 484. In FIG. 4U, movement of inner member 480 displaces first outer hemi-tubular member 482 and second outer hemi-tubular member 484 in the radial direction with a force. This force can be used to dilate or displace portions of the anatomy. This configuration is useful to exert force in two diametrically opposite regions. FIG. 4U' shows a partial perspective view of the first outer hemi-tubular member 482 and the second outer hemi-tubular member 484 of FIG. 4T. FIG. 4V shows a sectional view of a mechanical dilator comprising an inner member 486, a first outer curved member 488 and a second outer curved member 490. In FIG. 4W, movement of inner member 486 displaces first outer curved member 488 and second outer curved member 490 in the radial direction with a force. This force can be used to dilate or displace portions of the anatomy. This configuration is useful to exert force over smaller areas in two diametrically opposite regions. FIG. 4W' shows a partial perspective view of the first outer curved member 488 and the second outer curved member 490 of FIG. 4V. Similar designs for mechanical dilators in FIGS. 4H through 4Q are possible using three or more displaceable members. The inner member in the mechanical dilators disclosed herein may be replaced by a balloon for displacing the outer members to exert an outward radial force.

Several other designs of the working device may also be used including but not limited to cutters, chompers, rotating drills, rotating blades, tapered dilators, punches, dissectors, burs, non-inflating mechanically expandable members, high frequency mechanical vibrators, radiofrequency ablation devices, microwave ablation devices, laser devices (e.g. $CO_2$, Argon, potassium titanyl phosphate, Holmium:YAG and Nd:YAG laser devices), snares, biopsy tools, scopes and devices that introduce diagnostic or therapeutic agents.

Figure 5A:
FIG. 5A shows a perspective view of a balloon that comprises a conical proximal portion, a conical distal portion and a cylindrical portion between the conical proximal portion and the conical distal portion.
Figure 5B:
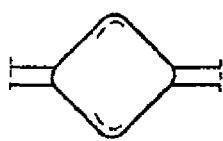
FIG. 5B shows a perspective view of a conical balloon.
Figure 5C:
FIG. 5C shows a perspective view of a spherical balloon.
Figure 5D:
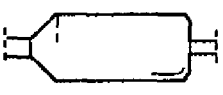
FIG. 5D shows a perspective view of a conical/square long balloon.
Figure 5E:
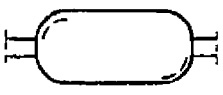
FIG. 5E shows a perspective view of a long spherical balloon.
Figure 5F:
FIG. 5F shows a perspective view of a bi-lobed "dog bone" balloon.
Figure 5G:
FIG. 5G shows a perspective view of an offset balloon.
Figure 5H:
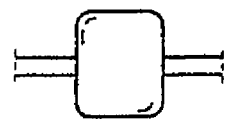
FIG. 5H shows a perspective view of a square balloon.
Figure 5I:
FIG. 5I shows a perspective view of a conical/square balloon.
Figure 5J:
FIG. 5J shows a perspective view of a conical/spherical long balloon.
Figure 5K:
FIG. 5K shows a perspective view of an embodiment of a tapered balloon.
Figure 5L:
FIG. 5L shows a perspective view of a stepped balloon.
Figure 5M:
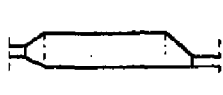
FIG. 5M shows a perspective view of a conical/offset balloon.
Figure 5N:
FIG. 5N shows a perspective view of a curved balloon.
Figure 5:
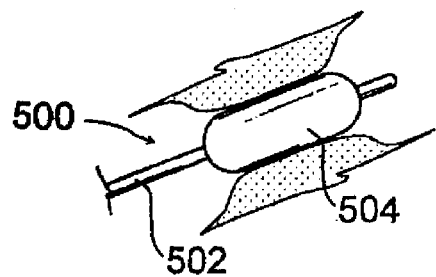
Figure 5:
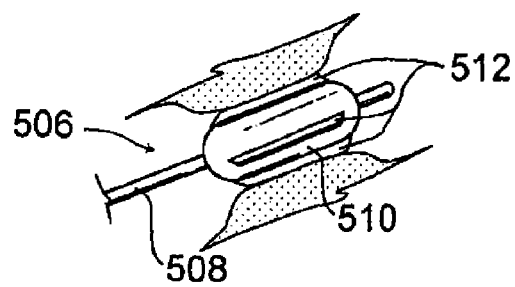
Figure 5:
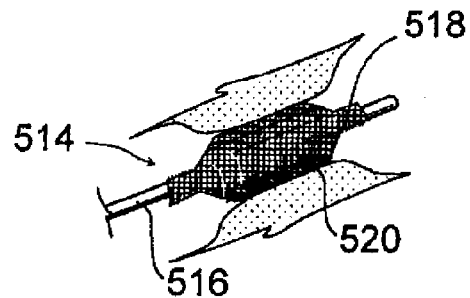
Figure 6:
FIG. 6A shows a partial perspective view of a shaft design useable in the various devices disclosed herein, wherein the shaft comprises an external spiral wire.
FIG. 6B shows a partial perspective view of a shaft design for the various devices disclosed herein, wherein the shaft comprises a stiffening wire.
FIG. 6C shows a partial perspective view of an embodiment of a shaft design for the various devices disclosed herein, wherein the shaft comprises stiffening rings.
FIG. 6D shows a partial perspective view of a shaft design for the various devices disclosed herein, wherein the shaft comprises controllable stiffening elements.
FIG. 6E shows a partial perspective view of a shaft design for the various devices disclosed herein, wherein the shaft comprises a hypotube.
FIG. 6F shows a partial perspective cut-away view of a shaft design for the various devices disclosed herein, wherein the shaft comprises a braid.
FIG. 6G shows a partial perspective view of an embodiment of a device comprising a shaft having a plastically deformable region.
FIG. 6H shows a partial perspective view of a device comprising a shaft having a flexible element.
FIG. 6I shows a partial perspective view of a shaft comprising a malleable element.
FIG. 6J shows a partial perspective view of the shaft of FIG. 6I in a bent configuration.
FIG. 6K shows a cross sectional view through plane 6K-6K of FIG. 6I.
FIG. 6L shows a partial sectional view of an embodiment of a controllably deformable shaft.
FIG. 6M shows a partial sectional view of the controllably deformable shaft of FIG. 6L in a deformed state.
FIG. 6N shows a perspective view of a balloon catheter comprising a rigid or semi-rigid member.
FIGS. 6O through 6Q show sectional views of a balloon catheter that comprises an insertable and removable element.
Figure 6:
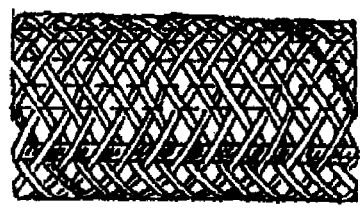
Figure 5:
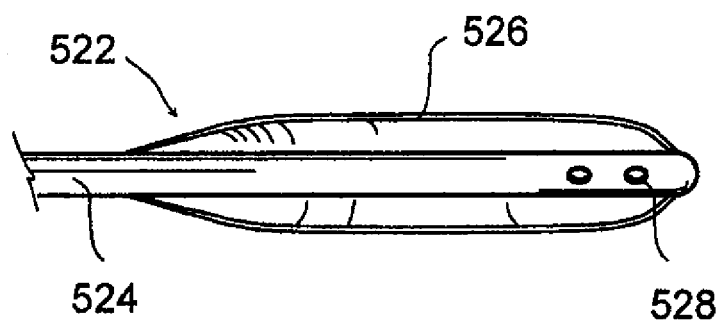
Figure 5:
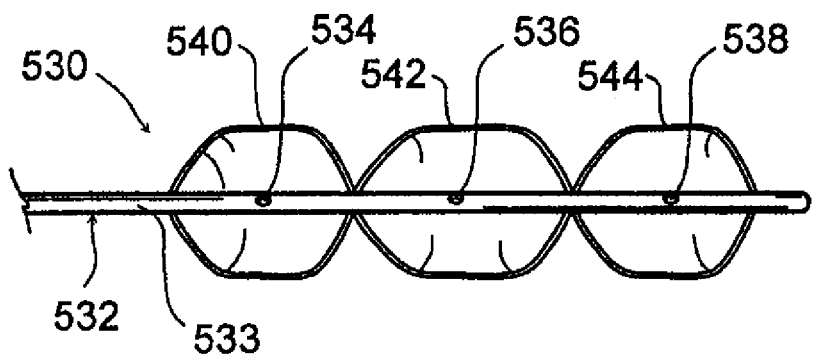
Figure 5:
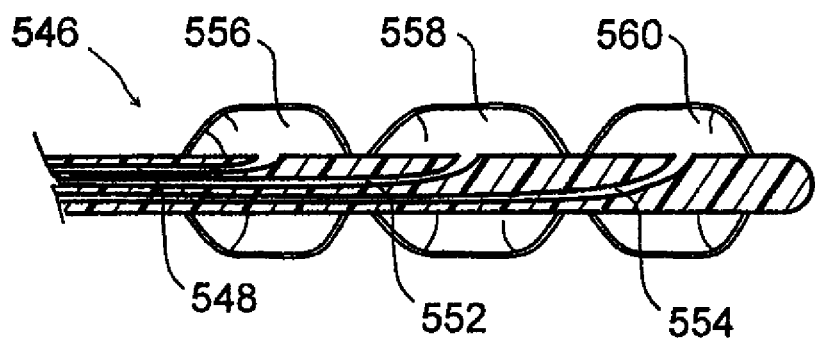
Figure 5:
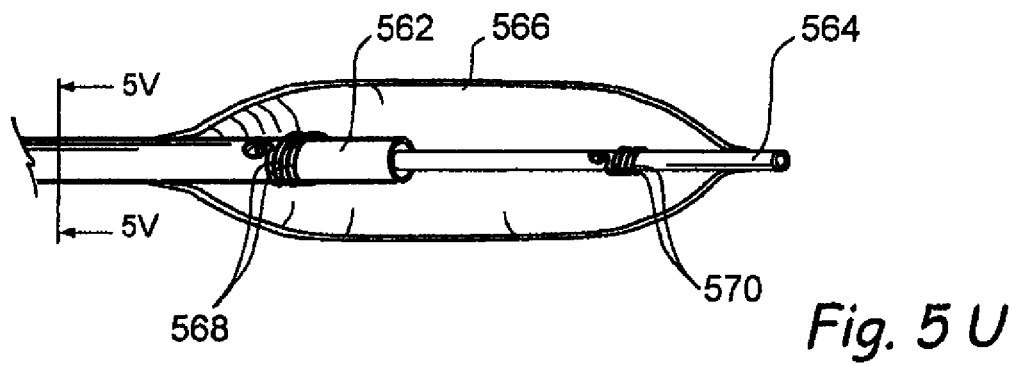
Figure 5:
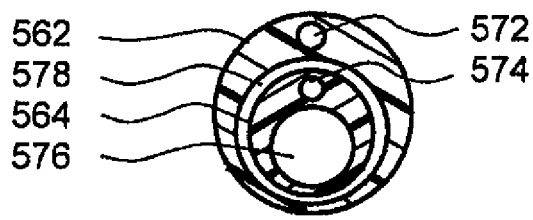
Figure 5:
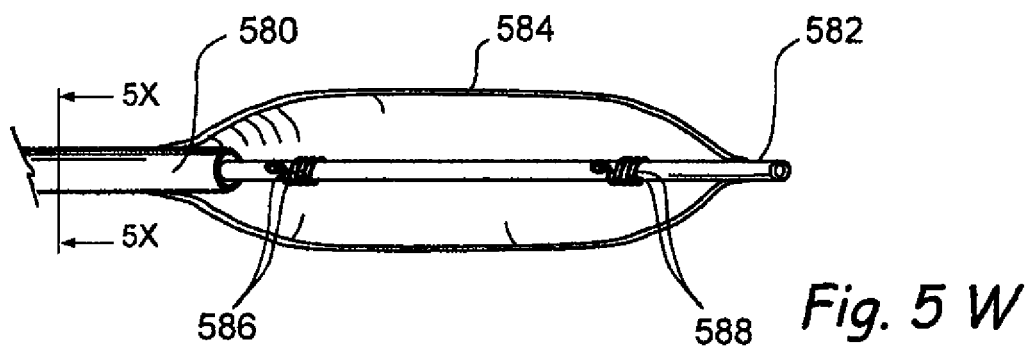
Figure 5:
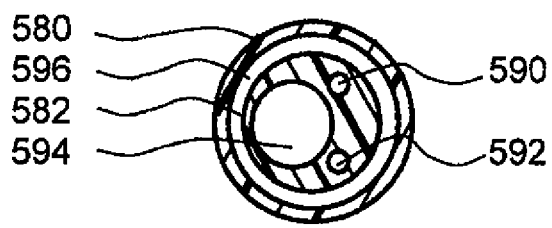

FIG. 5A shows a perspective view of an embodiment of a balloon comprising a conical proximal portion, a conical distal portion and a cylindrical portion between the conical proximal portion and the conical distal portion. FIGS. 5B to 5N show perspective views of several alternate embodiments of the balloon. FIG. 5B shows a conical balloon, FIG. 5C shows a spherical balloon, FIG. 5D shows a conical/square long balloon, FIG. 5E shows a long spherical balloon, FIG. 5F shows a dog bone balloon, FIG. 5G shows a offset balloon, FIG. 5H shows a square balloon, FIG. 5I shows a conical/square balloon, FIG. 5J shows a conical/spherical long balloon, FIG. 5K shows a tapered balloon, FIG. 5L shows a stepped balloon, FIG. 5M shows a conical/offset balloon and FIG. 5N shows a curved balloon.

The balloons disclosed herein can be fabricated from biocompatible materials including but not limited to polyethylene terephthalate, Nylon, polyurethane, polyvinyl chloride, crosslinked polyethylene, polyolefins, HPTFE, HPE, HDPE, LDPE, EPTFE, block copolymers, latex and silicone. The balloons disclosed herein can be fabricated by a variety of fabrication methods including but not limited to molding, blow molding, dipping, extruding etc.

The balloons disclosed herein can be inflated with a variety of inflation media including but not limited to saline, water, air, radiographic contrast materials, diagnostic or therapeutic substances, ultrasound echogenic materials and fluids that conduct heat, cold or electricity.

The balloons in this invention can also be modified to deliver diagnostic or therapeutic substances to the target anatomy. For example, FIG. 5O shows a partial perspective view of an embodiment of a balloon catheter device 500 comprising a balloon for delivering diagnostic or therapeutic substances. Balloon catheter device 500 comprises a flexible catheter 502 having a balloon 504 thereon. The catheter device 500 is advanced, with balloon 504 deflated, into a passageway such as a nostril, nasal cavity, meatus, ostium, interior of a sinus, etc. and positioned with the deflated balloon 504 situated within an ostium, passageway or adjacent to tissue or matter that is to be dilated, expanded or compressed (e.g., to apply pressure for hemostasis, etc.). Thereafter, the balloon 504 may be inflated to dilate, expand or compress the ostium, passageway, tissue or matter. Thereafter the balloon 504 may be deflated and the device 500 may be removed. This balloon 504 may also be coated, impregnated or otherwise provided with a medicament or substance that will elute from the balloon into the adjacent tissue (e.g., bathing the adjacent tissue with drug or radiating the tissue with thermal or other energy to shrink the tissues in contact with the balloon 504). Alternatively, in some embodiments, the balloon may have a plurality of apertures or openings through which a substance may be delivered, sometimes under pressure, to cause the substance to bathe or diffuse into the tissues adjacent to the balloon. Alternatively, in some embodiments, radioactive seeds, threads, ribbons, gas or liquid, etc. may be advanced into the catheter shaft 502 or balloon 504 or a completely separate catheter body for some period of time to expose the adjacent tissue and to achieve a desired diagnostic or therapeutic effect (e.g. tissue shrinkage, etc.).

The balloons in this invention can have a variety of surface features to enhance the diagnostic or therapeutic effects of a procedure. For example, FIG. 5P shows a partial perspective view of an embodiment of a balloon/cutter catheter device 506 comprising a flexible catheter 508 having a balloon 510 with one or more cutter blades 512 formed thereon. The device 506 is advanced, with balloon 510 deflated, into a passageway such as a nostril, nasal cavity, meatus, ostium, interior of a sinus, etc. and positioned with the deflated balloon 510 situated within an ostium, passageway or adjacent to tissue or matter that is to be dilated, expanded or compressed and in which it is desired to make one or more cuts or scores (e.g. to control the fracturing of tissue during expansion and minimize tissue trauma etc.). Thereafter, the balloon 510 is inflated to dilate, expand or compress the ostium, passageway, tissue or matter and causing the cutter blade(s) 512 to make cut(s) in the adjacent tissue or matter. Thereafter the balloon 510 is deflated and the device 506 is removed. The blade may be energized with mono or bi-polar RF energy or otherwise heated such that it will cut the tissues while also causing hemostasis and/or to cause thermal contraction of collagen fibers or other connective tissue proteins, remodeling or softening of cartilage, etc.

The balloons in this invention can have a variety of reinforcing means to enhance the balloon properties. For example, FIG. 5Q shows a perspective view of an embodiment of a balloon catheter device 514 comprising a flexible catheter 516 having a balloon 518 with one or more reinforcing means 520 thereon. In this example, reinforcing means 520 is a braid attached on the external surface of balloon 518. The reinforcing braid can be constructed from suitable materials like polymer filaments (e.g. PET or Kevlar filaments), metallic filaments (e.g. SS316 or Nitinol filaments) and metallic or non-metallic meshes or sheets. A variety of other reinforcing means can be used including but not limited to reinforcing coatings, external or internal reinforcing coils, reinforcing fabric, reinforcing meshes and reinforcing wires, reinforcing rings, filaments embedded in balloon materials etc.

The balloons in this invention can have a variety of inflation means to enhance the balloon properties. FIG. 5R shows a partial sectional view of an embodiment of a balloon catheter 522 comprising a shaft 524 and a balloon 526. Shaft 524 comprises a balloon inflation lumen. The distal portion of balloon inflation lumen terminates in inflation ports 528 located near the distal end of balloon 526. Thus, when balloon catheter 522 is inserted in an orifice and balloon 526 is inflated, the distal portion of balloon 526 inflates earlier than the proximal portion of balloon 526. This prevents balloon 526 from slipping back out of the orifice.

FIGS. 5S through 5T illustrate designs of balloon catheters comprising multiple balloons. FIG. 5S shows a partial sectional view of an embodiment of a balloon catheter 530 comprising a shaft 532 with a lumen 533. Lumen 533 opens into three orifices located on shaft 532 namely a first orifice 534, a second orifice 536 and a third orifice 538. The three orifices are used to inflate three balloons. First orifice 534 inflates a first balloon 540, second orifice 536 inflates a second balloon 542 and third orifice 538 inflates third balloon 544. In one embodiment, first balloon 540 and third balloon 544 are inflated with a single lumen and second balloon 542 is inflated with a different lumen. In another embodiment, first balloon 540, second balloon 542 and third balloon 544 interconnected and are inflated with a single lumen. A valve mechanism allows first balloon and second balloon to inflate before allowing second balloon to inflate.

Alternatively, the balloons can be inflated by separate lumens. FIG. 5T shows a partial sectional view of an embodiment of a balloon catheter 546 comprising a shaft 548 comprising a first inflation lumen 550, a second inflation lumen 552 and a third inflation lumen 554. The three inflation lumens are used to inflate three non-connected balloons. First inflation lumen 550 inflates a first balloon 556, second inflation lumen 552 inflates a second balloon 558 and third inflation lumen 554 inflates a third balloon 560.

The devices disclosed herein may comprise one or more navigation or visualization modalities. FIGS. 5U through 5AB illustrate perspective and sectional views of various embodiments of a balloon catheter comprising sensors. FIG. 5U shows a partial perspective view of a balloon catheter comprising an outer member 562, an inner member 564 and a balloon 566 attached to distal region of outer member 562 and distal region of inner member 564. The balloon catheter further comprises a first sensor 568 located on the distal region of outer member 562 and a second sensor 570 located on the distal region of inner member 564. FIG. 5V shows a crossection through plane 5V-5V in FIG. 5U. Outer member 562 comprises a first sensor lumen 572 to receive the lead from first sensor 568. Inner member 564 comprises a second sensor lumen 574 to receive the lead from second sensor 570. Inner member 564 further comprises a circular lumen 576. Outer member 562 and inner member 564 enclose an annular lumen 578. In one embodiment, annular lumen 578 is a balloon inflation lumen.

FIG. 5W shows a partial perspective view of a balloon catheter comprising an outer member 580, an inner member 582 and a balloon 584 attached to distal region of outer member 580 and distal region of inner member 582. The balloon catheter further comprises a first sensor 586 located on the distal region of inner member 582 and a second sensor 588 located on the distal region of inner member 582 distal to first sensor 586. FIG. 5X shows a cross section through plane 5X-5X in FIG. 5W. Inner member 582 comprises a first sensor lumen 590 to receive the lead from first sensor 586 and a second sensor lumen 592 to receive the lead from second sensor 588. Inner member 582 further comprises a circular lumen 594. Outer member 580 and inner member 582 enclose an annular lumen 596. In one embodiment, annular lumen 596 is a balloon inflation lumen.

Figure 5Y:
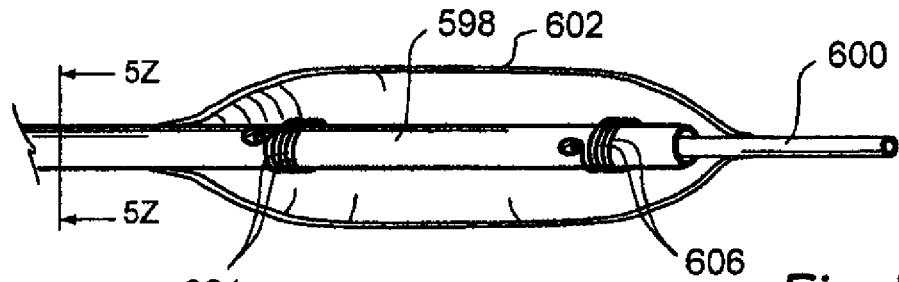
Figure 5Z:
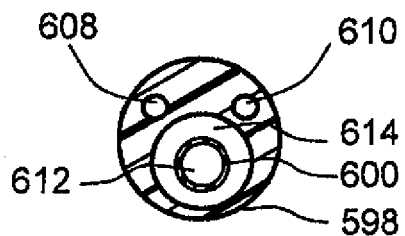
Figure 5A:
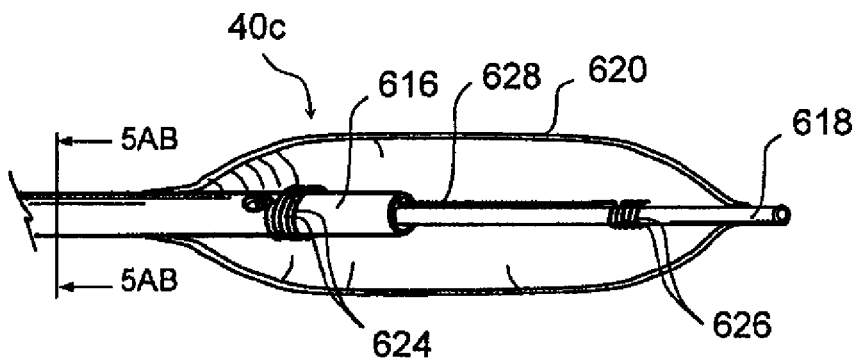
Figure 5A:
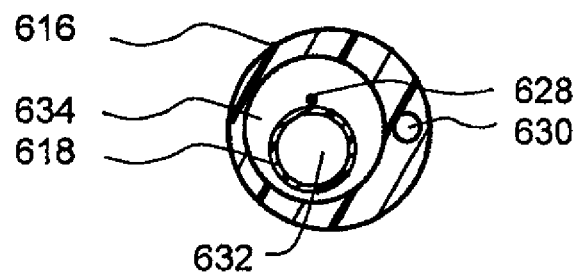

FIG. 5Y shows a partial perspective view of a balloon catheter comprising an outer member 598, an inner member 600 and a balloon 602 attached to distal region of outer member 598 and distal region of inner member 600. The balloon catheter further comprises a first sensor 604 located on the distal region of outer member 598 and a second sensor 606 located on the distal region of outer member 598 distal to first sensor 604. FIG. 5Z shows a cross section through plane 5Z-5Z in FIG. 5Y. Outer member 598 comprises a first sensor lumen 608 to receive the lead from first sensor 604 and a second sensor lumen 610 to receive the lead from second sensor 606. Inner member 600 comprises a circular lumen 612. Outer member 598 and inner member 600 enclose an annular lumen 614. In one embodiment, annular lumen 614 is a balloon inflation lumen.

The leads from the sensors may be attached on the surface of an element of the balloon catheter without being enclosed in a lumen. FIG. 5AA shows a partial perspective view of a balloon catheter comprising an outer member 616, an inner member 618 and a balloon 620 attached to distal region of outer member 616 and distal region of inner member 618. The balloon catheter further comprises a first sensor 624 located on the distal region of outer member 616 and a second sensor 626 located on the distal region of inner member 618. Second sensor 626 comprises a lead 628. FIG. 5AB shows a cross section through plane 5AB-5AB in FIG. 5AA. Outer member 616 comprises a first sensor lumen 630 to receive the lead from first sensor 624. Inner member 618 comprises a circular lumen 632. Lead 628 from second sensor 626 is attached on the outer surface of inner member 618 and is oriented parallel to inner member 618. Outer member 616 and inner member 618 enclose an annular lumen 634. In one embodiment, annular lumen 634 is a balloon inflation lumen. The sensors mentioned in FIGS. 5U through 5AB can be electromagnetic sensors or sensors including but not limited to location sensors, magnetic sensors, electromagnetic coils, RF transmitters, mini-transponders, ultrasound sensitive or emitting crystals, wire-matrices, micro-silicon chips, fiber-optic sensors, etc.

Figure 6A:
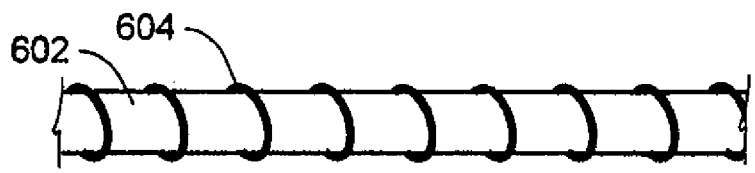
Figure 6B:
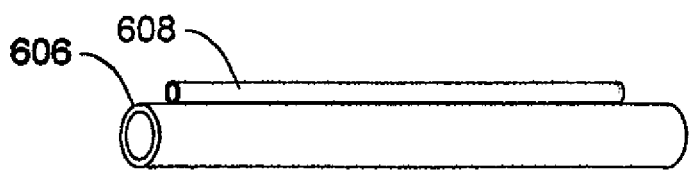
Figure 6C:
Figure 6D:
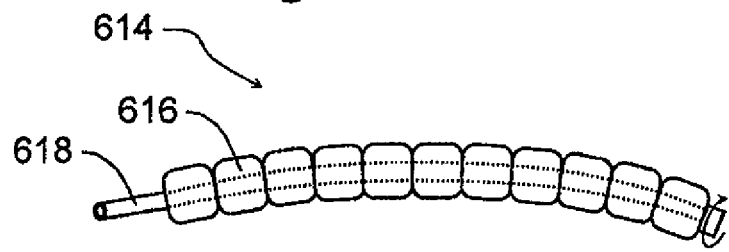
Figure 6E:
Figure 6:
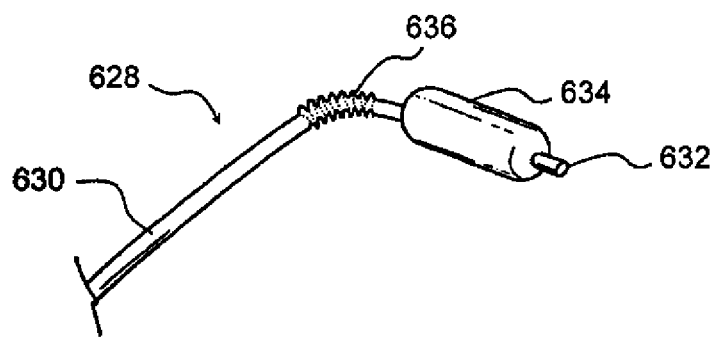
Figure 6:
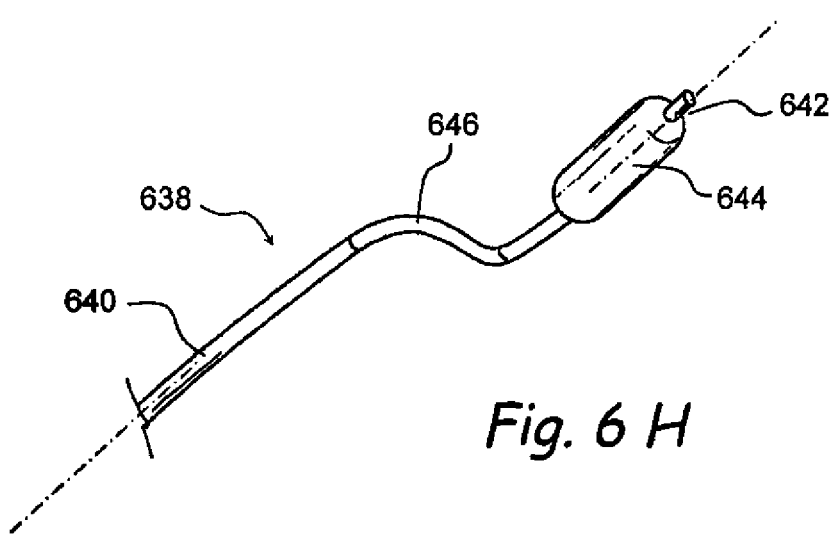
Figure 6:
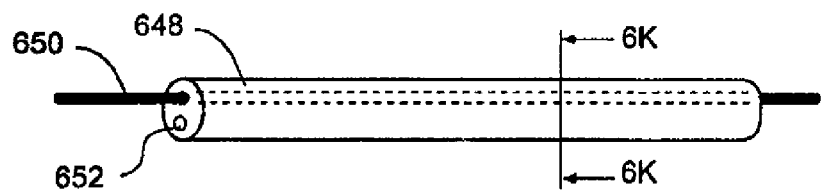
Figure 6:
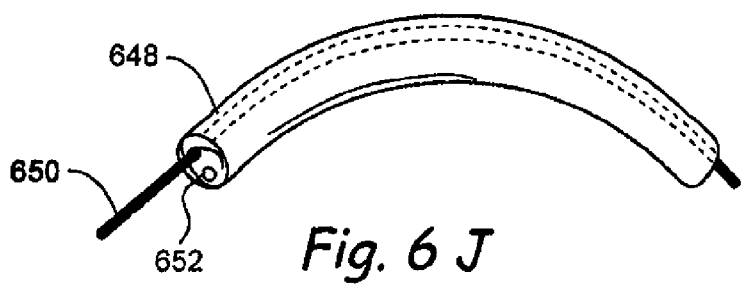
Figure 6:
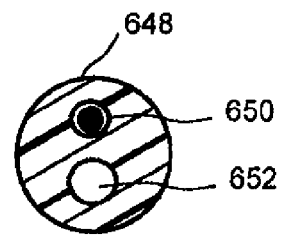
Figure 6:
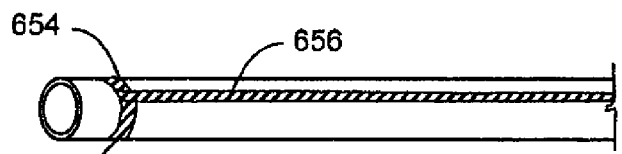
Figure 6:
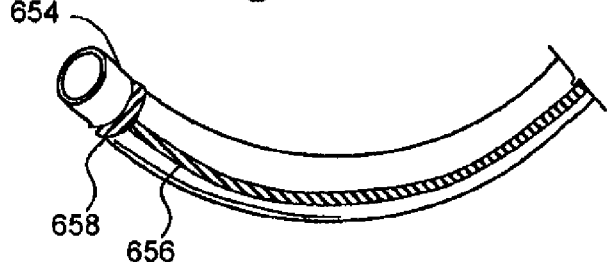

FIGS. 6A through 6G illustrate partial perspective views of several embodiments of shaft designs for the various devices disclosed herein. These shaft designs are especially useful for devices that encounter high torque or high burst pressures or require enhanced pushability, steerability and kink resistance. FIG. 6A shows a partial perspective view of an embodiment of a shaft 602 comprising a spiral element 604 wound around the shaft. Spiral element 604 can be made of suitable materials like metals (e.g. SS316L, SS304) and polymers. In one embodiment, spiral element 604 is in the form of round wire of diameter between 0.04 mm to 0.25 mm. In another embodiment, spiral element is in the form of flat wire of cross section dimensions ranging from 0.03 mm×0.08 mm to 0.08 mm×0.25 mm. FIG. 6B shows a partial perspective view of an embodiment of a shaft 606 comprising a reinforcing filament 608. Reinforcing filament 608 is substantially parallel to the axis of shaft 606. Shaft 606 with reinforcing filament 608 can be covered with a jacketing layer. Reinforcing filament 608 can be made of suitable materials like metals, polymers, glass fiber etc. Reinforcing filament 608 can also have shape memory characteristics. In one embodiment, reinforcing filament 608 is embedded in shaft 606. In another embodiment, reinforcing filament is introduced through a lumen in shaft 606. Shaft 606 may comprise more than one reinforcing filament 608. FIG. 6C shows a partial perspective view of an embodiment of a shaft 610 comprising one of more stiffening rings 612 along the length of shaft 610. FIG. 6D shows a partial perspective view of an embodiment of a shaft 614 comprising a series of controllably stiffening elements 616 along the length of the shaft. Shaft 614 further comprises a tension wire 618 that runs through controllably stiffening elements 616 and is attached to the most distal stiffening element. The tension in tension wire 618 causes controllably stiffening elements 616 to come into contact with each other with a force. Friction between controllably stiffening elements 616 causes shaft 614 to have a certain stiffness. Increasing the tension in tension wire 618 increases the force with which controllably stiffening elements 616 come into contact with each other. This increases the friction between controllably stiffening elements 616 which in turn increases the stiffness of shaft 614. Similarly, reducing the tension in tension wire 618 reduces the stiffness of shaft 614. Controllably stiffening elements 616 can be made from suitable materials like metal, polymers and composites. In one embodiment, controllably stiffening elements 616 are separated from each other by one or more springs. Tension wire 618 can be made from metals like SS316. Tension wire 618 may also be used to cause the device to actively bend or shorten in response to tension. FIG. 6E shows a partial perspective view of an embodiment of a shaft 620 comprising a hypotube 622. In one embodiment, hypotube 622 is located on the exterior surface of shaft 620. In another embodiment, hypotube 622 is embedded in shaft 620. Hypotube 620 can be made of metals like stainless steel 316 or suitable polymers. FIGS. 6F and 6F' show a partial perspective view of an embodiment of a shaft 624 comprising a reinforcing element 626 in the form of a reinforcing braid or mesh located on the outer surface of shaft 624. Reinforcing element 626 can be made of suitable materials like polymer filaments (e.g. PET or Kevlar filaments), metallic wires e.g. SS316 wires etc. The braid pattern can be regular braid pattern, diamond braid pattern, diamond braid pattern with a half load etc. In one embodiment, the outer surface of reinforcing element 626 is covered with a jacketing layer.

The shafts of various devices disclosed herein may be non homogenous along their length. Examples of such shafts are illustrated in FIGS. 6G through 6H. FIG. 6G shows a partial perspective view of an embodiment of a device comprising a shaft 628 comprising a proximal portion 630, a distal portion 632, a working element 634 and a plastically deformable region 636 located between the proximal portion 630 and distal portion 632. Plastically deformable region 636 can be deformed by a physician to adjust the angle between proximal portion 630 and distal portion 632. This enables the devices to be used for several different anatomical regions of the same patient. Also, such devices can be adjusted for optimal navigation through a patient's anatomy. In one embodiment, shaft 628 comprises multiple plastically deformable regions. In another embodiment plastically deformable region 636 is located within working element 634. Such a design comprising one or more plastically deformable regions can be used for any of the devices mentioned herein like catheters with working elements, guide catheters, guide catheters with a pre-set shape, steerable guide catheters, steerable catheters, guidewires, guidewires with a pre-set shape, steerable guidewires, ports, introducers, sheaths etc.

FIG. 6H shows a partial perspective view of an embodiment of a device comprising a shaft with a flexible element. The design is illustrated as a shaft 638 comprising a proximal portion 640, a distal portion 642 and a working element 644 (e.g. a balloon). Shaft 638 further comprises a flexible element 646 located between proximal portion 640 and distal portion 642. This design enables proximal portion 640 to bend with respect to distal portion 642 making it easier to navigate through the complex anatomy and deliver working element 644 to the desired location. In one embodiment, shaft 638 comprises multiple flexible elements. In another embodiment, flexible element 646 is located within working element 644. Such a design comprising one or more flexible elements can be used for any of the devices mentioned herein like catheters with working elements, guide catheters, guide catheters with a pre-set shape, steerable guide catheters, steerable catheters, guidewires, guidewires with a pre-set shape, steerable guidewires, ports, introducers, sheaths etc.

FIGS. 6I through 6K illustrate an example of a shaft comprising a malleable element. FIG. 6I shows a partial perspective view of an embodiment of a shaft 648 comprising malleable element 650 and a lumen 652 wherein shaft 648 is in a substantially straight configuration. Malleable element 650 is embedded in shaft 648 such that the axis of malleable element 650 is substantially parallel to the axis of shaft 648. FIG. 6J shows a partial perspective view of the embodiment of FIG. 6I in a bent configuration. FIG. 6K shows a cross sectional view through plane 6K-6K of FIG. 6I showing shaft 648 comprising malleable element 650 and a lumen 652. In one embodiment, shaft 648 comprises more than one malleable element.

FIGS. 6L through 6M show an embodiment of a controllably deformable shaft. FIG. 6L shows a partial sectional view of an embodiment of a controllably deformable shaft 654 comprising a pull wire 656 attached to a pull wire terminator 658 located near the distal end of shaft 654. FIG. 6M shows a partial sectional view of the controllably deformable shaft 654 of FIG. 6L in a bent orientation when pull wire 656 is pulled in the proximal direction. The deformation can be varied by varying the location of pull wire terminator 658 and the stiffness of various sections of shaft 658. The stiffness of a section of shaft 658 can be varied by adding reinforcing coatings, external or internal reinforcing coils, reinforcing fabric, reinforcing meshes and reinforcing wires, hinged elements, embedded filaments, reinforcing rings etc.

FIG. 6N shows a perspective view of a balloon catheter comprising a rigid or semi-rigid member. The balloon catheter comprises a rigid or semi-rigid member 660 and a balloon 662 located on the distal region of rigid or semi-rigid member 660. Rigid or semi-rigid member 660 may comprise one or more lumens. Rigid or semi-rigid member 660 may comprise one or more bent, curved or angled regions. Balloon 662 is inflated by a balloon inflation tube 664 comprising a hub 666 at the proximal end of balloon inflation tube 664. In one embodiment, balloon inflation tube 664 is fully attached along its length to rigid or semi-rigid member 660. In another embodiment, balloon inflation tube 664 is partially attached along its length to rigid or semi-rigid member 660.

FIGS. 6O through 6Q illustrate sectional views of a balloon catheter comprising an insertable and removable element. FIG. 6O shows a balloon catheter 668 comprising a balloon 670, a first lumen 672 and a balloon inflation lumen 674 opening into balloon 670 through an inflation port 676. FIG. 6P shows an insertable element 678 having a proximal end 680 and a distal end 682. In one embodiment, distal end 682 ends in a sharp tip for penetrating tissue. In one embodiment, insertable element 678 comprises one or more bent, angled or curved regions 684. Insertable element 678 can be fabricated from a variety of materials to obtain properties including but not limited to rigidity, shape memory, elasticity, ability to be plastically deformed etc. In FIG. 6Q, insertable element 678 is inserted into balloon catheter 668 through first lumen 672. This combination can be used to perform a diagnostic or therapeutic procedure. Insertable element 678 may be removed during or after the procedure.

Figure 7A:
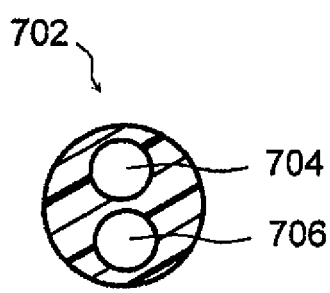
FIG. 7A shows a cross sectional view through a balloon catheter shaft comprising two cylindrical lumens.
Figure 7B:
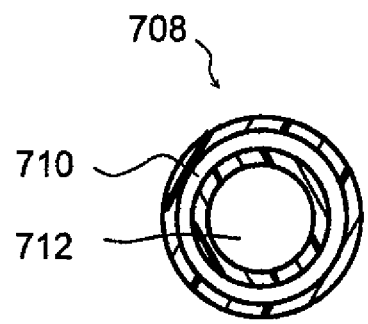
FIG. 7B shows a cross sectional view through a balloon catheter shaft comprising an inner lumen and an annular outer lumen disposed about the inner lumen.
Figure 7C:
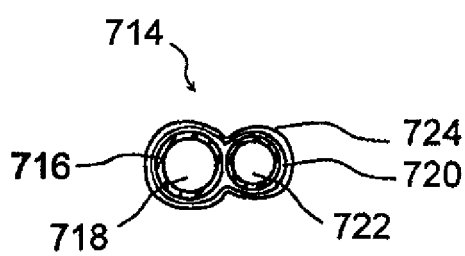
FIG. 7C shows a cross sectional view through a balloon catheter shaft which comprises a first tubular element with a first lumen, a second tubular element with a second lumen and a jacket surrounding the first and second tubular elements.
Figure 7D:
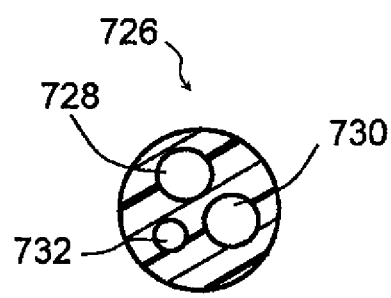
FIG. 7D shows a cross sectional view through a balloon catheter shaft comprising three lumens.
Figure 7E:
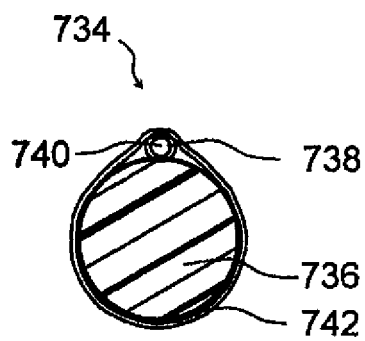
FIG. 7E shows a cross sectional view through a balloon catheter shaft comprising a cylindrical element, a tubular element that has a lumen and a jacket surrounding the cylindrical element and the tubular element.
Figure 7F:
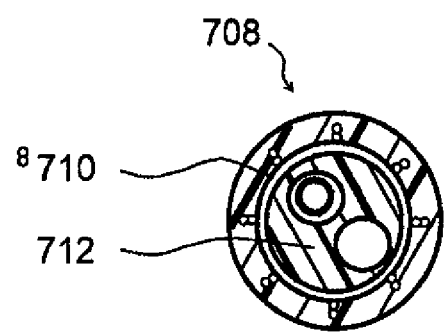
FIG. 7F shows a cross sectional view of through a balloon catheter shaft comprising an embedded braid.
Figure 7:
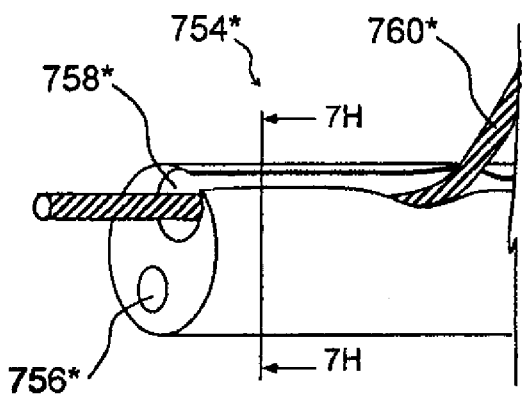
FIG. 7G shows a partial perspective view of a catheter shaft comprising a zipper lumen with a guide extending through a portion of the zipper lumen.
FIG. 7H shows a cross sectional view through line 7H-7H of FIG. 7G.
FIG. 7I shows is a partial longitudinal sectional view of a catheter shaft comprising a rapid exchange lumen with a guide extending through the rapid exchange lumen.
FIG. 7J shows a cross sectional view of the catheter shaft of FIG. 7I through line 7J-7J.
FIG. 7K shows a cross sectional view of the catheter shaft of FIG. 7I through line 7K-7K.
FIG. 7L is a partial perspective view of a balloon catheter device of the present invention comprising a through-lumen and a balloon inflation lumen within the shaft of the catheter.
FIG. 7M is a cross sectional view through line 7M-7M of FIG. 7L.
FIG. 7N is a cross sectional view through line 7N-7N of FIG. 7L.
FIG. 7O is a partial perspective view of another balloon catheter device of the present invention comprising a through lumen within the shaft of the catheter and a balloon inflation tube disposed next to and optionally attached to the catheter shaft.
FIG. 7P is a cross sectional view through line 7P-7P of FIG. 7O.
FIG. 7Q is a cross sectional view through line 7Q-7Q of FIG. 7O.
Figure 7:
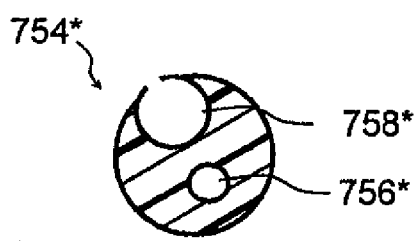
Figure 7:
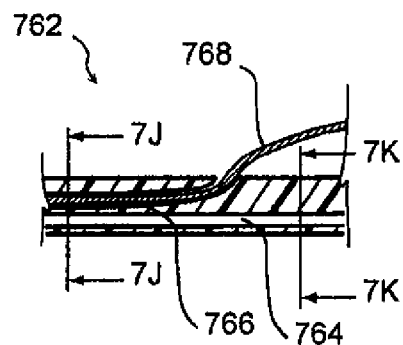
Figure 7:
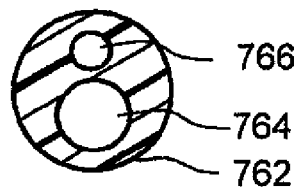
Figure 7:
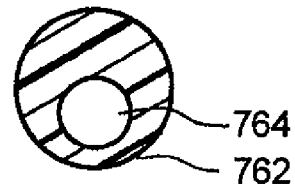

FIGS. 7A through 7K show cross sectional views of several embodiments of lumen orientation in the devices disclosed herein. FIG. 7A shows a cross sectional view of an embodiment of a shaft 702 comprising a first lumen 704 and a second lumen 706. In one embodiment, first lumen 704 is a guidewire lumen and second lumen 706 is an inflation lumen. FIG. 7B shows a cross sectional view of an embodiment of a shaft 708 comprising a first lumen 710 and a annular second lumen 712 such that second annular lumen 712 is substantially coaxial with first lumen 710. In one embodiment, first lumen 710 is a guidewire lumen and annular second lumen 712 is an inflation lumen. FIG. 7C shows a cross sectional view of an embodiment of a shaft 714 comprising a first tubular element 716 comprising a first lumen 718, a second tubular element 720 comprising a second lumen 722 and a jacket 724 surrounding first tubular element 716 and second tubular element 720. In one embodiment, first lumen 718 is a guidewire lumen and second lumen 722 is an inflation lumen. FIG. 7D shows a cross sectional view of an embodiment of a shaft 726 comprising a first lumen 728, a second lumen 730 and a third lumen 732. In one embodiment, first lumen 728 is a guidewire lumen, second lumen 730 is an irrigation/aspiration lumen and third lumen 732 is an inflation lumen. FIG. 7E shows a cross sectional view of an embodiment of a shaft 734 comprising a cylindrical element 736, a tubular element 738 comprising a lumen 740 and a jacket 742 surrounding cylindrical element 736 and tubular element 738. FIG. 7F shows a cross sectional view of an embodiment of a shaft 744 comprising a tubular member 746 comprising a first lumen 748 and a second lumen 750; a first coating 752 located on the outer surface of tubular member 746; a braid 754 located on the outer surface of first coating 752 and a second coating 756 surrounding braid 754. First lumen 748 is lined with a suitable coating 758 like hydrophilic lubricious coating, hydrophobic lubricious coating, abrasion resisting coating etc. In one embodiment, first lumen 748 is a guidewire lumen and second lumen 750 is an inflation lumen. The lumens disclosed herein can be lined with suitable coatings like hydrophilic lubricious coatings, hydrophobic lubricious coatings, abrasion resisting coatings, radiopaque coatings, echogenic coatings etc.

FIG. 7G shows a partial perspective view of an embodiment of a shaft 754* comprising a first lumen 756* and a zipper lumen 758*. Zipper lumen 758* allows a device like a guidewire 760* to be easily introduced into or removed from shaft 754*. FIG. 7H shows a cross sectional view through plane 7H-7H in FIG. 7G showing the orientations of first lumen 756* and zipper lumen 758*.

FIG. 7I shows a cross sectional view of an embodiment of a shaft 762 comprising a first lumen 764 and a rapid exchange lumen 766. Rapid exchange lumen 766 extends from the distal end of shaft 762 to a proximal region. Rapid exchange lumen 766 enables shaft 762 to be easily and quickly introduced or removed over an exchange device like a guidewire 768. FIG. 7J shows a cross sectional view through plane 7J-7J in FIG. 7I showing first lumen 764 and rapid exchange lumen 766. FIG. 7K shows a cross sectional view through plane 7K-7K in FIG. 7I showing first lumen 764.

FIGS. 7L through 7Q shows perspective and sectional views of lumens for the devices disclosed herein that are not present throughout the length of the devices. FIG. 7L shows a perspective view of a balloon catheter comprising a shaft 770, a balloon 772 and a lumen 774 that is present throughout shaft 770. The balloon catheter further comprises a balloon inflation lumen 776 that opens into balloon 772. The distal end of balloon inflation lumen 776 is plugged with a plug 778. FIG. 7M shows a crossection through plane 7M-7M in FIG. 7L showing shaft 770 comprising lumen 774 and balloon inflation lumen 776. FIG. 7N shows a crossection through plane 7N-7N in FIG. 7L showing shaft 770 comprising lumen 774 and plug 778. FIG. 7O shows a perspective view of a balloon catheter comprising a shaft 780, a balloon 782 and a lumen 786 that is present throughout shaft 780. The balloon catheter further comprises a balloon inflation lumen 784. The distal end of balloon inflation lumen 784 opens into balloon 782. FIG. 7P shows a crossection through plane 7P-7P in FIG. 7O showing shaft 780 comprising lumen 786 and balloon inflation lumen 784. FIG. 7Q shows a crossection through plane 7Q-7Q in FIG. 7O showing shaft 780 comprising lumen 786.

FIGS. 8A through 8E show partial perspective views of several embodiments of markers that may be present on the elements of the devices mentioned herein. FIG. 8A shows a partial perspective view of an embodiment of a shaft 800 comprising a plurality of distance markers 802 located along the length of shaft 800. FIG. 8B shows a partial perspective view of an embodiment of a shaft 804 comprising a plurality of radiographic markers 806 located along the length of shaft 804. FIG. 8C shows a partial perspective view of an embodiment of a shaft 808 comprising a plurality of ring shaped radiographic markers 810 located along the length of shaft 808. FIG. 8D shows a partial perspective view of an embodiment of a balloon catheter 812 comprising a shaft 814 and a balloon 816. Balloon 816 comprises a plurality of radiographic markers 818 located on the outer surface of the balloon 816. Such markers 818 may be in a linear arrangement, non-linear arrangement or any other configuration that performs the desired marking function (e.g., delineating the length and/or diameter of the balloon, marking the proximal and/or distal ends of the balloon, etc.). FIGS. 8E and 8E' show partial perspective and longitudinal sectional views of an embodiment of a balloon catheter 820 comprising a shaft 822 and a balloon 824. Balloon 824 comprises a plurality of radiographic markers 826 located on the inner surface of the balloon 824. Such markers 826 may be in a linear arrangement, non-linear arrangement or any other configuration that performs the desired marking function (e.g., delineating the length and/or diameter of the balloon, marking the proximal and/or distal ends of the balloon, etc.). The devices disclosed herein may also comprise several other types of markers like ultrasound markers, radiofrequency markers and magnetic markers. Similarly, the devices disclosed herein may also comprise one or more sensors like electromagnetic sensors, electrical sensors, magnetic sensors, light sensors and ultrasound sensors.

The term "diagnostic or therapeutic substance" as used herein is to be broadly construed to include any feasible drugs, prodrugs, proteins, gene therapy preparations, cells, diagnostic agents, contrast or imaging agents, biologicals, etc. Such substances may be in bound or free form, liquid or solid, colloid or other suspension, solution or may be in the form of a gas or other fluid or nan-fluid. For example, in some applications where it is desired to treat or prevent a microbial infection, the substance delivered may comprise pharmaceutically acceptable salt or dosage form of an antimicrobial agent (e.g., antibiotic, antiviral, antiparasitic, antifungal, etc.), a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, immunomodulator), etc. Other non-limiting examples of diagnostic or therapeutic substances that may be useable in this invention are described in copending U.S. patent application Ser. No. 10/912,578 entitled Implantable Devices and Methods for Delivering Drugs and Other Substances to Treat Sinusitis and Other Disorders filed on Aug. 4, 2004, the entire disclosure of which is expressly incorporated herein by reference.

The term "nasal cavity" used herein to be broadly construed to include any cavity that is present in the anatomical structures of the nasal region including the nostrils and paranasal sinuses.

The term "trans-nasal" means through a nostril.

Although the methods and devices disclosed herein are illustrated in conjunction with particular paranasal sinuses, it is understood that these methods and devices can be used in other paranasal sinuses as well as other anatomical passageways of the ear, nose or throat.

Optionally, any of the working devices and guide catheters described herein may be configured or equipped to receive or be advanced over a guidewire or other guide member (e.g., an elongate probe, strand of sure material, other elongate member) unless to do so would render the device inoperable for its intended purpose. Some of the specific examples described herein include guidewires, but it is to be appreciated that the use of guidewires and the incorporation of guidewire lumens is not limited to only the specific examples in which guidewires or guidewire lumens are shown. The guidewires used in this invention may be constructed and coated as is common in the art of cardiology. This may include the use of coils, tapered or non-tapered core wires, radioopaque tips and/or entire lengths, shaping ribbons, variations of stiffness, PTFE, silicone, hydrophilic coatings, polymer coatings, etc. For the scope of this invention, these wires may possess dimensions of length between 5 and 75 cm and outer diameter between 0.005" and 0.050".

Several modalities can be used with the devices and methods disclosed herein for navigation and imaging of the devices within the anatomy. For example, the devices disclosed herein may comprise an endoscope for visualization of the target anatomy. The devices may also comprise ultrasound imaging modalities to image the anatomical passageways and other anatomical structures. The devices disclosed herein may comprise one or more magnetic elements especially on the distal end of the devices. Such magnetic elements may be used to navigate through the anatomy by using external magnetic fields. Such navigation may be controlled digitally using a computer interface. The devices disclosed herein may also comprise one or more markers (e.g. infra-red markers). The markers can be used to track the precise position and orientation of the devices using image guidance techniques. Several other imaging or navigating modalities including but not limited to fluoroscopic, radiofrequency localization, electromagnetic, magnetic and other radiative energy based modalities may also be used with the methods and devices disclosed herein. These imaging and navigation technologies may also be referenced by computer directly or indirectly to pre-existing or simultaneously created 3-D or 2-D data sets which help the doctor place the devices within the appropriate region of the anatomy.

The distal tip of devices mentioned herein may comprise a flexible tip or a soft, atraumatic tip. Also, the shaft of such devices may be designed for enhanced torquability.

The embodiments herein have been described primarily in conjunction with minimally invasive procedures, but they can also be used advantageously with existing open surgery or laparoscopic surgery techniques.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. All reasonable additions, deletions, modifications and alterations are to be considered equivalents of the described examples and embodiments and are to be included within the scope of the following claims.

The invention claimed is:

1. A system for treating a paranasal sinus by dilating a natural or manmade paranasal sinus opening, said system comprising:
   (a) an elongate shaft having a proximal end, a distal end and an outer diameter sized to allow the elongate shaft to be inserted into a patient's nose;
   (b) an expandable dilation device coupled with distal end of the elongate shaft, the expandable dilation device being expandable from a first configuration to a second configuration;
   the elongate shaft being advanceable, with the dilation device in its first configuration, through the patient's nose to a position where the dilation device is positioned within the paranasal sinus opening;
   the dilation device being expandable, while positioned within the paranasal sinus opening, from the first configuration to the second configuration, said second configuration being sized to cause dilation of the paranasal sinus opening, wherein said dilation device in said second configuration expands with sufficient force to cause breakage or rearrangement of bone which surrounds the paranasal sinus opening; and
   the expandable dilator being thereafter removable from the paranasal sinus opening such that the paranasal sinus opening remains dilated after removal of the dilator therefrom.

2. A system according to claim 1 wherein the elongate shaft has a curved or bent region which facilitates advancement of the dilation device into the paranasal sinus opening.

3. A system according to claim 2 wherein the curved or bent region is curved or bent to an angle of up to 135°.

4. A system according to claim 2 wherein the curved or bent region is curved or bent to an angle selected from: 0°, 30°, 45°, 60°, 70°, 90°, 120° and 135°.

5. A system according to claim 2 wherein the curved or bent region is malleable such that an operator may form it to a desired bend or curvature at the time of use.

6. A system according to claim 2 wherein the curved or bent region is formed in the elongate shaft at the time of manufacture.

7. A system comprising a plurality of devices according to claim 6 wherein each device has a different curved or bent region.

8. A system according to claim 1 wherein the dilation device comprises an inflatable structure which fills with inflation fluid thereby causing the inflatable structure to expand from the first configuration to the second configuration.

9. A system according to claim 1 wherein the dilation device comprises an expandable wall defining an internal space therewithin and wherein entry of fluid into the internal space causes the expandable wall to expand, thereby transitioning the dilation device from the first configuration to the second configuration.

10. A method for dilating a natural or man-made paranasal sinus opening in a patient, said method comprising the steps of:
  (a) obtaining or providing a system which comprises i) an elongate shaft having a proximal end, a distal end and an outer diameter sized to allow the elongate shaft to be inserted into a patient's nose and ii) an expandable dilation device coupled with distal end of the elongate shaft, the expandable dilation device being expandable from a first configuration to a second configuration;
  (b) inserting the elongate shaft into the patient's nose and advancing it, with the dilation device in its first configuration, through the patient's nose to a position where the dilation device is positioned within the paranasal sinus opening;
  (c) causing the dilation device to expand, while positioned within the paranasal sinus opening, from the first configuration to the second configuration, wherein said expansion from the first configuration to the second configuration causes dilation of the paranasal sinus opening, wherein said dilation device in the second configuration expands with sufficient force to cause breakage or rearrangement of bone which surrounds the paranasal sinus opening; and, thereafter,
  (d) removing the dilation device from the paranasal sinus opening such that the paranasal sinus opening remains dilated after removal of the dilation device therefrom.

11. A method according to claim 10 wherein the elongate shaft has a curved or bent region and wherein the curved or bent region is used during advancement of the device to facilitate positioning of the dilation device within the paranasal sinus opening.

12. A method according to claim 11 wherein the curved or bent region is curved or bent to an angle of up to 135°.

13. A method according to claim 11 wherein the curved or bent region is curved or bent to an angle selected from: 0°, 30°, 45°, 60°, 70°, 90°, 120° and 135°.

14. A method according to claim 11 wherein the curved or bent region is malleable and wherein the operator forms a desired bend or curvature at the time of use.

15. A method according to claim 11 wherein the curved or bent region is formed in the elongate shaft at the time of manufacture.

16. A method according to claim 15 wherein a plurality of said systems having differing curved or bent regions are obtained or provided and wherein the operator selects a device having a desired bend or curvature at the time of the procedure.

17. A method according to claim 10 wherein the dilation device comprises an inflatable structure and wherein the dilation device is caused to expand by causing inflation fluid to fill the inflatable structure thereby causing the dilation device to expand from the first configuration to the second configuration.

18. A method according to claim 10 wherein the dilation device comprises an expandable wall which defines an internal space therewithin and wherein the dilation device is caused to expand by causing fluid to enter into the internal space causing the expandable wall to expand and thereby transitioning the dilation device from the first configuration to the second configuration.

* * * * *